US008987423B2

(12) United States Patent
Bergeron et al.

(10) Patent No.: US 8,987,423 B2
(45) Date of Patent: Mar. 24, 2015

(54) MAGE ANTIGEN BINDING PROTEINS

(75) Inventors: Alain Bergeron, Quebec (CA); Normand Blais, Laval (CA); Remi M. Palmantier, Laval (CA); Anthony Pilorget, Laval (CA); Yves Fradet, McMahon (CA)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 71 days.

(21) Appl. No.: 13/811,189

(22) PCT Filed: Jul. 20, 2011

(86) PCT No.: PCT/EP2011/062458
§ 371 (c)(1),
(2), (4) Date: Jan. 18, 2013

(87) PCT Pub. No.: WO2012/010635
PCT Pub. Date: Jan. 26, 2012

(65) Prior Publication Data
US 2013/0123472 A1    May 16, 2013

Related U.S. Application Data

(60) Provisional application No. 61/366,742, filed on Jul. 22, 2010.

(51) Int. Cl.
| *C07K 16/30* | (2006.01) |
| *G01N 33/53* | (2006.01) |
| *G01N 33/574* | (2006.01) |
| *G01N 33/577* | (2006.01) |
| *C07K 16/18* | (2006.01) |

(52) U.S. Cl.
CPC ............ *C07K 16/18* (2013.01); *C07K 16/30* (2013.01); *G01N 33/57423* (2013.01); *G01N 33/5743* (2013.01); *C07K 2317/33* (2013.01); *C12N 2799/026* (2013.01)

USPC .............. 530/388.85; 530/387.3; 530/388.8; 536/23.53; 435/320.1; 435/252.3; 435/69.6; 435/7.23; 435/7.92

(58) Field of Classification Search
CPC .... C07K 16/30; C07K 16/18; C07K 2317/33; G01N 33/547–33/57484
See application file for complete search history.

(56) References Cited

FOREIGN PATENT DOCUMENTS

| WO | 2007147876 A2 | 12/2007 |
| WO | WO2007/147876 A2 * | 12/2007 |
| WO | 2011066265 A1 | 6/2011 |
| WO | WO2011/066265 A1 * | 6/2011 |

OTHER PUBLICATIONS

Paul, Fundamental Immunology, 3rd Edition, 1993, pp. 292-295.*
Rudikoff et al., Proc. Nat'l Acad. Sci. USA 1982; 79:1979-83.*
Dall'Acqua et al., Methods 2005; 36:43-60.*
De Genst et al., Dev Comp Immunol 2006; 30:187-98.*
Dhodapkar et al., Cancer Immunity 3:9 (2003) pp. 1-8.*
Jungbluth et al., Blood 2005; 106:167-174.*
Chitale Dhananjay A et al., "Expression of cancer-testis antigens in endometrial carcinomas using a tissue microarray"; Modern Pathology, vol. 18, No. 1,(Jan. 2005) pp. 119-126.
Daniel Perez et al., "Cancer testis antigen expression in gastrointestinal stromal tumors",International Journal of Cancer, Vo. 123, No. 7, (Oct. 1, 2008) pp. 1551-1554.
Valerie Picard et al., "MAGE-A9 mRNA and protein expression in bladder cancer",International Journal of Cancer, Vo. 120, No. 10 , (May 2007) pp. 2170-2177.
David L Figueiredo et al., High Expression of Cancer Testis Antigens Mage-A Mage-C1/CT7, Mage-C2/CT10, NY-ESO-a, and gage in advanced squamous cell carcinoma of the Larynx, Head & Neck, vol. 33, No. 5, Sep. 30, 2010, pp. 702-707.

* cited by examiner

*Primary Examiner* — Sheela J Huff
*Assistant Examiner* — Jessica H Roark
(74) *Attorney, Agent, or Firm* — Virginia G. Campen

(57) ABSTRACT

Antigen binding proteins, such as antibodies, which bind to human MAGE-A3, polynucleotides encoding such antigen binding proteins, and uses and manufacture thereof.

9 Claims, 15 Drawing Sheets

FIGURE 1

```
A2 (SEQ ID NO: 2)  ------------------------------------------------------------
A12(SEQ ID NO:11)  ------------------------------------------------------------
A3 (SEQ ID NO: 3)  ------------------------------------------------------------
A6 (SEQ ID NO: 6)  ------------------------------------------------------------
A4 (SEQ ID NO: 4)  ------------------------------------------------------------
A5 (SEQ ID NO: 5)  ------------------------------------------------------------
A1 (SEQ ID NO: 1)  ------------------------------------------------------------
A11(SEQ ID NO:10)  METQFRRGGLGCSPASIKRKKKREDSGDFGLQVSTMFSEDDFQSTERAPYGPQLQWSQDL  60
A8 (SEQ ID NO: 7)  ------------------------------------------------------------
A9 (SEQ ID NO: 8)  ------------------------------------------------------------
A10(SEQ ID NO: 9)  ------------------------------------------------------------

A2 (SEQ ID NO: 2)  --------------------------------------------------MPLEQRSQHC  10
A12(SEQ ID NO:11)  --------------------------------------------------MPLEQRSQHC  10
A3 (SEQ ID NO: 3)  --------------------------------------------------MPLEQRSQHC  10
A6 (SEQ ID NO: 6)  --------------------------------------------------MPLEQRSQHC  10
A4 (SEQ ID NO: 4)  --------------------------------------------------MSSEQKSQHC  10
A5 (SEQ ID NO: 5)  --------------------------------------------------MSLEQKSQHC  10
A1 (SEQ ID NO: 1)  --------------------------------------------------MSLEQRSLHC  10
A11(SEQ ID NO:10)  PRVQVFREQANLEDRSPRRTQRITGGEQVLWGPITQIFPTVRPADLTRVIMPLEQRSQHC 120
A8 (SEQ ID NO: 7)  --------------------------------------------------MLLGQKSQRY  10
A9 (SEQ ID NO: 8)  --------------------------------------------------MSLEQRSPHC  10
A10(SEQ ID NO: 9)  --------------------------------------------------MPRAPKRQRC  10

A2 (SEQ ID NO: 2)  KPEEGLEARGEALGLVGAQAPATEEQQ--------------------TASSSSTLVEVT  49
A12(SEQ ID NO:11)  KPEEGLEAQGEALGLVGAQAPATEEQE--------------------TASSSSTLVEVT  49
A3 (SEQ ID NO: 3)  KPEEGLEARGEALGLVGAQAPATEEQE--------------------AASSSSTLVEVT  49
A6 (SEQ ID NO: 6)  KPEEGLEARGEALGLVGAQAPATEEQE--------------------AASSSSTLVEVT  49
A4 (SEQ ID NO: 4)  KPEEGVEAQEEALGLVGAQAPTTEEQEA-------------------AVSSSSPLVPGT  50
A5 (SEQ ID NO: 5)  KPEEGLDTQEEALGLVGVQAATTEEQE--------------------AVSSSSPLVPGT  49
A1 (SEQ ID NO: 1)  KPEEALEAQQEALGLVCVQAATS----------------------------SSSPLVLGT  42
A11(SEQ ID NO:10)  KPEEGLQAQEEDLGLVGAQALQAEEQE--------------------AAFFSSTLNVGT 159
A8 (SEQ ID NO: 7)  KAEEGLQAQGEAPGLMDVQIPTAEEQK--------------------AASSSSTLIMGT  49
A9 (SEQ ID NO: 8)  KPDEDLEAQGEDLGLMGAQEPTGEEEE--------------------TTSSSD----SK  45
A10(SEQ ID NO: 9)  MPEEDLQSQSETQGLEGAQAPLAVEEDASSSTSTSSSFPSSFPSSSSSSSSSCYPLIPST  70

A2 (SEQ ID NO: 2)  LGEVPAA-DSPSPPHSPQGASSFSTTINYTLWRQSDEGSSNQEEEGPRMFP---DLESEF 105
A12(SEQ ID NO:11)  LREVPAA-ESPSPPHSPQGASTLPTTINYTLWSQSDEGSSNEEQEGPSTFP---DLETSF 105
A3 (SEQ ID NO: 3)  LGEVPAA-ESPDPPQSPQGASSLPTTMNYPLWSQSYEDSSNQEEEGPSTFP---DLESEF 105
A6 (SEQ ID NO: 6)  LGEVPAA-ESPDPPQSPQGASSLPTTMNYPLWSQSYEDSSNQEEEGPSTFP---DLESEF 105
A4 (SEQ ID NO: 4)  LEEVPAA-ESAGPPQSPQGASALPTTISFTCWRQPNEGSSSQEEEGPSTSP---DAESLF 106
A5 (SEQ ID NO: 5)  LGEVPAA-GSPGPLKSPQGASAIPTAIDFTLWRQSIKGSSNQEEEGPSTSP---DPESVF 105
A1 (SEQ ID NO: 1)  LEEVPTA-GSTDPPQSPQGASAFPTTINFTRQRQPSEGSSSREEEGPSTSC---ILESLF  98
A11(SEQ ID NO:10)  LEELPAA-ESPSPPQSPQEESFSPTAMDAIFGSLSDEGSGSQEKEGPSTSPDLIDPESFS 218
A8 (SEQ ID NO: 7)  LEEVTDS-GSPSPPQSPEGASSSLTVTDSTLWSQSDEGSSSNEEEGPSTSPDPAHLESLF 108
A9 (SEQ ID NO: 8)  EEEVSAA-GSSSPPQSPQGGASSSISVYYTLWSQFDEGSSSQEEEEPSSSVDPAQLEFMF 104
A10(SEQ ID NO: 9)  PEEVSADDETPNPPQSAQIACSSPSVVASLPLDQSDEGSSSQKEESPSTLQVLPDSESLP 130
```

Figure 1, continued

```
A2(SEQ ID NO: 2)   QAAISRKMVELVHFLLLKYRAREPVTKAEMLESVLRNCQDFFPVIFSKASEYLQLVFGIE 165
A12(SEQ ID NO:11)  QVALSRKMAELVHFLLLKYRAREPFTKAEMLGSVIRNFQDFFPVIFSKASEYLQLVFGIE 165
A3(SEQ ID NO: 3)   QAALSRKVAELVHFLLLKYRAREPVTKAEMLGSVVGNWQYFFPVIFSKASSSLQLVFGIE 165
A6(SEQ ID NO: 6)   QAALSRKVAKLVHFLLLKYRAREPVTKAEMLGSVVGNWQYFFPVIFSKASDSLQLVFGIE 165
A4(SEQ ID NO: 4)   REALSNKVDELAHFLLRKYRAKELVTKAEMLERVIKNYKRCFPVIFGKASESLKMIFGID 166
A5(SEQ ID NO: 5)   RAALSKKVADLIHFLLLKY------------------------------------------ 124
A1(SEQ ID NO: 1)   RAVITKKVADLVGFLLLKYRAREPVTKAEMLESVIKNYKHCFPEIFGKASESLQLVFGID 158
A11(SEQ ID NO:10)  QDILHDKIIDLVHLLLRKYRVKGLITKAEMLGSVIKNYEDYFPEIFREASVCMQLLFGID 278
A8(SEQ ID NO: 7)   REALDEKVAELVRFLLRKYQIKEPVTKAEMLESVIKNYKNHFPDIFSKASECMQVIFGID 168
A9(SEQ ID NO: 8)   QEALKLKVAELVHFLLHKYRVKEPVTKAEMLESVIKNYKRYFPVIFGKASEFMQVIFGTD 164
A10(SEQ ID NO: 9)  RSEIDEKVTDLVQFLLFKYQMKEPITKAEILESVIKNYEDHFPLLFSEASECMLLVFGID 190

A2(SEQ ID NO: 2)   VVEVVPISHLYILVTCLGLSYDGLLGDNQVMPKTGLLIIVLAIIAIEGDCAPEEKIWEEL 225
A12(SEQ ID NO:11)  VVEVVRIGHLYILVTCLGLSYDGLLGDNQIVPKTGLLIIVLAIIAKEGDCAPEEKIWEEL 225
A3(SEQ ID NO: 3)   LMEVDPIGHLYIFATCLGLSYDGLLGDNQIMPKAGLLIIVLAIIAREGDCAPEEKIWEEL 225
A6(SEQ ID NO: 6)   LMEVDPIGHVYIFATCLGLSYDGLLGDNQIMPKTGFLIIILAIIAKEGDCAPEEKIWEEL 225
A4(SEQ ID NO: 4)   VKEVDPASNTYTLVTCLGLSYDGLLGNNQIFPKTGLLIIVLGTIAMEGDSASEEEIWEEL 226
A5(SEQ ID NO: 5)   ------------------------------------------------------------
A1(SEQ ID NO: 1)   VKEADPTGHSYVLVTCLGLSYDGLLGDNQIMPKTGFLIIVLVMIAMEGGHAPEEEIWEEL 218
A11(SEQ ID NO:10)  VKEVDPTSHSYVLVTSLNLSYDGIQCNEQSMPKSGLLIIVLGVIFMEGNCIPEEVMWEVL 338
A8(SEQ ID NO: 7)   VKEVDPAGHSYILVTCLGLSYDGLLGDDQSTPKTGLLIIVLGMILMEGSRAPEEAIWEAL 228
A9(SEQ ID NO: 8)   VKEVDPAGHSYILVTALGLSCDSMLGDGHSMPKAALLIIVLGVILTKDNCAPEEVIWEAL 224
A10(SEQ ID NO: 9)  VKEVDPTGHSFVLVTSLGLTYDGMLSDVQSMPKTGILILILSIIFIEGYCTPEEVIWEAL 250

A2(SEQ ID NO: 2)   SMLEVFEGREDSVFAHPRKLLMQDLVQENYLEYRQVPGSDPACYEFLWGPRALIETSYVK 285
A12(SEQ ID NO:11)  SVLEASDGREDSVFAHPRKLLTQDLVQENYLEYRQVPGSDPACYEFLWGPRALVETSYVK 285
A3(SEQ ID NO: 3)   SVLEVFEGREDSILGDPKKLLTQHFVQENYLEYRQVPGSDPACYEFLWGPRALVETSYVK 285
A6(SEQ ID NO: 6)   SVLEVFEGREDSIFGDPKKLLTQYFVQENYLEYRQVPGSDPACYEFLWGPRALIETSNVK 285
A4(SEQ ID NO: 4)   GVMGVYDGREHTVYGEPRKLLTQDWVQENYLEYRQVPGSNPARYEFLWGPRALAETSYVK 286
A5(SEQ ID NO: 5)   ------------------------------------------------------------
A1(SEQ ID NO: 1)   SVMEVYDGREHSAYGEPRKLLTQDLVQEKYLEYRQVPDSDPARYEFLWGPRALAETSYVK 278
A11(SEQ ID NO:10)  SIMGVYAGREHFLFGEPKRLLTQNWVQEKYLVYRQVPGTDPACYEFLWGPRAHAETSKMK 398
A8(SEQ ID NO: 7)   SVMGLYDGREHSVYWKLRKLLTQEWVQENYLEYRQAPGSDPVRYEFLWGPRALAETSYVK 288
A9(SEQ ID NO: 8)   SVMGVYVGKEHMFYGEPRKLLTQDWVQENYLEYRQVPGSDPAHYEFLWGSKAHAETSYEK 284
A10(SEQ ID NO: 9)  NMMGLYDGMEHLIYGEPRKLLTQDWVQENYLEYRQVPGSDPARYEFLWGPRAHAEIRKMS 310

A2(SEQ ID NO: 2)   VLHHTLKIGGEPHISYPPLHERALREGEE------------------------------ 314
A12(SEQ ID NO:11)  VLHHLLKISGGPHISYPPLHEWAFREGEE------------------------------ 314
A3(SEQ ID NO: 3)   VLHHMVKISGGPHISYPPLHEWVLREGEE------------------------------ 314
A6(SEQ ID NO: 6)   VLHHMVKISGGPRISYPLLHEWALREGEE------------------------------ 314
A4(SEQ ID NO: 4)   VLEHVVRVNARVRIAYPSLREAALLEEEEGV--------------------------- 317
A5(SEQ ID NO: 5)   ------------------------------------------------------------
A1(SEQ ID NO: 1)   VLEYVIKVSARVRFFFPSLREAALREEEEGV--------------------------- 309
A11(SEQ ID NO:10)  VLEYIANANGRDPTSYPSLYEDALREEGEGV--------------------------- 429
A8(SEQ ID NO: 7)   VLEHVVRVNARVRISYPSLHEEALGEEK-GV--------------------------- 318
A9(SEQ ID NO: 8)   VINYLVMLNAREPICYPSLYEEVLGEEQEGV--------------------------- 315
A10(SEQ ID NO: 9)  LLKFLAKVNGSDPRSFPLWYEEALKDEEERAQDRIATTDDTTAMASASSSATGSFSYPE 369
```

Figure 2

```
MAGE-A1      (59)  QGASAFPTTINFTRQRQPSEGSSSRE     (SEQ ID NO:12)
MAGE-A12     (66)  QGASTLPTTINYTLWSQSDEGSSNEE     (SEQ ID NO:13)
MAGE-A2      (66)  QGASSFSTTINYTLWRQSDEGSSNQE     (SEQ ID NO:14)
MAGE-A3      (66)  QGASSLPTTMNYPLWSQSYEDSSNQE     (SEQ ID NO:15)
MAGE-A6      (66)  QGASSLPTTMNYPLWSQSYEDSSNQE     (SEQ ID NO:16)
MAGE-A4      (67)  QGASALPTTISFTCWRQPNEGSSSQE     (SEQ ID NO:17)
MAGE-A5      (66)  QGASAIPTAIDFTLWRQSIKGSSNQE     (SEQ ID NO:18)
MAGE-A8      (66)  EGASSSLTVTDSTLWSQSDEGSSSNE     (SEQ ID NO:19)
MAGE-A10     (88)  QIACSSPSVVASLPLDQSDEGSSSQK     (SEQ ID NO:20)
MAGE-A11    (147)  QEESFSPTAMDAIFGSLSDEGSGSQE     (SEQ ID NO:21)
MAGE- A9     (62)  QGGASSISVYTLWSQFDEGSSSQE       (SEQ ID NO:22)
Consensus   (170)  QGASS  PTTI  YTLWSQSDEGSSSQE   (SEQ ID NO:23)
```

Figure 3

```
MAGE-A1     (130)  ESVIKNYKHCFPEIFGKASESLQLVFGIDVKEADPTGHSYVLVT   (SEQ ID NO:24)
MAGE-A12    (137)  GSVIRNFQDFFPVIFSKASEYLQLVFGIEVEVVRIGHLYILVT    (SEQ ID NO:25)
MAGE-A2     (137)  ESVLRNCQDFFPVIFSKASEYLQLVFGIEVEVVPISHLYILVT    (SEQ ID NO:26)
MAGE-A3     (137)  GSVVGNWQYFFPVIFPVIFSKASSSLQLVFGIELMEVDPIGHLYIFAT (SEQ ID NO:27)
MAGE-A6     (137)  GSVVGNWQYFFPVIFSKASDSLQLVFGIELMEVDPIGHVYIFAT   (SEQ ID NO:28)
MAGE-A4     (138)  ERVIKNYKRCFPVIFGKASESLKMIFGIDVKEVDPASNTYTLVT   (SEQ ID NO:29)
MAGE-A5     (125)  ----------------------------------------       
MAGE-A8     (140)  ESVIKNYKNHFPDIFSKASECMQVIFGIDVKEVDPAGHSYILVT   (SEQ ID NO:30)
MAGE-A10    (162)  ESVIKNYEDHFPLLFSEASECMLLVFGIDVKEVDPTGHSFVLVT   (SEQ ID NO:31)
MAGE-A11    (221)  GSVIKNYEDYFPEIFREASVCMQLLFGIDVKEVDPTSHSYVLVT   (SEQ ID NO:32)
MAGE- A9    (136)  ESVIKNYKRYFPVIFGKASEFMQVIFGTDVKEVDPAGHSYILVT   (SEQ ID NO:33)
Consensus   (244)  ESVIKNY   FFPVIFSKASE  LQLVFGIDVKEVDP GHSYILVT (SEQ ID NO:34)
```

Figure 10

| Sample Grade/Stage | RT-PCR MAGE-A3 | IHC mAb 23D2 Staining | IHC mAb 23D2 Intensity | RT-PCR MAGE-A4 | IHC mAb 57b Staining | IHC mAb 57b Intensity | RT-PCR MAGE-A9 | IHC mAb 14A11 Staining | IHC mAb 14A11 Intensity |
|---|---|---|---|---|---|---|---|---|---|
| Tum600 2/Ta | - | - | | - | - | | - | - | |
| Tum602 2/T1 | - | - | | - | - | | + | - | |
| Tum603 3/T1 | + | N.D. | | - | N.D. | | +++ | N.D. | |
| Tum604 3/T1 | - | - | | - | - | | + | - | |
| Tum605 2/T1 | + | - | | ++ | ++ | +/++ | +++ | + | + |
| Tum606 3/Ta | - | - | | - | - | | +++ | +++ | + |
| Tum607 2/T1 | - | - | | - | - | | +++ | - | |
| Tum608 2/T1 | - | - | | ++ | - | | ++ | ++ | ++ |
| Tum609 2/T1 | - | N.D. | | ++ | N.D. | | +++ | N.D. | |
| Tum611 2/T1 | ++ | - | | + | + | + | +++ | ++++ | + |
| Tum612 3/Ta | - | N.D. | | - | N.D. | | +++ | N.D. | |
| Tum613 3/T1 | +++ | N.D. | | +++ | + | +/++ | +++ | +++ | +/++ |
| Tum614 2/T1 | - | N.D. | | - | + | +/++ | +++ | +++ | +/++ |
| Tum615 3/T1 | - | - | | - | - | | + | - | |
| Tum616 1/Ta | + | + | + | ++ | +++ | | - | - | |
| Tum617 2/T1 | - | - | | ++ | + | | - | - | |
| Tum618 2/T1 | ++ | - | | - | - | | + | - | |
| Tum619 1/T1 | - | N.D. | | + | - | | +++ | +++ | + |
| Tum620 2/T1 | +++ | - | | +++ | ++++ | +/++ | +++ | + | +/++ |
| Tum621 3/T1 | - | + | +/++ | - | + | + | - | - | |
| Tum622 2/T1 | - | N.D. | | +++ | +++ | ++ | +++ | +++ | ++ |
| Tum623 2/Ta | - | - | | - | - | | - | - | |
| Tum624 2/Ta | + | N.D. | | + | + | + | +++ | ++++ | +/++ |
| Tum644 2/T1 | | | | | | | | | |
| Total Superficial Tumors | 7/24 (29%) | 2/17 (12%) | | 10/24 (42%) | 8/21 (38%) | | 17/24 (71%) | 10/21 (48%) | |

Figure 10 Continued

| Sample | | | | | | | | |
|---|---|---|---|---|---|---|---|---|
| Tum638 3/T3a | - | N.D. | | | N.D. | - | N.D. | |
| Tum639 3/T3a | +++ | N.D. | | | N.D. | ++ | N.D. | |
| Tum641 3/T3a | - | N.D. | | - | N.D. | - | N.D. | |
| Tum642 3/T3a | - | - | | - | + | ++ | + | + |
| Tum643 2/T4a | - | - | | - | - | ++ | +++ | + |
| Tum645 3/T3a | - | - | | - | - | - | - | |
| Tum646 3/T2b | - | [+] | + | - | + | + | ++ | + |
| Tum647 3/T3a | - | - | | - | - | - | - | |
| Tum649 3/T2 | - | - | | - | - | - | N.D. | |
| Tum650 2/T2 | - | - | | - | - | - | - | |
| Tum651 2/T4a | - | - | | - | - | - | - | |
| Tum652 3/T2a | - | [+] | + | - | - | - | N.D. | |
| Tum653 3/T4a | - | N.D. | | ++ | - | - | N.D. | |
| Tum654 3/T3a | ++ | N.D. | | - | - | ++ | N.D. | |
| Tum655 3/T2b | - | [+] | | - | - | - | - | |
| Tum656 3/T3a | - | [+] | | - | - | - | - | |
| Tum657 3/T2 | - | - | | - | +/++ | - | - | |
| Tum658 3/T2 | ++ | [-] | | ++ | +/++ | - | - | ++/+++ |
| Tum659 2/T2 | - | - | + | ++ | +/++ | +++ | ++ | ++ |
| Tum660 2/T2 | ++ | ++ | | ++ | - | +++ | +++ | |
| Tum661 2/T3a | ++ | + | | + | - | + | +++ | |
| Tum662 3/T3 | - | N.D. | | - | N.D. | - | N.D. | |
| Total invasive | 5/22(23%) | 6/16(37%) | | 5/22(23%) | 5/15(33%) | 8/22(36%) | 5/15(33%) | |
| Total all tumors | 12/46(26%) | 8/33(24%) | | 15/46(33%) | 13/36(36%) | 25/46(54%) | 15/36(42%) | |

*Results of RT-PCR analysis shown as -, +, ++ or +++
**where – indicates 0%, + indicates 1-24%, ++ indicates 25-49%, +++ indicates 50-74%, ++++ indicates 75-100% of cells stained.
*** + indicates weak, ++ indicates moderate, +++ indicates strong; combination of two intensities may be observed in same tissue sample.
N.D. indicates Not Determined
Discrepancies between RT-PCR and IHC results are boxed.

Figure 11

1B1-VH: (SEQ ID NO:38)

GATGTGCAGC TTCAGGAGTC GGGACCTGGC CTGGTGAAAC CTTCTCAGTC TCTGTCCCTC ACGTGCACTG
TCACTGGCTA CTCAATCACC AGTGATTATG TCTGGAACTG GATCCGGCAG TTTCCAGGAA ACAAACTGGA
GTGGATGGGC TACATAGGCC ACAGTGGTAG AACCAGCTAC AACCCATCTC TCAAAAGTCG AATCTCTATC
ACTCGAGACA CATCCAAGAA CCAGTTCTTC CTGCAATTGA ACTCTGTGAC TAGTGAGGAC ACAGCCACAT
ATTACTGTGC AAGAGGGGGT AACAACGGGT TTGCTTACTG GGGCCAAGGG ACTCTGGTCA CTGTCTCTGC
AG

1B1-VL: (SEQ ID NO:40)

GACATTGTGA TGACACAGTC TCCATCCTCC CTGACTGTGA CAGCAGGAGA GAAGGTCACT ATGAGCTGCA
AGTCCAGTCA GAGTCTGTTA ACAGTGGAA ATCAAAGAA CTACTTGACC TGGTACCAGC AGAAACCAGG
GCAGCCTCCT AAACTGTTGA TCTACTGGAC ATCCACTAGG GATTCTGGGG TCCCTGATCG CTTCACAGGC
AGTGGATCTG GAACAGATTT CACTCTCACC ATCAGCAGTG TGCAGGCTGA AGACCTGGCA GTTTATTACT
GTCAGAATGA TTATAGTTAT CCTCCCACGT TCGGAGGGGG GACCAAGCTG GAAATAAAAC GGGCT

16G7-VH: (SEQ ID NO:42)

GAAGTGATGG TGGTGGAGTC TGGGGGAGGC TTAGTGAAGC CTGGAGGGTC CCTGAAACTC TCCTGTGCAG
CCTCTGGATT CACTTTCAGA ACCAATGCCA TGTCTTGGGT TCGCCAGACT CCGGAGAAGA GGCTGGAGTG
GGTCGCAACC ATTACTAGCG GTGGTGGTTC CACCTACTAT CCAGTCAGTG TGAAGGGGCG ATTCACAATC
TCCAGAGACA ATGCCAAGAA CACCCTGTAC CTGCAAATGA GCAGTCTGAG GTCTGAGGAC ACGGCCATAT
ATTACTGTGT AAGACAGGAC TACTTTGACT ACTGGGGCCA GGGCACCTTT GTCATAGTCT CCTCAG

16G7-VL: (SEQ ID NO:44)

CAGGCTGTTG TGACTCAGGA ATCTGCACTC ACCACATCAC CTGGTGAAAC AGTCACACTC ACTTGTCGCT
CAAGTACTGG GGCTGTTACA TCTACTAACT ATGCCAACTG GGTCCAAGAA AAACCTGATC ATTTATTCAC
TGGTCTAATA GGTGGTACTA ACAACCGAGC TCCAGGTGTT CCTGCCAGAT TCTCAGGCTC CCTGATTGGA
GACAAGGCTG CCCTCACCAT CACAGGGGCA CAGACTGAGG ATGAGGCAAT ATATTTCTGT GCTCTATGGT
ACAGCAACCA CTGGGTGTTC GGTGGAGGAA CCAAACTGAC TGTCCTAG

23D2-VH: (SEQ ID NO:46)

GACGTGAAGC TGGTGGAGTC TGGGGGAGGC TTAGTGAAGC CTGGAGGGTC CCTGAAAGTY TCCTGTGTAG
CCTCTGGATT CACTTTCAGT AGCTATACCA TGTCCTGGGT TCGCCAGACT CCGGAGAAGA GGCTGGAGTG
GGTCGCAACC ATTACTAGTG GTGGTGGTTC TTCCTACTAT CCAGACAGTG TGAAGGGCCG ATTCACCATC
TCCAGGGACA ATGCCAAGAA CACCCTGTAC CTGCAAATTA CCAGTCTGAA GTCTGAGGAC ACAGCCATGT
ATTACTGTAC AAGCGGGGGG GGGGTTTTAC TACGGCTTCC CCTCTTTGCC TACTGGGGCC AAGGCACCAC
TCTCACAGTC TCCTCAG

23D2-VL: (SEQ ID NO:48)

CAGGCTGTTG TGACTCAGGA ATCTGCACTC ACCACATCAC CTGGTGAAAC AGTCACACTC ACTTGTCGCT
CAAGTACTGG GGCTGTTACA GCTAGTAACT ATGCCAACTG GGTCCAAGAA AAACCAGATC ATTCATTCAC
TGGTCTAATA GGTGGTATCA ACAACCGAGC TCCAGGTGTT CCTGCCAGAT TCTCAGGCTC CCTGATTGGA
GACAAGGCTG CCCTCACCAT CACAGGGGCA CAGACTGAGG ATGAGGCAAT ATATTTCTGT GCTCTATGGT
ACAACAACCA CTGGGTGTTC GGTGGAGGAA CCAAACTGAC TGTCCTA

DVQLQESGPG LVKPSQSLSL TCTVTGYSIT SDYVWNWIRQ FPGNKLEWMG YIGHSGRTSY NPSLKSRISI
TRDTSKNQFF LQLNSVTSED TATYYCARGG NNGFAYWGQG TLVTVSA  (SEQ ID NO:39)

1B1-VL:

DIVMTQSPSS LTVTAGEKVT MSCKSSQSLL NSGNQKNYLT WYQQKPGQPP KLLIYWTSTR DSGVPDRFTG
SGSGTDFTLT ISSVQAEDLA VYYCQNDYSY PPTFGGGTKL EIKRA (SEQ ID NO:41)

16G7-VH:

EVMVVESGGG LVKPGGSLKL SCAASGFTFR TNAMSWVRQT PEKRLEWVAT ITSGGGSTYY PVSVKGRFTI
SRDNAKNTLY LQMSSLRSED TAIYYCVRQD YFDYWGQGTF VIVSS (SEQ ID NO:43)

16G7-VL:

QAVVTQESAL TTSPGETVTL TCRSSTGAVT STNYANWVQE KPDHLFTGLI GGTNNRAPGV PARFSGSLIG
DKAALTITGA QTEDEAIYFC ALWYSNHWVF GGGTKLTVL (SEQ ID NO:45)

23D2-VH:

DVKLVESGGG LVKPGGSLKV SCVASGFTFS SYTMSWVRQT PEKRLEWVAT ITSGGGSSYY PDSVKGRFTI
SRDNAKNTLY LQITSLKSED TAMYYCTSGG GVLLRLPLFA YWGQGTTLTV SS (SEQ ID NO:47)

23D2-VL:

QAVVTQESAL TTSPGETVTL TCRSSTGAVT ASNYANWVQE KPDHSFTGLI GGINNRAPGV PARFSGSLIG
DKAALTITGA QTEDEAIYFC ALWYNNHWVF GGGTKLTVL (SEQ ID NO:49)

SEQUENCE LISTING

<160> NUMBER OF SEQ ID NOS: 70

<210> SEQ ID NO 1
<211> LENGTH: 309
<212> TYPE: PRT
<213> ORGANISM: Homo sapiens

<400> SEQUENCE: 1

Met Ser Leu Glu Gln Arg Ser Leu His Cys Lys Pro Glu Glu Ala Leu
 1               5                  10                  15

Glu Ala Gln Gln Glu Ala Leu Gly Leu Val Cys Val Gln Ala Ala Thr
             20                  25                  30

Ser Ser Ser Ser Pro Leu Val Leu Gly Thr Leu Glu Glu Val Pro Thr
         35                  40                  45

Ala Gly Ser Thr Asp Pro Pro Gln Ser Pro Gln Gly Ala Ser Ala Phe
     50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser

```
                   85                  90                  95
Leu Phe Arg Ala Val Ile Thr Lys Lys Val Ala Asp Leu Val Gly Phe
                100                 105                 110

Leu Leu Leu Lys Tyr Arg Ala Arg Glu Pro Val Thr Lys Ala Glu Met
            115                 120                 125

Leu Glu Ser Val Ile Lys Asn Tyr Lys His Cys Phe Pro Glu Ile Phe
130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Phe Pro Ser Leu Arg Glu Ala Ala Leu Arg Glu
    290                 295                 300

Glu Glu Glu Gly Val
305

<210> SEQ ID NO 2
<211> LENGTH: 314
<212> TYPE: PRT
<213> ORGANISM: Homo sapiens

<400> SEQUENCE: 2

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Gln Thr Ala Ser Ser Ser Thr Leu Val Glu Val
        35                  40                  45

Thr Leu Gly Glu Val Pro Ala Ala Asp Ser Pro Ser Pro Pro His Ser
    50                  55                  60

Pro Gln Gly Ala Ser Ser Phe Ser Thr Thr Ile Asn Tyr Thr Leu Trp
65                  70                  75                  80

Arg Gln Ser Asp Glu Gly Ser Ser Asn Gln Glu Glu Gly Pro Arg
                85                  90                  95

Met Phe Pro Asp Leu Glu Ser Glu Phe Gln Ala Ala Ile Ser Arg Lys
                100                 105                 110

Met Val Glu Leu Val His Phe Leu Leu Leu Lys Tyr Arg Ala Arg Glu
            115                 120                 125

Pro Val Thr Lys Ala Glu Met Leu Glu Ser Val Leu Arg Asn Cys Gln
        130                 135                 140
```

```
Asp Phe Phe Pro Val Ile Phe Ser Lys Ala Ser Glu Tyr Leu Gln Leu
145                 150                 155                 160

Val Phe Gly Ile Glu Val Glu Val Val Pro Ile Ser His Leu Tyr
            165                 170                 175

Ile Leu Val Thr Cys Leu Gly Leu Ser Tyr Asp Gly Leu Leu Gly Asp
            180                 185                 190

Asn Gln Val Met Pro Lys Thr Gly Leu Leu Ile Ile Val Leu Ala Ile
        195                 200                 205

Ile Ala Ile Glu Gly Asp Cys Ala Pro Glu Gly Lys Ile Trp Glu Glu
    210                 215                 220

Leu Ser Met Leu Glu Val Phe Glu Gly Arg Glu Asp Ser Val Phe Ala
225                 230                 235                 240

His Pro Arg Lys Leu Leu Met Gln Asp Leu Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
            275                 280                 285

His Thr Leu Lys Ile Gly Gly Glu Pro His Ile Ser Tyr Pro Pro Leu
        290                 295                 300

His Glu Arg Ala Leu Arg Glu Gly Glu Glu
305                 310

<210> SEQ ID NO 3
<211> LENGTH: 314
<212> TYPE: PRT
<213> ORGANISM: Homo sapiens

<400> SEQUENCE: 3

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Ser Thr Leu Val Glu Val
            35                  40                  45

Thr Leu Gly Glu Val Pro Ala Ala Glu Ser Pro Asp Pro Pro Gln Ser
50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
        130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
            165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205
```

```
Ile Ala Arg Glu Gly Asp Cys Ala Pro Glu Lys Ile Trp Glu
    210                 215                 220
Leu Ser Val Leu Glu Val Phe Glu Gly Arg Glu Asp Ser Ile Leu Gly
225                 230                 235                 240
Asp Pro Lys Lys Leu Leu Thr Gln His Phe Val Gln Glu Asn Tyr Leu
                    245                 250                 255
Glu Tyr Arg Gln Val Pro Gly Ser Asp Pro Ala Cys Tyr Glu Phe Leu
                260                 265                 270
Trp Gly Pro Arg Ala Leu Val Glu Thr Ser Tyr Val Lys Val Leu His
            275                 280                 285
His Met Val Lys Ile Ser Gly Pro His Ile Ser Tyr Pro Pro Leu
290                 295                 300
His Glu Trp Val Leu Arg Glu Gly Glu Glu
305                 310
```

<210> SEQ ID NO 4
<211> LENGTH: 317
<212> TYPE: PRT
<213> ORGANISM: Homo sapiens

<400> SEQUENCE: 4

```
Met Ser Ser Glu Gln Lys Ser Gln His Cys Lys Pro Glu Glu Gly Val
1               5                   10                  15
Glu Ala Gln Glu Ala Leu Gly Leu Val Gly Ala Gln Ala Pro Thr
                20                  25                  30
Thr Glu Glu Gln Glu Ala Ala Val Ser Ser Ser Ser Pro Leu Val Pro
            35                  40                  45
Gly Thr Leu Glu Glu Val Pro Ala Ala Glu Ser Ala Gly Pro Pro Gln
50                  55                  60
Ser Pro Gln Gly Ala Ser Ala Leu Pro Thr Thr Ile Ser Phe Thr Cys
65                  70                  75                  80
Trp Arg Gln Pro Asn Glu Gly Ser Ser Ser Gln Glu Glu Glu Gly Pro
                85                  90                  95
Ser Thr Ser Pro Asp Ala Glu Ser Leu Phe Arg Glu Ala Leu Ser Asn
            100                 105                 110
Lys Val Asp Glu Leu Ala His Phe Leu Leu Arg Lys Tyr Arg Ala Lys
        115                 120                 125
Glu Leu Val Thr Lys Ala Glu Met Leu Glu Arg Val Ile Lys Asn Tyr
    130                 135                 140
Lys Arg Cys Phe Pro Val Ile Phe Gly Lys Ala Ser Glu Ser Leu Lys
145                 150                 155                 160
Met Ile Phe Gly Ile Asp Val Lys Glu Val Asp Pro Ala Ser Asn Thr
                165                 170                 175
Tyr Thr Leu Val Thr Cys Leu Gly Leu Ser Tyr Asp Gly Leu Leu Gly
            180                 185                 190
Asn Asn Gln Ile Phe Pro Lys Thr Gly Leu Leu Ile Ile Val Leu Gly
        195                 200                 205
Thr Ile Ala Met Glu Gly Asp Ser Ala Ser Glu Glu Glu Ile Trp Glu
    210                 215                 220
Glu Leu Gly Val Met Gly Val Tyr Asp Gly Arg Glu His Thr Val Tyr
225                 230                 235                 240
Gly Glu Pro Arg Lys Leu Leu Thr Gln Asp Trp Val Gln Glu Asn Tyr
                245                 250                 255
Leu Glu Tyr Arg Gln Val Pro Gly Ser Asn Pro Ala Arg Tyr Glu Phe
```

```
              260                 265                 270
Leu Trp Gly Pro Arg Ala Leu Ala Glu Thr Ser Tyr Val Lys Val Leu
            275                 280                 285

Glu His Val Val Arg Val Asn Ala Arg Val Arg Ile Ala Tyr Pro Ser
        290                 295                 300

Leu Arg Glu Ala Ala Leu Glu Glu Glu Gly Val
305                 310                 315

<210> SEQ ID NO 5
<211> LENGTH: 124
<212> TYPE: PRT
<213> ORGANISM: Homo sapiens

<400> SEQUENCE: 5

Met Ser Leu Glu Gln Lys Ser Gln His Cys Lys Pro Glu Glu Gly Leu
1               5                   10                  15

Asp Thr Gln Glu Glu Ala Leu Gly Leu Val Gly Val Gln Ala Ala Thr
            20                  25                  30

Thr Glu Glu Gln Glu Ala Val Ser Ser Ser Pro Leu Val Pro Gly
        35                  40                  45

Thr Leu Gly Glu Val Pro Ala Ala Gly Ser Pro Gly Pro Leu Lys Ser
    50                  55                  60

Pro Gln Gly Ala Ser Ala Ile Pro Thr Ala Ile Asp Phe Thr Leu Trp
65                  70                  75                  80

Arg Gln Ser Ile Lys Gly Ser Ser Asn Gln Glu Glu Glu Gly Pro Ser
                85                  90                  95

Thr Ser Pro Asp Pro Glu Ser Val Phe Arg Ala Ala Leu Ser Lys Lys
            100                 105                 110

Val Ala Asp Leu Ile His Phe Leu Leu Leu Lys Tyr
        115                 120

<210> SEQ ID NO 6
<211> LENGTH: 314
<212> TYPE: PRT
<213> ORGANISM: Homo sapiens

<400> SEQUENCE: 6

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Lys Leu Val His Phe Leu Leu Leu Lys Tyr Arg Ala Arg Glu
        115                 120                 125

Pro Val Thr Lys Ala Glu Met Leu Gly Ser Val Gly Asn Trp Gln
    130                 135                 140

Tyr Phe Phe Pro Val Ile Phe Ser Lys Ala Ser Asp Ser Leu Gln Leu
```

```
                145                 150                 155                 160
Val Phe Gly Ile Glu Leu Met Glu Val Asp Pro Ile Gly His Val Tyr
                165                 170                 175

Ile Phe Ala Thr Cys Leu Gly Leu Ser Tyr Asp Gly Leu Leu Gly Asp
                180                 185                 190

Asn Gln Ile Met Pro Lys Thr Gly Phe Leu Ile Ile Leu Ala Ile
                195                 200                 205

Ile Ala Lys Glu Gly Asp Cys Ala Pro Glu Lys Ile Trp Glu Glu
210                 215                 220

Leu Ser Val Leu Glu Val Phe Glu Gly Arg Glu Asp Ser Ile Phe Gly
225                 230                 235                 240

Asp Pro Lys Lys Leu Leu Thr Gln Tyr Phe Val Gln Glu Asn Tyr Leu
                245                 250                 255

Glu Tyr Arg Gln Val Pro Gly Ser Asp Pro Ala Cys Tyr Glu Phe Leu
                260                 265                 270

Trp Gly Pro Arg Ala Leu Ile Glu Thr Ser Asn Val Lys Val Leu His
                275                 280                 285

His Met Val Lys Ile Ser Gly Gly Pro Arg Ile Ser Tyr Pro Leu Leu
                290                 295                 300

His Glu Trp Ala Leu Arg Glu Gly Glu Glu
305                 310

<210> SEQ ID NO 7
<211> LENGTH: 318
<212> TYPE: PRT
<213> ORGANISM: Homo sapiens

<400> SEQUENCE: 7

Met Leu Leu Gly Gln Lys Ser Gln Arg Tyr Lys Ala Glu Glu Gly Leu
1               5                   10                  15

Gln Ala Gln Gly Glu Ala Pro Gly Leu Met Asp Val Gln Ile Pro Thr
                20                  25                  30

Ala Glu Glu Gln Lys Ala Ala Ser Ser Ser Thr Leu Ile Met Gly
                35                  40                  45

Thr Leu Glu Glu Val Thr Asp Ser Gly Ser Pro Ser Pro Gln Ser
50                  55                  60

Pro Glu Gly Ala Ser Ser Ser Leu Thr Val Thr Asp Ser Thr Leu Trp
65                  70                  75                  80

Ser Gln Ser Asp Glu Gly Ser Ser Asn Glu Glu Glu Gly Pro Ser
                85                  90                  95

Thr Ser Pro Asp Pro Ala His Leu Glu Ser Leu Phe Arg Glu Ala Leu
                100                 105                 110

Asp Glu Lys Val Ala Glu Leu Val Arg Phe Leu Leu Arg Lys Tyr Gln
                115                 120                 125

Ile Lys Glu Pro Val Thr Lys Ala Glu Met Leu Glu Ser Val Ile Lys
130                 135                 140

Asn Tyr Lys Asn His Phe Pro Asp Ile Phe Ser Lys Ala Ser Glu Cys
145                 150                 155                 160

Met Gln Val Ile Phe Gly Ile Asp Val Lys Glu Val Asp Pro Ala Gly
                165                 170                 175

His Ser Tyr Ile Leu Val Thr Cys Leu Gly Leu Ser Tyr Asp Gly Leu
                180                 185                 190

Leu Gly Asp Asp Gln Ser Thr Pro Lys Thr Gly Leu Leu Ile Ile Val
                195                 200                 205
```

```
Leu Gly Met Ile Leu Met Glu Gly Ser Arg Ala Pro Glu Glu Ala Ile
    210                 215                 220

Trp Glu Ala Leu Ser Val Met Gly Leu Tyr Asp Gly Arg Glu His Ser
225                 230                 235                 240

Val Tyr Trp Lys Leu Arg Lys Leu Leu Thr Gln Glu Trp Val Gln Glu
                245                 250                 255

Asn Tyr Leu Glu Tyr Arg Gln Ala Pro Gly Ser Asp Pro Val Arg Tyr
            260                 265                 270

Glu Phe Leu Trp Gly Pro Arg Ala Leu Ala Glu Thr Ser Tyr Val Lys
        275                 280                 285

Val Leu Glu His Val Val Arg Val Asn Ala Arg Val Arg Ile Ser Tyr
    290                 295                 300

Pro Ser Leu His Glu Glu Ala Leu Gly Glu Glu Lys Gly Val
305                 310                 315

<210> SEQ ID NO 8
<211> LENGTH: 315
<212> TYPE: PRT
<213> ORGANISM: Homo sapiens

<400> SEQUENCE: 8

Met Ser Leu Glu Gln Arg Ser Pro His Cys Lys Pro Asp Glu Asp Leu
1               5                   10                  15

Glu Ala Gln Gly Glu Asp Leu Gly Leu Met Gly Ala Gln Glu Pro Thr
            20                  25                  30

Gly Glu Glu Glu Glu Thr Thr Ser Ser Asp Ser Lys Glu Glu Glu Glu
        35                  40                  45

Val Ser Ala Ala Gly Ser Ser Pro Pro Gln Ser Pro Gln Gly Gly
    50                  55                  60

Ala Ser Ser Ser Ile Ser Val Tyr Tyr Thr Leu Trp Ser Gln Phe Asp
65                  70                  75                  80

Glu Gly Ser Ser Ser Gln Glu Glu Glu Pro Ser Ser Ser Val Asp
                85                  90                  95

Pro Ala Gln Leu Glu Phe Met Phe Gln Glu Ala Leu Lys Leu Lys Val
            100                 105                 110

Ala Glu Leu Val His Phe Leu Leu His Lys Tyr Arg Val Lys Glu Pro
        115                 120                 125

Val Thr Lys Ala Glu Met Leu Glu Ser Val Ile Lys Asn Tyr Lys Arg
    130                 135                 140

Tyr Phe Pro Val Ile Phe Gly Lys Ala Ser Glu Phe Met Gln Val Ile
145                 150                 155                 160

Phe Gly Thr Asp Val Lys Glu Val Asp Pro Ala Gly His Ser Tyr Ile
                165                 170                 175

Leu Val Thr Ala Leu Gly Leu Ser Cys Asp Ser Met Leu Gly Asp Gly
            180                 185                 190

His Ser Met Pro Lys Ala Ala Leu Leu Ile Ile Val Leu Gly Val Ile
        195                 200                 205

Leu Thr Lys Asp Asn Cys Ala Pro Glu Glu Val Ile Trp Glu Ala Leu
    210                 215                 220

Ser Val Met Gly Val Tyr Val Gly Lys Glu His Met Phe Tyr Gly Glu
225                 230                 235                 240

Pro Arg Lys Leu Leu Thr Gln Asp Trp Val Gln Glu Asn Tyr Leu Glu
                245                 250                 255

Tyr Arg Gln Val Pro Gly Ser Asp Pro Ala His Tyr Glu Phe Leu Trp
            260                 265                 270
```

-continued

Gly Ser Lys Ala His Ala Glu Thr Ser Tyr Glu Lys Val Ile Asn Tyr
            275                 280                 285

Leu Val Met Leu Asn Ala Arg Glu Pro Ile Cys Tyr Pro Ser Leu Tyr
290                 295                 300

Glu Glu Val Leu Gly Glu Gln Glu Gly Val
305                 310                 315

<210> SEQ ID NO 9
<211> LENGTH: 369
<212> TYPE: PRT
<213> ORGANISM: Homo sapiens

<400> SEQUENCE: 9

Met Pro Arg Ala Pro Lys Arg Gln Arg Cys Met Pro Glu Glu Asp Leu
1               5                   10                  15

Gln Ser Gln Ser Glu Thr Gln Gly Leu Glu Gly Ala Gln Ala Pro Leu
            20                  25                  30

Ala Val Glu Glu Asp Ala Ser Ser Thr Ser Thr Ser Ser Ser Ser Phe
        35                  40                  45

Pro Ser Ser Phe Pro Ser Ser Ser Ser Ser Ser Ser Ser Ser Cys Tyr
50                  55                  60

Pro Leu Ile Pro Ser Thr Pro Glu Glu Val Ser Ala Asp Asp Glu Thr
65                  70                  75                  80

Pro Asn Pro Pro Gln Ser Ala Gln Ile Ala Cys Ser Ser Pro Ser Val
                85                  90                  95

Val Ala Ser Leu Pro Leu Asp Gln Ser Asp Glu Gly Ser Ser Ser Gln
            100                 105                 110

Lys Glu Glu Ser Pro Ser Thr Leu Gln Val Leu Pro Asp Ser Glu Ser
        115                 120                 125

Leu Pro Arg Ser Glu Ile Asp Glu Lys Val Thr Asp Leu Val Gln Phe
130                 135                 140

Leu Leu Phe Lys Tyr Gln Met Lys Glu Pro Ile Thr Lys Ala Glu Ile
145                 150                 155                 160

Leu Glu Ser Val Ile Lys Asn Tyr Glu Asp His Phe Pro Leu Leu Phe
                165                 170                 175

Ser Glu Ala Ser Glu Cys Met Leu Leu Val Phe Gly Ile Asp Val Lys
            180                 185                 190

Glu Val Asp Pro Thr Gly His Ser Phe Val Leu Val Thr Ser Leu Gly
        195                 200                 205

Leu Thr Tyr Asp Gly Met Leu Ser Asp Val Gln Ser Met Pro Lys Thr
210                 215                 220

Gly Ile Leu Ile Leu Ile Leu Ser Ile Ile Phe Ile Glu Gly Tyr Cys
225                 230                 235                 240

Thr Pro Glu Glu Val Ile Trp Glu Ala Leu Asn Met Met Gly Leu Tyr
                245                 250                 255

Asp Gly Met Glu His Leu Ile Tyr Gly Glu Pro Arg Lys Leu Leu Thr
            260                 265                 270

Gln Asp Trp Val Gln Glu Asn Tyr Leu Glu Tyr Arg Gln Val Pro Gly
        275                 280                 285

Ser Asp Pro Ala Arg Tyr Glu Phe Leu Trp Gly Pro Arg Ala His Ala
290                 295                 300

Glu Ile Arg Lys Met Ser Leu Leu Lys Phe Leu Ala Lys Val Asn Gly
305                 310                 315                 320

Ser Asp Pro Arg Ser Phe Pro Leu Trp Tyr Glu Glu Ala Leu Lys Asp

```
                   325                 330                 335
Glu Glu Glu Arg Ala Gln Asp Arg Ile Ala Thr Thr Asp Asp Thr Thr
                340                 345                 350

Ala Met Ala Ser Ala Ser Ser Ala Thr Gly Ser Phe Ser Tyr Pro
            355                 360                 365

Glu

<210> SEQ ID NO 10
<211> LENGTH: 429
<212> TYPE: PRT
<213> ORGANISM: Homo sapiens

<400> SEQUENCE: 10

Met Glu Thr Gln Phe Arg Arg Gly Gly Leu Gly Cys Ser Pro Ala Ser
1               5                   10                  15

Ile Lys Arg Lys Lys Arg Glu Asp Ser Gly Asp Phe Gly Leu Gln
            20                  25                  30

Val Ser Thr Met Phe Ser Glu Asp Asp Phe Gln Ser Thr Glu Arg Ala
            35                  40                  45

Pro Tyr Gly Pro Gln Leu Gln Trp Ser Gln Asp Leu Pro Arg Val Gln
        50                  55                  60

Val Phe Arg Glu Gln Ala Asn Leu Glu Asp Arg Ser Pro Arg Arg Thr
65              70                  75                  80

Gln Arg Ile Thr Gly Gly Glu Gln Val Leu Trp Gly Pro Ile Thr Gln
                85                  90                  95

Ile Phe Pro Thr Val Arg Pro Ala Asp Leu Thr Arg Val Ile Met Pro
            100                 105                 110

Leu Glu Gln Arg Ser Gln His Cys Lys Pro Glu Glu Gly Leu Gln Ala
        115                 120                 125

Gln Glu Glu Asp Leu Gly Leu Val Gly Ala Gln Ala Leu Gln Ala Glu
130                 135                 140

Glu Gln Glu Ala Ala Phe Phe Ser Ser Thr Leu Asn Val Gly Thr Leu
145                 150                 155                 160

Glu Glu Leu Pro Ala Ala Glu Ser Pro Ser Pro Gln Ser Pro Gln
                165                 170                 175

Glu Glu Ser Phe Ser Pro Thr Ala Met Asp Ala Ile Phe Gly Ser Leu
            180                 185                 190

Ser Asp Glu Gly Ser Gly Ser Gln Glu Lys Glu Gly Pro Ser Thr Ser
        195                 200                 205

Pro Asp Leu Ile Asp Pro Glu Ser Phe Ser Gln Asp Ile Leu His Asp
    210                 215                 220

Lys Ile Ile Asp Leu Val His Leu Leu Leu Arg Lys Tyr Arg Val Lys
225                 230                 235                 240

Gly Leu Ile Thr Lys Ala Glu Met Leu Gly Ser Val Ile Lys Asn Tyr
                245                 250                 255

Glu Asp Tyr Phe Pro Glu Ile Phe Arg Glu Ala Ser Val Cys Met Gln
            260                 265                 270

Leu Leu Phe Gly Ile Asp Val Lys Glu Val Asp Pro Thr Ser His Ser
        275                 280                 285

Tyr Val Leu Val Thr Ser Leu Asn Leu Ser Tyr Asp Gly Ile Gln Cys
    290                 295                 300

Asn Glu Gln Ser Met Pro Lys Ser Gly Leu Leu Ile Ile Val Leu Gly
305                 310                 315                 320

Val Ile Phe Met Glu Gly Asn Cys Ile Pro Glu Glu Val Met Trp Glu
```

```
            325                 330                 335
Val Leu Ser Ile Met Gly Val Tyr Ala Gly Arg Glu His Phe Leu Phe
            340                 345                 350

Gly Glu Pro Lys Arg Leu Leu Thr Gln Asn Trp Val Gln Glu Lys Tyr
            355                 360                 365

Leu Val Tyr Arg Gln Val Pro Gly Thr Asp Pro Ala Cys Tyr Glu Phe
        370                 375                 380

Leu Trp Gly Pro Arg Ala His Ala Glu Thr Ser Lys Met Lys Val Leu
385                 390                 395                 400

Glu Tyr Ile Ala Asn Ala Asn Gly Arg Asp Pro Thr Ser Tyr Pro Ser
                405                 410                 415

Leu Tyr Glu Asp Ala Leu Arg Glu Glu Gly Glu Gly Val
            420                 425

<210> SEQ ID NO 11
<211> LENGTH: 314
<212> TYPE: PRT
<213> ORGANISM: Homo sapiens

<400> SEQUENCE: 11

Met Pro Leu Glu Gln Arg Ser Gln His Cys Lys Pro Glu Glu Gly Leu
1               5                   10                  15

Glu Ala Gln Gly Glu Ala Leu Gly Leu Val Gly Ala Gln Ala Pro Ala
            20                  25                  30

Thr Glu Glu Gln Glu Thr Ala Ser Ser Ser Ser Thr Leu Val Glu Val
        35                  40                  45

Thr Leu Arg Glu Val Pro Ala Ala Glu Ser Pro Ser Pro Pro His Ser
    50                  55                  60

Pro Gln Gly Ala Ser Thr Leu Pro Thr Thr Ile Asn Tyr Thr Leu Trp
65                  70                  75                  80

Ser Gln Ser Asp Glu Gly Ser Ser Asn Glu Glu Gln Glu Gly Pro Ser
                85                  90                  95

Thr Phe Pro Asp Leu Glu Thr Ser Phe Gln Val Ala Leu Ser Arg Lys
            100                 105                 110

Met Ala Glu Leu Val His Phe Leu Leu Leu Lys Tyr Arg Ala Arg Glu
        115                 120                 125

Pro Phe Thr Lys Ala Glu Met Leu Gly Ser Val Ile Arg Asn Phe Gln
    130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Arg Ile Gly His Leu Tyr
                165                 170                 175

Ile Leu Val Thr Cys Leu Gly Leu Ser Tyr Asp Gly Leu Leu Gly Asp
            180                 185                 190

Asn Gln Ile Val Pro Lys Thr Gly Leu Leu Ile Ile Val Leu Ala Ile
        195                 200                 205

Ile Ala Lys Glu Gly Asp Cys Ala Pro Glu Glu Lys Ile Trp Glu Glu
    210                 215                 220

Leu Ser Val Leu Glu Ala Ser Asp Gly Arg Glu Asp Ser Val Phe Ala
225                 230                 235                 240

His Pro Arg Lys Leu Leu Thr Gln Asp Leu Val Gln Glu Asn Tyr Leu
                245                 250                 255

Glu Tyr Arg Gln Val Pro Gly Ser Asp Pro Ala Cys Tyr Glu Phe Leu
            260                 265                 270
```

```
Trp Gly Pro Arg Ala Leu Val Glu Thr Ser Tyr Val Lys Val Leu His
        275                 280                 285

His Leu Leu Lys Ile Ser Gly Gly Pro His Ile Ser Tyr Pro Pro Leu
    290                 295                 300

His Glu Trp Ala Phe Arg Glu Gly Glu Glu
305                 310

<210> SEQ ID NO 12
<211> LENGTH: 26
<212> TYPE: PRT
<213> ORGANISM: Artificial Sequence
<220> FEATURE:
<223> OTHER INFORMATION: Fragment of MAGE-A1

<400> SEQUENCE: 12

Gln Gly Ala Ser Ala Phe Pro Thr Thr Ile Asn Phe Thr Arg Gln Arg
1               5                   10                  15

Gln Pro Ser Glu Gly Ser Ser Ser Arg Glu
            20                  25

<210> SEQ ID NO 13
<211> LENGTH: 26
<212> TYPE: PRT
<213> ORGANISM: Artificial Sequence
<220> FEATURE:
<223> OTHER INFORMATION: Fragment of MAGE-A12

<400> SEQUENCE: 13

Gln Gly Ala Ser Thr Leu Pro Thr Thr Ile Asn Tyr Thr Leu Trp Ser
1               5                   10                  15

Gln Ser Asp Glu Gly Ser Ser Asn Glu Glu
            20                  25

<210> SEQ ID NO 14
<211> LENGTH: 26
<212> TYPE: PRT
<213> ORGANISM: Artificial Sequence
<220> FEATURE:
<223> OTHER INFORMATION: Fragment of MAGE-A2

<400> SEQUENCE: 14

Gln Gly Ala Ser Ser Phe Ser Thr Thr Ile Asn Tyr Thr Leu Trp Arg
1               5                   10                  15

Gln Ser Asp Glu Gly Ser Ser Asn Gln Glu
            20                  25

<210> SEQ ID NO 15
<211> LENGTH: 26
<212> TYPE: PRT
<213> ORGANISM: Artificial Sequence
<220> FEATURE:
<223> OTHER INFORMATION: Fragment of MAGE-A3

<400> SEQUENCE: 15

Gln Gly Ala Ser Ser Leu Pro Thr Thr Met Asn Tyr Pro Leu Trp Ser
1               5                   10                  15

Gln Ser Tyr Glu Asp Ser Ser Asn Gln Glu
            20                  25

<210> SEQ ID NO 16
<211> LENGTH: 26
<212> TYPE: PRT
<213> ORGANISM: Artificial Sequence
<220> FEATURE:
```

```
<223> OTHER INFORMATION: Fragment of MAGE-A6

<400> SEQUENCE: 16

Gln Gly Ala Ser Ser Leu Pro Thr Thr Met Asn Tyr Pro Leu Trp Ser
1               5                   10                  15

Gln Ser Tyr Glu Asp Ser Ser Asn Gln Glu
            20                  25

<210> SEQ ID NO 17
<211> LENGTH: 26
<212> TYPE: PRT
<213> ORGANISM: Artificial Sequence
<220> FEATURE:
<223> OTHER INFORMATION: Fragment of MAGE-A4

<400> SEQUENCE: 17

Gln Gly Ala Ser Ala Leu Pro Thr Thr Ile Ser Phe Thr Cys Trp Arg
1               5                   10                  15

Gln Pro Asn Glu Gly Ser Ser Ser Gln Glu
            20                  25

<210> SEQ ID NO 18
<211> LENGTH: 26
<212> TYPE: PRT
<213> ORGANISM: Artificial Sequence
<220> FEATURE:
<223> OTHER INFORMATION: Fragment of MAGE-A5

<400> SEQUENCE: 18

Gln Gly Ala Ser Ala Ile Pro Thr Ala Ile Asp Phe Thr Leu Trp Arg
1               5                   10                  15

Gln Ser Ile Lys Gly Ser Ser Asn Gln Glu
            20                  25

<210> SEQ ID NO 19
<211> LENGTH: 26
<212> TYPE: PRT
<213> ORGANISM: Artificial Sequence
<220> FEATURE:
<223> OTHER INFORMATION: Fragment of MAGE-A8

<400> SEQUENCE: 19

Glu Gly Ala Ser Ser Ser Leu Thr Val Thr Asp Ser Thr Leu Trp Ser
1               5                   10                  15

Gln Ser Asp Glu Gly Ser Ser Ser Asn Glu
            20                  25

<210> SEQ ID NO 20
<211> LENGTH: 26
<212> TYPE: PRT
<213> ORGANISM: Artificial Sequence
<220> FEATURE:
<223> OTHER INFORMATION: Fragment of MAGE-A10

<400> SEQUENCE: 20

Gln Ile Ala Cys Ser Ser Pro Ser Val Val Ala Ser Leu Pro Leu Asp
1               5                   10                  15

Gln Ser Asp Glu Gly Ser Ser Ser Gln Lys
            20                  25

<210> SEQ ID NO 21
<211> LENGTH: 26
<212> TYPE: PRT
<213> ORGANISM: Artificial Sequence
```

```
<220> FEATURE:
<223> OTHER INFORMATION: Fragment of MAGE-A11

<400> SEQUENCE: 21

Gln Glu Glu Ser Phe Ser Pro Thr Ala Met Asp Ala Ile Phe Gly Ser
1               5                   10                  15

Leu Ser Asp Glu Gly Ser Gly Ser Gln Glu
            20                  25

<210> SEQ ID NO 22
<211> LENGTH: 26
<212> TYPE: PRT
<213> ORGANISM: Artificial Sequence
<220> FEATURE:
<223> OTHER INFORMATION: Fragment of MAGE-A9

<400> SEQUENCE: 22

Gln Gly Gly Ala Ser Ser Ser Ile Ser Val Tyr Tyr Thr Leu Trp Ser
1               5                   10                  15

Gln Phe Asp Glu Gly Ser Ser Ser Gln Glu
            20                  25

<210> SEQ ID NO 23
<211> LENGTH: 24
<212> TYPE: PRT
<213> ORGANISM: Artificial Sequence
<220> FEATURE:
<223> OTHER INFORMATION: Consensus sequence of fragment of MAGE-A1, A2,
      A3, A4, A5, A6, A8, A9, A10, A11, A12 corresponding to amino acid
      residues 66-91 of MAGE-A3

<400> SEQUENCE: 23

Gln Gly Ala Ser Ser Pro Thr Thr Ile Tyr Thr Leu Trp Ser Gln Ser
1               5                   10                  15

Asp Glu Gly Ser Ser Ser Gln Glu
            20

<210> SEQ ID NO 24
<211> LENGTH: 44
<212> TYPE: PRT
<213> ORGANISM: Artificial Sequence
<220> FEATURE:
<223> OTHER INFORMATION: Fragment of MAGE-A1

<400> SEQUENCE: 24

Glu Ser Val Ile Lys Asn Tyr Lys His Cys Phe Pro Glu Ile Phe Gly
1               5                   10                  15

Lys Ala Ser Glu Ser Leu Gln Leu Val Phe Gly Ile Asp Val Lys Glu
            20                  25                  30

Ala Asp Pro Thr Gly His Ser Tyr Val Leu Val Thr
        35                  40

<210> SEQ ID NO 25
<211> LENGTH: 44
<212> TYPE: PRT
<213> ORGANISM: Artificial Sequence
<220> FEATURE:
<223> OTHER INFORMATION: Fragment of MAGE-A12

<400> SEQUENCE: 25

Gly Ser Val Ile Arg Asn Phe Gln Asp Phe Phe Pro Val Ile Phe Ser
1               5                   10                  15

Lys Ala Ser Glu Tyr Leu Gln Leu Val Phe Gly Ile Glu Val Val Glu
            20                  25                  30
```

```
Val Val Arg Ile Gly His Leu Tyr Ile Leu Val Thr
        35                  40
```

<210> SEQ ID NO 26
<211> LENGTH: 44
<212> TYPE: PRT
<213> ORGANISM: Artificial Sequence
<220> FEATURE:
<223> OTHER INFORMATION: Fragment of MAGE-A2

<400> SEQUENCE: 26

```
Glu Ser Val Leu Arg Asn Cys Gln Asp Phe Phe Pro Val Ile Phe Ser
1               5                   10                  15

Lys Ala Ser Glu Tyr Leu Gln Leu Val Phe Gly Ile Glu Val Val Glu
            20                  25                  30

Val Val Pro Ile Ser His Leu Tyr Ile Leu Val Thr
        35                  40
```

<210> SEQ ID NO 27
<211> LENGTH: 44
<212> TYPE: PRT
<213> ORGANISM: Artificial Sequence
<220> FEATURE:
<223> OTHER INFORMATION: Fragment of MAGE-A3

<400> SEQUENCE: 27

```
Gly Ser Val Val Gly Asn Trp Gln Tyr Phe Phe Pro Val Ile Phe Ser
1               5                   10                  15

Lys Ala Ser Ser Ser Leu Gln Leu Val Phe Gly Ile Glu Leu Met Glu
            20                  25                  30

Val Asp Pro Ile Gly His Leu Tyr Ile Phe Ala Thr
        35                  40
```

<210> SEQ ID NO 28
<211> LENGTH: 44
<212> TYPE: PRT
<213> ORGANISM: Artificial Sequence
<220> FEATURE:
<223> OTHER INFORMATION: Fragment of MAGE-A6

<400> SEQUENCE: 28

```
Gly Ser Val Val Gly Asn Trp Gln Tyr Phe Phe Pro Val Ile Phe Ser
1               5                   10                  15

Lys Ala Ser Asp Ser Leu Gln Leu Val Phe Gly Ile Glu Leu Met Glu
            20                  25                  30

Val Asp Pro Ile Gly His Val Tyr Ile Phe Ala Thr
        35                  40
```

<210> SEQ ID NO 29
<211> LENGTH: 44
<212> TYPE: PRT
<213> ORGANISM: Artificial Sequence
<220> FEATURE:
<223> OTHER INFORMATION: Fragment of MAGE-A4

<400> SEQUENCE: 29

```
Glu Arg Val Ile Lys Asn Tyr Lys Arg Cys Phe Pro Val Ile Phe Gly
1               5                   10                  15

Lys Ala Ser Glu Ser Leu Lys Met Ile Phe Gly Ile Asp Val Lys Glu
            20                  25                  30

Val Asp Pro Ala Ser Asn Thr Tyr Thr Leu Val Thr
        35                  40
```

```
<210> SEQ ID NO 30
<211> LENGTH: 44
<212> TYPE: PRT
<213> ORGANISM: Artificial Sequence
<220> FEATURE:
<223> OTHER INFORMATION: Fragment of MAGE-A8

<400> SEQUENCE: 30

Glu Ser Val Ile Lys Asn Tyr Lys Asn His Phe Pro Asp Ile Phe Ser
1               5                   10                  15

Lys Ala Ser Glu Cys Met Gln Val Ile Phe Gly Ile Asp Val Lys Glu
                20                  25                  30

Val Asp Pro Ala Gly His Ser Tyr Ile Leu Val Thr
        35                  40

<210> SEQ ID NO 31
<211> LENGTH: 44
<212> TYPE: PRT
<213> ORGANISM: Artificial Sequence
<220> FEATURE:
<223> OTHER INFORMATION: Fragment of MAGE-A10

<400> SEQUENCE: 31

Glu Ser Val Ile Lys Asn Tyr Glu Asp His Phe Pro Leu Leu Phe Ser
1               5                   10                  15

Glu Ala Ser Glu Cys Met Leu Leu Val Phe Gly Ile Asp Val Lys Glu
                20                  25                  30

Val Asp Pro Thr Gly His Ser Phe Val Leu Val Thr
        35                  40

<210> SEQ ID NO 32
<211> LENGTH: 44
<212> TYPE: PRT
<213> ORGANISM: Artificial Sequence
<220> FEATURE:
<223> OTHER INFORMATION: Fragment of MAGE-A11

<400> SEQUENCE: 32

Gly Ser Val Ile Lys Asn Tyr Glu Asp Tyr Phe Pro Glu Ile Phe Arg
1               5                   10                  15

Glu Ala Ser Val Cys Met Gln Leu Leu Phe Gly Ile Asp Val Lys Glu
                20                  25                  30

Val Asp Pro Thr Ser His Ser Tyr Val Leu Val Thr
        35                  40

<210> SEQ ID NO 33
<211> LENGTH: 44
<212> TYPE: PRT
<213> ORGANISM: Artificial Sequence
<220> FEATURE:
<223> OTHER INFORMATION: Fragment of MAGE-A9

<400> SEQUENCE: 33

Glu Ser Val Ile Lys Asn Tyr Lys Arg Tyr Phe Pro Val Ile Phe Gly
1               5                   10                  15

Lys Ala Ser Glu Phe Met Gln Val Ile Phe Gly Thr Asp Val Lys Glu
                20                  25                  30

Val Asp Pro Ala Gly His Ser Tyr Ile Leu Val Thr
        35                  40

<210> SEQ ID NO 34
```

-continued

```
<211> LENGTH: 40
<212> TYPE: PRT
<213> ORGANISM: Artificial Sequence
<220> FEATURE:
<223> OTHER INFORMATION: Consensus sequence of fragment of MAGE-A1, A12,
      A2, A3, A6, A4, A5, A8, A10, A11 and A9, at amino acid residues
      corresponding to amino acids 137-180 of MAGE A3

<400> SEQUENCE: 34

Glu Ser Val Ile Lys Asn Tyr Phe Phe Pro Val Ile Phe Ser Lys Ala
1               5                   10                  15

Ser Glu Leu Gln Leu Val Phe Gly Ile Asp Val Lys Glu Val Asp Pro
            20                  25                  30

Gly His Ser Tyr Ile Leu Val Thr
            35                  40

<210> SEQ ID NO 35
<211> LENGTH: 12
<212> TYPE: PRT
<213> ORGANISM: Artificial Sequence
<220> FEATURE:
<223> OTHER INFORMATION: Peptide derived from MAGE-A3 (MA3#1)

<400> SEQUENCE: 35

Cys Gly Ser Val Val Gly Asn Trp Gln Tyr Phe Phe
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Peptide derived from MAGE-A3 (MA3#2)

<400> SEQUENCE: 36

Cys Gly Ile Glu Leu Met Glu Val Asp Pro Ile Gly His Leu Tyr Phe
1               5                   10                  15

Ala Thr

<210> SEQ ID NO 37
<211> LENGTH: 20
<212> TYPE: PRT
<213> ORGANISM: Artificial Sequence
<220> FEATURE:
<223> OTHER INFORMATION: Peptide derived from MAGE-A3 (MA3#3)

<400> SEQUENCE: 37

Cys Gly Thr Thr Met Asn Tyr Pro Leu Trp Ser Gln Ser Tyr Glu Asp
1               5                   10                  15

Ser Ser Asn Gln
            20

<210> SEQ ID NO 38
<211> LENGTH: 352
<212> TYPE: DNA
<213> ORGANISM: Artificial Sequence
<220> FEATURE:
<223> OTHER INFORMATION: nucleotide sequence encoding mAb 1B1 heavy
      chain variable region
<220> FEATURE:
<221> NAME/KEY: CDS
<222> LOCATION: (1)..(351)

<400> SEQUENCE: 38 gat gtg cag ctt cag gag tcg gga cct ggc ctg gtg aaa cct tct cag      48
Asp Val Gln Leu Gln Glu Ser Gly Pro Gly Leu Val Lys Pro Ser Gln
```

```
                1               5                   10                  15
tct ctg tcc ctc acg tgc act gtc act ggc tac tca atc acc agt gat        96
Ser Leu Ser Leu Thr Cys Thr Val Thr Gly Tyr Ser Ile Thr Ser Asp
            20                      25                  30 tat gtc tgg aac tgg atc cgg cag ttt cca gga aac aaa ctg gag tgg       144
Tyr Val Trp Asn Trp Ile Arg Gln Phe Pro Gly Asn Lys Leu Glu Trp
        35                      40                  45 atg ggc tac ata ggc cac agt ggt aga acc agc tac aac cca tct ctc       192
Met Gly Tyr Ile Gly His Ser Gly Arg Thr Ser Tyr Asn Pro Ser Leu
    50                      55                  60 aaa agt cga atc tct atc act cga gac aca tcc aag aac cag ttc ttc       240
Lys Ser Arg Ile Ser Ile Thr Arg Asp Thr Ser Lys Asn Gln Phe Phe
65                      70                  75                  80 ctg caa ttg aac tct gtg act agt gag gac aca gcc aca tat tac tgt       288
Leu Gln Leu Asn Ser Val Thr Ser Glu Asp Thr Ala Thr Tyr Tyr Cys
                    85                  90                  95 gca aga ggg ggt aac aac ggg ttt gct tac tgg ggc caa ggg act ctg       336
Ala Arg Gly Gly Asn Asn Gly Phe Ala Tyr Trp Gly Gln Gly Thr Leu
                100                     105                 110 gtc act gtc tct gca g                                                 352
Val Thr Val Ser Ala
        115
```

<210> SEQ ID NO 39
<211> LENGTH: 117
<212> TYPE: PRT
<213> ORGANISM: Artificial Sequence
<220> FEATURE:
<223> OTHER INFORMATION: Synthetic Construct

<400> SEQUENCE: 39

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                      25                  30

Tyr Val Trp Asn Trp Ile Arg Gln Phe Pro Gly Asn Lys Leu Glu Trp
        35                      40                  45

Met Gly Tyr Ile Gly His Ser Gly Arg Thr Ser Tyr Asn Pro Ser Leu
    50                      55                  60

Lys Ser Arg Ile Ser Ile Thr Arg Asp Thr Ser Lys Asn Gln Phe Phe
65                      70                  75                  80

Leu Gln Leu Asn Ser Val Thr Ser Glu Asp Thr Ala Thr Tyr Tyr Cys
                    85                  90                  95

Ala Arg Gly Gly Asn Asn Gly Phe Ala Tyr Trp Gly Gln Gly Thr Leu
                100                     105                 110

Val Thr Val Ser Ala
        115
```

<210> SEQ ID NO 40
<211> LENGTH: 345
<212> TYPE: DNA
<213> ORGANISM: Artificial Sequence
<220> FEATURE:
<223> OTHER INFORMATION: Nucleotide sequence encoding mAb 1B1 light
      chain variable region
<220> FEATURE:
<221> NAME/KEY: CDS
<222> LOCATION: (1)..(345)

<400> SEQUENCE: 40

```
gac att gtg atg aca cag tct cca tcc tcc ctg act gtg aca gca gga        48
```

```
                 Asp Ile Val Met Thr Gln Ser Pro Ser Ser Leu Thr Val Thr Ala Gly
                 1               5                   10                  15 gag aag gtc act atg agc tgc aag tcc agt cag agt ctg tta aac agt         96
Glu Lys Val Thr Met Ser Cys Lys Ser Ser Gln Ser Leu Leu Asn Ser
                 20                  25                  30 gga aat caa aag aac tac ttg acc tgg tac cag cag aaa cca ggg cag        144
Gly Asn Gln Lys Asn Tyr Leu Thr Trp Tyr Gln Gln Lys Pro Gly Gln
             35                  40                  45 cct cct aaa ctg ttg atc tac tgg aca tcc act agg gat tct ggg gtc        192
Pro Pro Lys Leu Leu Ile Tyr Trp Thr Ser Thr Arg Asp Ser Gly Val
         50                  55                  60 cct gat cgc ttc aca ggc agt gga tct gga aca gat ttc act ctc acc        240
Pro Asp Arg Phe Thr Gly Ser Gly Ser Gly Thr Asp Phe Thr Leu Thr
 65                  70                  75                  80 atc agc agt gtg cag gct gaa gac ctg gca gtt tat tac tgt cag aat        288
Ile Ser Ser Val Gln Ala Glu Asp Leu Ala Val Tyr Tyr Cys Gln Asn
                 85                  90                  95 gat tat agt tat cct ccc acg ttc gga ggg ggg acc aag ctg gaa ata        336
Asp Tyr Ser Tyr Pro Pro Thr Phe Gly Gly Gly Thr Lys Leu Glu Ile
             100                 105                 110 aaa cgg gct                                                            345
Lys Arg Ala
         115

<210> SEQ ID NO 41
<211> LENGTH: 115
<212> TYPE: PRT
<213> ORGANISM: Artificial Sequence
<220> FEATURE:
<223> OTHER INFORMATION: Synthetic Construct

<400> SEQUENCE: 41

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Thr Ser Thr Arg Asp Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Pro Thr Phe Gly Gly Gly Thr Lys Leu Glu Ile
             100                 105                 110

Lys Arg Ala
         115

<210> SEQ ID NO 42
<211> LENGTH: 346
<212> TYPE: DNA
<213> ORGANISM: Artificial Sequence
<220> FEATURE:
<223> OTHER INFORMATION: Nucleotide sequence encoding mAb 16G7 variable
      heavy chain region
<220> FEATURE:
<221> NAME/KEY: CDS
<222> LOCATION: (1)..(345)

<400> SEQUENCE: 42
```

| | | | | | | | | | | | | | | | | |
|---|---|---|---|---|---|---|---|---|---|---|---|---|---|---|---|---|
| gaa | gtg | atg | gtg | gtg | gag | tct | ggg | gga | ggc | tta | gtg | aag | cct | gga | ggg | 48 |
| Glu | Val | Met | Val | Val | Glu | Ser | Gly | Gly | Gly | Leu | Val | Lys | Pro | Gly | Gly | |
| 1 | | | | 5 | | | | | 10 | | | | | 15 | | |
| tcc | ctg | aaa | ctc | tcc | tgt | gca | gcc | tct | gga | ttc | act | ttc | aga | acc | aat | 96 |
| Ser | Leu | Lys | Leu | Ser | Cys | Ala | Ala | Ser | Gly | Phe | Thr | Phe | Arg | Thr | Asn | |
| | | | 20 | | | | | 25 | | | | | 30 | | | |
| gcc | atg | tct | tgg | gtt | cgc | cag | act | ccg | gag | aag | agg | ctg | gag | tgg | gtc | 144 |
| Ala | Met | Ser | Trp | Val | Arg | Gln | Thr | Pro | Glu | Lys | Arg | Leu | Glu | Trp | Val | |
| | | 35 | | | | | 40 | | | | | 45 | | | | |
| gca | acc | att | act | agc | ggt | ggt | ggt | tcc | acc | tac | tat | cca | gtc | agt | gtg | 192 |
| Ala | Thr | Ile | Thr | Ser | Gly | Gly | Gly | Ser | Thr | Tyr | Tyr | Pro | Val | Ser | Val | |
| | 50 | | | | | 55 | | | | | 60 | | | | | |
| aag | ggg | cga | ttc | aca | atc | tcc | aga | gac | aat | gcc | aag | aac | acc | ctg | tac | 240 |
| Lys | Gly | Arg | Phe | Thr | Ile | Ser | Arg | Asp | Asn | Ala | Lys | Asn | Thr | Leu | Tyr | |
| 65 | | | | | 70 | | | | | 75 | | | | | 80 | |
| ctg | caa | atg | agc | agt | ctg | agg | tct | gag | gac | acg | gcc | ata | tat | tac | tgt | 288 |
| Leu | Gln | Met | Ser | Ser | Leu | Arg | Ser | Glu | Asp | Thr | Ala | Ile | Tyr | Tyr | Cys | |
| | | | 85 | | | | | 90 | | | | | 95 | | | |
| gta | aga | cag | gac | tac | ttt | gac | tac | tgg | ggc | cag | ggc | acc | ttt | gtc | ata | 336 |
| Val | Arg | Gln | Asp | Tyr | Phe | Asp | Tyr | Trp | Gly | Gln | Gly | Thr | Phe | Val | Ile | |
| | | 100 | | | | | 105 | | | | | 110 | | | | |
| gtc | tcc | tca | g | | | | | | | | | | | | | 346 |
| Val | Ser | Ser | | | | | | | | | | | | | | |
| | | 115 | | | | | | | | | | | | | | |

```
<210> SEQ ID NO 43
<211> LENGTH: 115
<212> TYPE: PRT
<213> ORGANISM: Artificial Sequence
<220> FEATURE:
<223> OTHER INFORMATION: Synthetic Construct

<400> SEQUENCE: 43
```

Glu Val Met Val Val Glu Ser Gly Gly Gly Leu Val Lys Pro Gly Gly
1               5                   10                  15

Ser Leu Lys Leu Ser Cys Ala Ala Ser Gly Phe Thr Phe Arg Thr Asn
            20                  25                  30

Ala Met Ser Trp Val Arg Gln Thr Pro Glu Lys Arg Leu Glu Trp Val
        35                  40                  45

Ala Thr Ile Thr Ser Gly Gly Gly Ser Thr Tyr Tyr Pro Val Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Ile Tyr Tyr Cys
                85                  90                  95

Val Arg Gln Asp Tyr Phe Asp Tyr Trp Gly Gln Gly Thr Phe Val Ile
            100                 105                 110

Val Ser Ser
        115

```
<210> SEQ ID NO 44
<211> LENGTH: 328
<212> TYPE: DNA
<213> ORGANISM: Artificial Sequence
<220> FEATURE:
<223> OTHER INFORMATION: Nucleotide sequence encoding mAb 16G7 variable
      light chain region
<220> FEATURE:
<221> NAME/KEY: CDS
<222> LOCATION: (1)..(327)

<400> SEQUENCE: 44
```

```
cag gct gtt gtg act cag gaa tct gca ctc acc aca tca cct ggt gaa        48
Gln Ala Val Val Thr Gln Glu Ser Ala Leu Thr Thr Ser Pro Gly Glu
1               5                   10                  15 aca gtc aca ctc act tgt cgc tca agt act ggg gct gtt aca tct act        96
Thr Val Thr Leu Thr Cys Arg Ser Ser Thr Gly Ala Val Thr Ser Thr
            20                  25                  30 aac tat gcc aac tgg gtc caa gaa aaa cct gat cat tta ttc act ggt       144
Asn Tyr Ala Asn Trp Val Gln Glu Lys Pro Asp His Leu Phe Thr Gly
        35                  40                  45 cta ata ggt ggt act aac aac cga gct cca ggt gtt cct gcc aga ttc       192
Leu Ile Gly Gly Thr Asn Asn Arg Ala Pro Gly Val Pro Ala Arg Phe
    50                  55                  60 tca ggc tcc ctg att gga gac aag gct gcc ctc acc atc aca ggg gca       240
Ser Gly Ser Leu Ile Gly Asp Lys Ala Ala Leu Thr Ile Thr Gly Ala
65                  70                  75                  80 cag act gag gat gag gca ata tat ttc tgt gct cta tgg tac agc aac       288
Gln Thr Glu Asp Glu Ala Ile Tyr Phe Cys Ala Leu Trp Tyr Ser Asn
                85                  90                  95 cac tgg gtg ttc ggt gga gga acc aaa ctg act gtc cta g                 328
His Trp Val Phe Gly Gly Gly Thr Lys Leu Thr Val Leu
                100                 105

<210> SEQ ID NO 45
<211> LENGTH: 109
<212> TYPE: PRT
<213> ORGANISM: Artificial Sequence
<220> FEATURE:
<223> OTHER INFORMATION: Synthetic Construct

<400> SEQUENCE: 45

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Ser Thr
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
                100                 105

<210> SEQ ID NO 46
<211> LENGTH: 367
<212> TYPE: DNA
<213> ORGANISM: Artificial Sequence
<220> FEATURE:
<223> OTHER INFORMATION: Nucleotide sequence encoding mAb 23D2 variable
      heavy chain region
<220> FEATURE:
<221> NAME/KEY: CDS
<222> LOCATION: (1)..(366)

<400> SEQUENCE: 46 gac gtg aag ctg gtg gag tct ggg gga ggc tta gtg aag cct gga ggg        48
Asp Val Lys Leu Val Glu Ser Gly Gly Gly Leu Val Lys Pro Gly Gly
1               5                   10                  15 tcc ctg aaa gty tcc tgt gta gcc tct gga ttc act ttc agt agc tat        96
```

```
Ser Leu Lys Xaa Ser Cys Val Ala Ser Gly Phe Thr Phe Ser Ser Tyr
            20                  25                  30 acc atg tcc tgg gtt cgc cag act ccg gag aag agg ctg gag tgg gtc    144
Thr Met Ser Trp Val Arg Gln Thr Pro Glu Lys Arg Leu Glu Trp Val
        35                  40                  45 gca acc att act agt ggt ggt ggt tct tcc tac tat cca gac agt gtg    192
Ala Thr Ile Thr Ser Gly Gly Gly Ser Ser Tyr Tyr Pro Asp Ser Val
 50                  55                  60 aag ggc cga ttc acc atc tcc agg gac aat gcc aag aac acc ctg tac    240
Lys Gly Arg Phe Thr Ile Ser Arg Asp Asn Ala Lys Asn Thr Leu Tyr
 65                  70                  75                  80 ctg caa att acc agt ctg aag tct gag gac aca gcc atg tat tac tgt    288
Leu Gln Ile Thr Ser Leu Lys Ser Glu Asp Thr Ala Met Tyr Tyr Cys
                85                  90                  95 aca agc ggg ggg ggg gtt tta cta cgg ctt ccc ctc ttt gcc tac tgg    336
Thr Ser Gly Gly Gly Val Leu Leu Arg Leu Pro Leu Phe Ala Tyr Trp
            100                 105                 110 ggc caa ggc acc act ctc aca gtc tcc tca g                          367
Gly Gln Gly Thr Thr Leu Thr Val Ser Ser
            115                 120
```

<210> SEQ ID NO 47
<211> LENGTH: 122
<212> TYPE: PRT
<213> ORGANISM: Artificial Sequence
<220> FEATURE:
<221> NAME/KEY: misc_feature
<222> LOCATION: (20)..(20)
<223> OTHER INFORMATION: The 'Xaa' at location 20 stands for Val.
<220> FEATURE:
<223> OTHER INFORMATION: Synthetic Construct

<400> SEQUENCE: 47

```
Asp Val Lys Leu Val Glu Ser Gly Gly Gly Leu Val Lys Pro Gly Gly
 1               5                  10                  15

Ser Leu Lys Xaa Ser Cys Val Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Thr Ser Gly Gly Gly Ser Ser Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Ile Thr Ser Leu Lys Ser Glu Asp Thr Ala Met Tyr Tyr Cys
                85                  90                  95

Thr Ser Gly Gly Gly Val Leu Leu Arg Leu Pro Leu Phe Ala Tyr Trp
            100                 105                 110

Gly Gln Gly Thr Thr Leu Thr Val Ser Ser
            115                 120
```

<210> SEQ ID NO 48
<211> LENGTH: 327
<212> TYPE: DNA
<213> ORGANISM: Artificial Sequence
<220> FEATURE:
<223> OTHER INFORMATION: Nucleotide sequence encoding mAb 23D2 variable
      light chain region
<220> FEATURE:
<221> NAME/KEY: CDS
<222> LOCATION: (1)..(327)

<400> SEQUENCE: 48

```
cag gct gtt gtg act cag gaa tct gca ctc acc aca tca cct ggt gaa      48
Gln Ala Val Val Thr Gln Glu Ser Ala Leu Thr Thr Ser Pro Gly Glu
 1               5                  10                  15 aca gtc aca ctc act tgt cgc tca agt act ggg gct gtt aca gct agt      96
Thr Val Thr Leu Thr Cys Arg Ser Ser Thr Gly Ala Val Thr Ala Ser
                 20                  25                  30 aac tat gcc aac tgg gtc caa gaa aaa cca gat cat tca ttc act ggt     144
Asn Tyr Ala Asn Trp Val Gln Glu Lys Pro Asp His Ser Phe Thr Gly
             35                  40                  45 cta ata ggt ggt atc aac aac cga gct cca ggt gtt cct gcc aga ttc     192
Leu Ile Gly Gly Ile Asn Asn Arg Ala Pro Gly Val Pro Ala Arg Phe
 50                  55                  60 tca ggc tcc ctg att gga gac aag gct gcc ctc acc atc aca ggg gca     240
Ser Gly Ser Leu Ile Gly Asp Lys Ala Ala Leu Thr Ile Thr Gly Ala
65                  70                  75                  80 cag act gag gat gag gca ata tat ttc tgt gct cta tgg tac aac aac     288
Gln Thr Glu Asp Glu Ala Ile Tyr Phe Cys Ala Leu Trp Tyr Asn Asn
                 85                  90                  95 cac tgg gtg ttc ggt gga gga acc aaa ctg act gtc cta                 327
His Trp Val Phe Gly Gly Gly Thr Lys Leu Thr Val Leu
            100                 105
```

<210> SEQ ID NO 49
<211> LENGTH: 109
<212> TYPE: PRT
<213> ORGANISM: Artificial Sequence
<220> FEATURE:
<223> OTHER INFORMATION: Synthetic Construct

<400> SEQUENCE: 49

```
Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Ala Ser
                 20                  25                  30

Asn Tyr Ala Asn Trp Val Gln Glu Lys Pro Asp His Ser Phe Thr Gly
             35                  40                  45

Leu Ile Gly Gly Ile Asn Asn Arg Ala Pro Gly Val Pro Ala Arg Phe
 50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Asn Asn
                 85                  90                  95

His Trp Val Phe Gly Gly Gly Thr Lys Leu Thr Val Leu
            100                 105
```

<210> SEQ ID NO 50
<211> LENGTH: 6
<212> TYPE: PRT
<213> ORGANISM: Artificial Sequence
<220> FEATURE:
<223> OTHER INFORMATION: CDRH1 of mAb 1B1

<400> SEQUENCE: 50

```
Ser Asp Tyr Val Trp Asn
 1               5
```

<210> SEQ ID NO 51
<211> LENGTH: 16
<212> TYPE: PRT
<213> ORGANISM: Artificial Sequence
<220> FEATURE:
<223> OTHER INFORMATION: CDRH2 of mAb 1B1

```
<400> SEQUENCE: 51

Tyr Ile Gly His Ser Gly Arg Thr Ser Tyr Asn Pro Ser Leu Lys Ser
1               5                   10                  15

<210> SEQ ID NO 52
<211> LENGTH: 8
<212> TYPE: PRT
<213> ORGANISM: Artificial Sequence
<220> FEATURE:
<223> OTHER INFORMATION: CDRH3 of mAb 1B1

<400> SEQUENCE: 52

Gly Gly Asn Asn Gly Phe Ala Tyr
1               5

<210> SEQ ID NO 53
<211> LENGTH: 17
<212> TYPE: PRT
<213> ORGANISM: Artificial Sequence
<220> FEATURE:
<223> OTHER INFORMATION: CDRL1 of mAb 1B1

<400> SEQUENCE: 53

Lys Ser Ser Gln Ser Leu Leu Asn Ser Gly Asn Gln Lys Asn Tyr Leu
1               5                   10                  15
Thr

<210> SEQ ID NO 54
<211> LENGTH: 7
<212> TYPE: PRT
<213> ORGANISM: Artificial Sequence
<220> FEATURE:
<223> OTHER INFORMATION: CDRL2 of mAb 1B1

<400> SEQUENCE: 54

Trp Thr Ser Thr Arg Asp Ser
1               5

<210> SEQ ID NO 55
<211> LENGTH: 9
<212> TYPE: PRT
<213> ORGANISM: Artificial Sequence
<220> FEATURE:
<223> OTHER INFORMATION: CDRL3 of mAb 1B1

<400> SEQUENCE: 55

Gln Asn Asp Tyr Ser Tyr Pro Pro Thr
1               5

<210> SEQ ID NO 56
<211> LENGTH: 5
<212> TYPE: PRT
<213> ORGANISM: Artificial Sequence
<220> FEATURE:
<223> OTHER INFORMATION: CDRH1 of mAb 16G7

<400> SEQUENCE: 56

Thr Asn Ala Met Ser
1               5

<210> SEQ ID NO 57
<211> LENGTH: 17
<212> TYPE: PRT
<213> ORGANISM: Artificial Sequence
<220> FEATURE:
```

<223> OTHER INFORMATION: CDRH2 of mAb 16G7

<400> SEQUENCE: 57

Thr Ile Thr Ser Gly Gly Gly Ser Thr Tyr Tyr Pro Val Ser Val Lys
1               5                   10                  15
Gly

<210> SEQ ID NO 58
<211> LENGTH: 6
<212> TYPE: PRT
<213> ORGANISM: Artificial Sequence
<220> FEATURE:
<223> OTHER INFORMATION: CDRH3 of mAb 16G7

<400> SEQUENCE: 58

Gln Asp Tyr Phe Asp Tyr
1               5

<210> SEQ ID NO 59
<211> LENGTH: 14
<212> TYPE: PRT
<213> ORGANISM: Artificial Sequence
<220> FEATURE:
<223> OTHER INFORMATION: CDRL1 of mAb 16G7

<400> SEQUENCE: 59

Arg Ser Ser Thr Gly Ala Val Thr Ser Thr Asn Tyr Ala Asn
1               5                   10

<210> SEQ ID NO 60
<211> LENGTH: 7
<212> TYPE: PRT
<213> ORGANISM: Artificial Sequence
<220> FEATURE:
<223> OTHER INFORMATION: CDRL2 of mAb 16G7

<400> SEQUENCE: 60

Gly Thr Asn Asn Arg Ala Pro
1               5

<210> SEQ ID NO 61
<211> LENGTH: 9
<212> TYPE: PRT
<213> ORGANISM: Artificial Sequence
<220> FEATURE:
<223> OTHER INFORMATION: CDRL3 of mAb 16G7

<400> SEQUENCE: 61

Ala Leu Trp Tyr Ser Asn His Trp Val
1               5

<210> SEQ ID NO 62
<211> LENGTH: 5
<212> TYPE: PRT
<213> ORGANISM: Artificial Sequence
<220> FEATURE:
<223> OTHER INFORMATION: CDRH1 of mAb 23D2

<400> SEQUENCE: 62

Ser Tyr Thr Met Ser
1               5

<210> SEQ ID NO 63
<211> LENGTH: 17
<212> TYPE: PRT
<213> ORGANISM: Artificial Sequence

```
<220> FEATURE:
<223> OTHER INFORMATION: CDRH2 of mAb 23D2

<400> SEQUENCE: 63

Thr Ile Thr Ser Gly Gly Ser Ser Tyr Tyr Pro Asp Ser Val Lys
1               5                   10                  15
Gly

<210> SEQ ID NO 64
<211> LENGTH: 13
<212> TYPE: PRT
<213> ORGANISM: Artificial Sequence
<220> FEATURE:
<223> OTHER INFORMATION: CDRH3 of mAb 23D2

<400> SEQUENCE: 64

Gly Gly Gly Val Leu Leu Arg Leu Pro Leu Phe Ala Tyr
1               5                   10

<210> SEQ ID NO 65
<211> LENGTH: 14
<212> TYPE: PRT
<213> ORGANISM: Artificial Sequence
<220> FEATURE:
<223> OTHER INFORMATION: CDRL1 of mAb 23D2

<400> SEQUENCE: 65

Arg Ser Ser Thr Gly Ala Val Thr Ala Ser Asn Tyr Ala Asn
1               5                   10

<210> SEQ ID NO 66
<211> LENGTH: 7
<212> TYPE: PRT
<213> ORGANISM: Artificial Sequence
<220> FEATURE:
<223> OTHER INFORMATION: CDRL2 of mAb 23D2

<400> SEQUENCE: 66

Gly Ile Asn Asn Arg Ala Pro
1               5

<210> SEQ ID NO 67
<211> LENGTH: 9
<212> TYPE: PRT
<213> ORGANISM: Artificial Sequence
<220> FEATURE:
<223> OTHER INFORMATION: CDRL3 of mAb 23D2

<400> SEQUENCE: 67

Ala Leu Trp Tyr Asn Asn His Trp Val
1               5

<210> SEQ ID NO 68
<211> LENGTH: 8
<212> TYPE: PRT
<213> ORGANISM: Artificial Sequence
<220> FEATURE:
<223> OTHER INFORMATION: variant CDRH3 for mAb 1B1

<400> SEQUENCE: 68

Gly Trp Asn Asn Gly Phe Ala Tyr
1               5

<210> SEQ ID NO 69
<211> LENGTH: 6
<212> TYPE: PRT
```

```
<213> ORGANISM: Artificial Sequence
<220> FEATURE:
<223> OTHER INFORMATION: 1B1 CDRH1 variant

<400> SEQUENCE: 69

Ser Asp Tyr Ala Trp Asn
1               5

<210> SEQ ID NO 70
<211> LENGTH: 16
<212> TYPE: PRT
<213> ORGANISM: Artificial Sequence
<220> FEATURE:
<223> OTHER INFORMATION: b CDRH2 variant

<400> SEQUENCE: 70

Tyr Asn Gly His Ser Gly Arg Thr Ser Tyr Asn Pro Ser Leu Lys Ser
1               5                   10                  15
```

US 8,987,423 B2

MAGE ANTIGEN BINDING PROTEINS

This application is filed pursuant to 35 U.S.C. §371 as United States National Phase Application of International Patent Application Serial No. PCT/EP2011/062458 filed Jul. 20, 2011, which claims priority to U.S. Application No. 61/366,742 filed Jul. 22, 2010, the contents of which are incorporated herein by reference.

FIELD OF INVENTION

The present invention relates to antigen binding proteins, such as antibodies, which bind to human MAGE-A3, polynucleotides encoding such antigen binding proteins, diagnostic applications of said antigen binding proteins and methods of manufacture.

BACKGROUND

"Cancer-testis" antigens are expressed in several types of tumours but their expression in normal tissues is restricted to testis, which cannot present antigens to T cells because they lack expression of MHC (major histocompatibility complex) class I molecules. Therefore, cancer-testis antigens are considered as tumour-specific antigens, and are potential targets for tumour immunotherapy. Human MAGE-A3 is known to be expressed frequently in a variety of human tumours including melanoma, non-small cell lung carcinoma (NSCLC), bladder cancer, head and neck cancers, squamous oesophageal cancer, and hepatocarcinoma.

MAGE-A3 belongs to the MAGE-A sub-family which comprises 11 known members (MAGEA 1-6 and 8-12). While other "MAGE A" (melanoma antigen family A) genes have been reported (such as MAGE A7, A13-15), the expression patterns of these genes suggest that they are pseudogenes (see e.g., Chomez et al., *Cancer Research*, 61:5544 (2001)). The 11 MAGE-A genes have their entire coding sequence located in the last exon.

The MAGE-A gene with the highest sequence similarity to the MAGE-A3 gene is MAGE-A6, which is 99% identical, and the differences between the two genes are located within the last exon. The two genes that are the next most closely related to MAGE-A3 are MAGE-A2 and MAGE-A12. At the protein level, MAGE-A6 has 95% sequence identity to MAGE-A3, MAGE-A2 has 84% sequence identity to MAGE-A3, and MAGE-A12 has 85% sequence identity to MAGE-A3. (FIG. 1)

MAGE-N is a new member of the MAGE family, identified from mRNA isolated from a human hepatocellular carcinoma cell line (Wu et al., *Chin. J. Cell Mol. Immunol.* 18:270-4 (2002)). MAGE-N has been reported to be closely associated with hepatocellular carcinoma (Dong et al., *Cancer Biol. Ther.* 3(9):891-8 (2004). At the predicted protein level, MAGE-N has <85% sequence similarity to MAGE-A3 and MAGE-A6. MAGE-N is possibly a combination of MAGE-A3, A12, and A1—where the N-terminal region of MAGE-N (amino acids 1-129) has 99% identity to the N-terminal region of MAGE-A3, the central region of MAGE-N differs by one amino acid compared to the central region of MAGE-A12, and the C-terminal region of MAGE-N is identical to the C-terminal region of MAGE-A1.

SUMMARY OF THE INVENTION

The present invention provides an antigen binding protein which specifically binds to MAGE-A3 and MAGE-A6.

The present invention provides an antigen binding protein which specifically binds to MAGE-A3 and MAGE-A6, but which does not bind, or does not specifically bind, to MAGE-A2 or MAGE-A12.

The present invention provides an antigen binding protein which specifically binds to MAGE-A3 and which comprises a CDRH3 selected from SEQ ID NOs: 52, 58 and 64, or a variant thereof.

The present invention provides an antigen binding protein which specifically binds to MAGE-A3 and comprises a CDRL3 selected from SEQ ID NOs:55, 61 and 67, or a variant thereof.

The present invention also provides an antigen binding protein which specifically binds to MAGE-A3 and comprises:

(i) a heavy chain variable region of SEQ ID NO: 47 and/or a light chain variable region of SEQ ID NO:49; or a variant heavy chain variable region with 75% or greater sequence identity to SEQ ID NO:47; or a light chain variable region with 75% or greater sequence identity to SEQ ID NO:49;

(ii) a heavy chain variable region of SEQ ID NO:39 and/or a light chain variable region of SEQ ID NO:41; or a variant heavy chain variable region with 75% or greater sequence identity to SEQ ID NO:39; or a light chain variable region with 75% or greater sequence identity to SEQ ID NO:41; or (iii) a heavy chain variable region of SEQ ID NO: 43; and/or a light chain variable region of SEQ ID NO:45; or a variant heavy chain variable region with 75% or greater sequence identity to SEQ ID NO:43; or a light chain variable region with 75% or greater sequence identity to SEQ ID NO:45.

The invention also provides a nucleic acid molecule which encodes an antigen binding protein as defined herein. The invention also provides an expression vector comprising a nucleic acid molecule as defined herein. The invention also provides a recombinant host cell comprising an expression vector as defined herein. The invention also provides a method for the production of an antigen binding protein as defined herein which method comprises the step of culturing a host cell as defined above and recovering the antigen binding protein.

The invention also provides a method of producing antigen binding proteins as described herein by immunization using divergent peptides of MAGE-A3.

The invention also provides a method of detecting MAGE-A3 and/or MAGE-A6 in human formalin-fixed paraffin embedded tissue using the antigen binding proteins as described herein.

The invention also provides a method of detecting MAGE-N in human formalin-fixed paraffin embedded tissue using the antigen binding proteins as described herein.

BRIEF DESCRIPTION OF THE FIGURES

FIG. 1: Sequence comparison of human MAGE-A1, A2, A3, A4, A5, A6, A8, A9, A10, A11, and A12.

FIG. 2: Comparison of MAGE-A3 fragments corresponding to amino acids 66-91 of MAGE-A3 (SEQ ID NO:3). The amino acids contained in peptide MA3#3 (SEQ ID NO: 37) are underlined.

FIG. 3: Comparison of MAGE-A3 fragments corresponding to amino acids 137-180 of MAGE-A3 (SEQ ID NO:3). The amino acids contained in peptide MA3#1 (SEQ ID NO:35) and MA3#2 (SEQ ID NO:36) are underlined.

FIG. 10: Table showing the IHC analysis of tumor samples using mAb 23D2 to detect MAGE-A3/A6, mAb 57b to detect MAGE-A4, and mAb 14A11 to detect MAGE-A9. Results of RT-PCR analysis shown as −, +, ++, +++. Results of IHC staining shown as −, +, ++, +++, ++++, indicating 0%, 1-24%, 25-49%, 50-74% and 75-100% of cells stained, respectively. Results of IHC intensity shown as + (weak), ++ (moderate), and +++ (strong); a combination of two staining intensities was observed in some tissue samples. N.D. indicates Not Determined. Discrepancies between RT-PCR and IHC results are boxed.

FIG. 11 shows the nucleotide sequences of the variable light and heavy chains of anti-MAGE-A3 monoclonal antibodies 1B1, 16G7, and 23D2.

FIG. 12 shows the amino acid sequences obtained from the nucleotide sequences of the variable light and heavy chains of anti-MAGE-A3 monoclonal antibodies 1B1, 16G7, and 23D2. CDRs are underlined; framework regions are not underlined.

DETAILED DESCRIPTION OF THE INVENTION

Figure 4A:
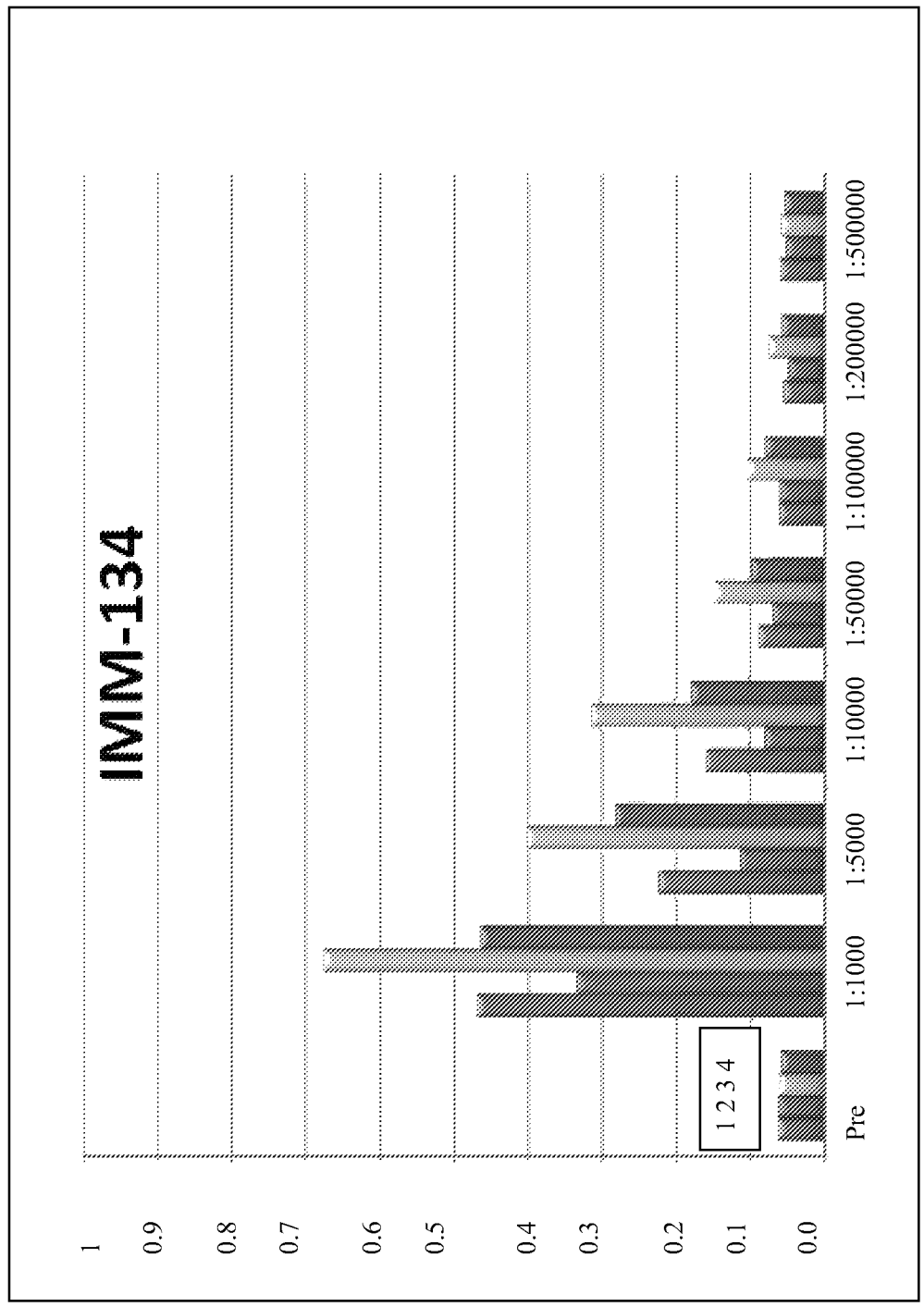
FIG. 4A: Graphs the relative anti-MAGE-A3 antibody titer in the serum of mice immunized with a mixture of three MAGE-A3 peptides conjugated to KLH (Protocol IMM-134). Pre-Immune sera (Pre) and serum dilutions from each of the four mice included in the protocol were tested in ELISA on the full-length recombinant MAGE-A3 protein (serum dilutions at 1:1000, 1:5000, 1:10,000, 1:50,000, 1:100,000, 1:200,000 and 1:500,000). The results for each dilution are given for mouse 1, 2, 3 and 4 in the order as indicated above the pre-immune (Pre) sera.

GlaxoSmithKline Biologicals S.A. is developing a MAGE-A3 Antigen-Specific Cancer Immunotherapeutic (ASCI) for the treatment of metastatic melanoma and NSCLC. This immunotherapeutic combines (a) a fusion protein comprising a fragment of MAGE-A3, with (b) an Adjuvant System which is a specific combination of immunostimulating compounds selected to increase the anti-tumour immune response. (Brichard et al., Vaccine 25(Suppl 2):B61 (2007)). Before enrolment into current clinical trials, patients are screened to determine whether they have a tumour expressing MAGE-A3. Currently, analysis of MAGE-A3 expression in tumours is performed by real time-polymerase chain reaction (RT-PCR). Detection by immunohistochemistry (IHC) using formalin-fixed and paraffin-embedded (FFPE) tumour tissue (archival tissue blocks) requires a reliable monoclonal antibody (mAb) specific to MAGE-A3 and able to detect the antigen in FFPE tissues. Due to the high sequence similarity of MAGE-A proteins, antibodies to MAGE-A3 may cross-react with other MAGE-A proteins. For example, Kocher et al. produced an anti-MAGE-A3 monoclonal antibody by immunizing mice with a recombinant MAGE-A3 protein (Kocher et al. Cancer Res, 55: 2236, 1995.). The resulting mAb (called 57B) was later shown to cross react with MAGE-A1, -A2, -A3, -A4, -A6 and -A12 (Rimoldi et al. Int J Cancer, 86: 749, 2000). A further analysis of the reactivity of the 57B mAb with formalin-fixed and paraffin-embedded tissues reported that it primarily detected MAGE-A4, as it was unreactive with tissues expressing other MAGE-A antigens regardless of their level of expression (Landry et al. Int J Cancer, 86: 835, 2000).

An analysis of the specificity of the anti-MAGE-A3 mAb 6D10 (Abnova, GeneTex and Novus Biologicals) showed that this mAb cross-reacted with MAGE-A2 and MAGE-A6 (unpublished data of the present applicant). In addition, use of this mAb in IHC (immunohistochemistry) analysis on formalin-fixed and paraffin-embedded tissues was unsuccessful (unpublished data of present applicant). Another mAb against MAGE-A3/A6 is known as mAb M3H67 (LICR New York, USA; see e.g., Sharma et al., *Clinical Cancer Research* 12:5442 (2006); Chitale et al., *Modern Pathology* 18:119 (2005)). This antibody has been used to characterize the expression of MAGE-A3/A6 in formalin-fixed and paraffin-embedded tissues but analysis of its specificity has not been published (see, for example, Chitale et al. Mod Pathol, 18: 119, 2005; Perez et al. Int J Cancer, 123: 1551, 2008; Oba-Shinjo et al. Cancer Immun, 8: 7, 2008; Nelson et al. Cancer Immun, 7: 1, 2007; Luftl et al. Br J Dermatol, 151: 1213, 2004; Lohmann, et al. Melanoma Res, 13: 595, 2003; and Dhodapkar, et al. Cancer Immun, 3: 9, 2003).

There remains a need for a mAb that, while specifically recognizing the highly similar MAGE-A3 and MAGE-A6 proteins, does not cross-react with the closely related MAGE-A2 or A12 proteins, or any other known MAGE-A proteins. Additionally there is a need for such antibodies that are able to reliably detect MAGE-A3 and/or A6 on FFPE tissues.

The present invention provides an antigen binding protein which specifically binds to MAGE-A3 and MAGE-A6. The antigen binding protein may be an antibody, for example a monoclonal antibody (mAb).

Unless otherwise explained, all technical and scientific terms used herein have the meaning as commonly understood by one of ordinary skill in the art to which this disclosure belongs. Definitions of common terms in molecular biology can be found in Benjamin Lewin, *Genes V*, Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all molecular weight or molecular mass values, given for nucleic acids or polypeptides are approximate, and are provided for description.

Amino acids are abbreviated herein as follows: Alanine (Ala or A); Arginine (Arg or R); Asparagine (Asn or N); Aspartic acid (Asp or D); Cysteine (Cys or C); Glutamic Acid (Glu or E); Glutamine (Gln or Q); Glycine (Gly or G); Histidine (His or H); Isoleucine (Ile or I); Leucine (Leu or L); Lysine (Lys or K); Methionine (Met or M); Phenylalanine (Phe or F); Proline (Pro or P); Serine (Ser or S); Threonine (Thr or T); Tryptophan (Trp or W); Tyrosine (Tyr or Y) and Valine (Val or V).

The term "antigen binding protein" as used herein refers to antibodies, antibody fragments and other protein constructs, such as domains or regions, which are capable of specific binding to MAGE-A3.

The term "antibody" is used herein in the broadest sense to refer to molecules with an immunoglobulin-like domain and includes monoclonal, recombinant, polyclonal, chimeric, humanised, bispecific and heteroconjugate antibodies; a single variable domain or region, a domain antibody, antigen binding fragments, immunologically effective fragments, single chain Fv, diabodies, TANDABS™, etc (for a summary of alternative "antibody" formats see Holliger and Hudson, *Nature Biotechnology,* 2005, Vol 23, No. 9, 1126-1136).

As used herein, the modifier "monoclonal" refers to an antibody obtained from a substantially homogeneous population of antibodies, and does not indicate that the antibody was produced by any particular method. For example, monoclonal antibodies (mAbs) of the invention may be made by the hybridoma method (Kohler and Milstein, *Nature* 256:495 (1975), or by recombinant DNA methods, or isolated from phage libraries.

Monoclonal antibodies of the present invention are named according to the hybridoma from which they were isolated, e.g., mAb 1B1 was obtained from hybridoma 1B1.

The phrase "single variable region" refers to an antigen binding protein variable region (for example, $V_H$, $V_{HH}$, $V_L$) that specifically binds an antigen or epitope independently of a different variable region.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are considered to be "domain antibodies". As used herein $V_H$ includes camelid $V_{HH}$ domains.

As used herein the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" (or "single variable region") is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A domain can bind an antigen or epitope independently of a different variable region or domain.

As used herein, "MAGE-A" refers to MAGE-A obtained from, or having the same sequence as, human MAGE-A unless otherwise stated. Thus MAGE-A3 as used herein refers to polypeptide having the sequence of human MAGE-A3, unless otherwise stated.

The present inventors used the following scheme to generate monoclonal antibodies (illustrated in Table 1). Mice were immunized with either a combination of divergent MAGE-A3 peptides or with full-length recombinant MAGE-A3. The reactivity of sera from the immunized mice was tested using an Enzyme Linked Immunosorbent Assay (ELISA) against full-length recombinant MAGE-A3, in order to select the animal for use in hybridoma production. Monoclonal antibodies produced by the resulting hybridoma were screened against MAGE-A3, and selected mAbs were then tested for reactivity against MAGE-A3, MAGE-A12 and MAGE-A2; and against tissue that expressed MAGE-A3. This scheme may be used to produce additional mAbs that specifically bind to MAGE-A3 and MAGE-A6, without crossreacting to MAGE-A2 and/or MAGE-A12. Mabs produced may optionally be tested for reactivity against the peptides used in immunization.

TABLE 1

| Immunization | Sera Reactivity for Animal Selection | mAbs screening |
|---|---|---|
| IMM-134 MA3 peptides (divergent peptides); OR IMM-135 recMA3 (baculovirus) | ELISA against recMA3 | 1) No reactivity against recMA12 or recMA22 2) Other MA family members; AND Reactivity against rec and tissue expressing MA3 Optional: Reactivity against Peptides |

An antigen binding fragment may be provided by means of arrangement of one or more CDRs on non-antibody protein scaffolds such as a domain. A non-antibody protein scaffold or domain is one that has been subjected to protein engineering in order to obtain binding to a ligand other than its natural ligand, for example a domain which is a derivative of a scaffold selected from: CTLA-4 (EVIBODY™); lipocalin; Protein A derived molecules such as Z-domain of Protein A (AFFIBODY™, SpA), A-domain (Avimer/Maxibody); heat shock proteins such as GroE1 and GroES; transferrin (transbody); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than its natural ligand.

An antigen binding fragment or an immunologically effective fragment may comprise partial heavy or light chain variable sequences. Fragments are at least 5, 6, 8 or 10 amino acids in length. Alternatively the fragments are at least 15, at least 20, at least 50, at least 75, or at least 100 amino acids in length.

The terms "specifically binds", "specific binding", or "specifically binding" as used throughout the present specification in relation to antigen binding proteins, refer to the interaction between a protein or polypeptide and an antigen binding protein. The interaction is dependent on the presence of a specific structure (i.e., the antigenic determinant or epitope) of the protein or polypeptide that is recognized by the antigen binding protein. Antigen binding proteins may cross-react with different proteins/polypeptides that have the same antigenic determinant or epitope; this is not considered non-specific binding. Additionally, these terms refer to binding with high affinity, as compared to nonspecific binding. See e.g., Lodish, Cell Biology 538-9 (5$^{th}$ edition, 2004). The antigen binding proteins described herein bind to MAGE-A3 and/or MAGE-A6 with at least 2, 5, 10, 50, 100, or 1000 fold greater affinity than they bind to closely related molecules, such as MAGE-A2 or MAGE-A12.

The binding affinity or equilibrium dissociation constant ($K_D$) of the antigen binding protein-MAGE-A3 interaction may be 100 nM or less, 10 nM or less, 2 nM or less or 1 nM or less. Alternatively the $K_D$ may be between 5 and 10 nM; or between 1 and 2 nM. The $K_D$ may be between 1 pM and 500 µM; or between 500 pM and 1 nM. The binding affinity of the antigen binding protein is determined by the association rate constant ($k_a$) and the dissociation rate constant ($k_d$) ($K_D = k_d/k_a$). The binding affinity may be measured by any suitable method known in the art, such as BIACORE™, for example by antigen capture with MAGE-A3 coupled onto a CM5 chip by primary amine coupling and antibody capture onto this surface. Alternatively, the binding affinity can be measured by the FORTEBIO™ method, for example by antigen capture with MAGE-A3 coupled onto a CM5 needle by primary amine coupling and antibody capture onto this surface.

The dissociation rate constant ($k_d$) of the antigen binding protein may be $1\times10^{-3}$ s$^{-1}$ or less, $1\times10^{-4}$ s$^{-1}$ or less, or $1\times10^{-5}$ s$^{-1}$ or less. The $k_d$ may be between $1\times10^{-5}$ s$^{-1}$ and $1\times10^{-4}$ s$^{-1}$; or between $1\times10^{-4}$ s$^{-1}$ and $1\times10^{-3}$ s$^{-1}$. A slow $k_d$ may result in a slow dissociation of the antigen binding protein-ligand complex.

As used herein the term "derived" defines not only the source (reference source) of a material in the sense that the reference source is the physical origin of the material, but also defines material which is structurally identical to the material but that was not physically obtained from the reference source. Thus "an amino acid sequence derived from a donor antibody" refers to both a sequence physically obtained from (e.g., purified from) the donor antibody, but also to a sequence identical to but not physically obtained from the donor antibody.

By "isolated" it is intended that the molecule, such as an antigen binding protein, is removed from the environment in which it may be found in nature. For example, the molecule may be purified away from substances with which it would normally exist in nature. For example, the antigen binding protein can be purified to at least 95%, 96%, 97%, 98% or 99%, or greater with respect to a culture media containing the antigen binding protein.

The terms "$V_H$" and "$V_L$" are used herein to refer to the heavy chain variable region and light chain variable region, respectively, of an antigen binding protein.

A "CDR" as used herein refers to a Complementarity Determining Region amino acid sequence of an antigen binding protein. CDRs are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and full length antibody sequences are numbered according to the Kabat numbering convention, unless otherwise specified. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person. Therefore, the term "corresponding CDR" is used herein to refer to a CDR sequence using any numbering convention, for example those set out in Table 2.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 2 below represents one definition using each numbering convention for each CDR or binding unit. The Kabat numbering scheme is used in Table 2 to number the variable domain amino acid sequence. It should be noted that some of the CDR definitions may vary depending on the individual publication used.

TABLE 2

|    | Kabat CDR      | Chothia CDR    | AbM CDR        | Contact CDR    | Minimum binding unit |
|----|----------------|----------------|----------------|----------------|----------------------|
| H1 | 31-35/35A/35B  | 26-32/33/34    | 26-35/35A/35B  | 30-35/35A/35B  | 31-32                |
| H2 | 50-65          | 52-56          | 50-58          | 47-58          | 52-56                |
| H3 | 95-102         | 95-102         | 95-102         | 93-101         | 95-101               |
| L1 | 24-34          | 24-34          | 24-34          | 30-36          | 30-34                |
| L2 | 50-56          | 50-56          | 50-56          | 46-55          | 50-55                |
| L3 | 89-97          | 89-97          | 89-97          | 89-96          | 89-96                |

As used herein, the term "antigen binding site" refers to a site on an antigen binding protein which is capable of specifically binding to an antigen. This may be a single domain (for example, an epitope-binding domain), or single-chain Fv (ScFv) domains or it may be paired $V_H/V_L$ domains as can be found on a standard antibody.

The term "epitope" as used herein refers to that portion of the antigen that makes contact with a particular binding domain of the antigen binding protein. An epitope may be linear, comprising an essentially linear amino acid sequence from the antigen. Alternatively, an epitope may be conformational or discontinuous. For example, a conformational epitope comprises amino acid residues which require an element of structural constraint. A discontinuous epitope comprises amino acid residues that are separated by other sequences, i.e. not in a continuous sequence in the antigen's primary sequence. In the context of the antigen's tertiary and quaternary structure, the residues of a discontinuous epitope are near enough to each other to be bound by an antigen binding protein.

For nucleotide and amino acid sequences, the term "identity", "sequence identity", or "sequence similarity" refers to the degree of identity between two nucleic acid or two amino acid sequences, and if required when optimally aligned and compared with appropriate insertions or deletions.

The percent identity between two sequences is a function of the number of identical positions shared by the sequences (i.e., % identity=number of identical positions/total number of positions times 100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

In one method, a polynucleotide sequence may be identical to a reference polynucleotide sequence as described herein (see for example SEQ ID NO: 38, 40, 42, 44, 46 or 48), that is be 100% identical, or it may include up to a certain integer number of nucleotide alterations as compared to the reference sequence, such as at least 50, 60, 70, 75, 80, 85, 90, 95, 98, or 99% identical. Such alterations are selected from at least one nucleotide deletion, substitution (including transition and transversion), or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference polynucleotide sequence as described herein (see for example SEQ ID NO: 38, 40, 42, 44, 46 or 48), by the numerical percent of the respective percent identity (divided by 100) and subtracting that product from said total number of nucleotides in the reference polynucleotide sequence as described herein, or:

$$n_n \leq x_n - (x_n \bullet y),$$

wherein $n_n$ is the number of nucleotide alterations, $x_n$ is the total number of nucleotides in the reference polynucleotide sequence as described herein, and y is 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99% or 1.00 for 100%, $\bullet$ is the symbol for the multiplication operator, and wherein any non-integer product of $x_n$ and y is rounded down to the nearest integer prior to subtracting it from $x_n$.

Similarly, a polypeptide sequence may be identical to a polypeptide reference sequence as described herein (see for example SEQ ID NO: 39, 41, 43, 45, 47, 49, or 50-67) that is be 100% identical, or it may include up to a certain integer number of amino acid alterations as compared to the reference sequence such that the % identity is less than 100%, such as at least 50, 60, 70, 75, 80, 85, 90, 95, 98, or 99% identical. Such alterations are selected from the group consisting of at least one amino acid deletion, substitution (including conservative and non-conservative substitutions), or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the polypeptide reference sequence as described herein by the numerical percent of the respective percent identity (divided by 100) and then subtracting that product from said total number of amino acids in the polypeptide reference sequence as described herein, or:

$$n_a \leq x_a - (x_a \bullet y),$$

wherein $n_a$ is the number of amino acid alterations, $x_a$ is the total number of amino acids in the reference polypeptide sequence as described herein, and y is, 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99%, or 1.00 for 100%, $\bullet$ is the symbol for the multiplication operator, and wherein any non-integer product of $x_a$ and y is rounded down to the nearest integer prior to subtracting it from $x_a$.

The % identity may be determined across the full length of the sequence, or any fragments thereof; and with or without any insertions or deletions.

The terms "peptide", "polypeptide" and "protein" each refers to a molecule comprising two or more amino acid residues. A peptide may be monomeric or polymeric.

It is well recognised in the art that certain amino acid substitutions are regarded as being "conservative", i.e., the amino acids have similar chemical and physical properties. Tables of conservative amino acid substitutions are known in the art. Amino acids are typically divided into groups based on common side-chain properties and substitutions within groups that maintain all or substantially all of the binding affinity of the antigen binding protein are regarded as conservative substitutions. By way of example and not limitation, an amino acid with an aliphatic side chain may be substituted with another aliphatic amino acid, e.g., alanine, valine, leucine, isoleucine, and methionine; an amino acid with hydroxyl side chain may be substituted with another amino acid with a hydroxyl side chain, e.g., serine and threonine; an amino acid having aromatic side chains may be substituted with another amino acid having an aromatic side chain, e.g., phenylalanine, tyrosine, tryptophan, and histidine; an amino acid with a basic side chain may be substituted with another amino acid with a basic side chain, e.g., lysine, arginine, and histidine; an amino acid with an acidic side chain may be substituted with another amino acid with an acidic side chain, e.g., aspartic acid or glutamic acid; and a hydrophobic or hydrophilic amino acid may be replaced with another hydrophobic or hydrophilic amino acid, respectively.

The present antigen binding proteins described herein specifically bind only MAGE-A3 and MAGE-A6 from MAGE-A family. The present invention provides an antigen binding protein which specifically binds to MAGE-A3 and which comprises or consists of:

(i) a heavy chain variable region of SEQ ID NO: 47 (or a variant heavy chain variable region with 75% or greater sequence identity to SEQ ID NO:47) and a light chain variable region of SEQ ID NO:49 (or a light chain variable region with 75% or greater sequence identity to SEQ ID NO:49);

(ii) a heavy chain variable region of SEQ ID NO:39 (or a variant heavy chain variable region with 75% or greater sequence identity to SEQ ID NO:39) and a light chain variable region of SEQ ID NO:41 (or a light chain variable region with 75% or greater sequence identity to SEQ ID NO:41); or (iii) a heavy chain variable region of SEQ ID NO: 43 (or a variant heavy chain variable region with 75% or greater sequence identity to SEQ ID NO:43); and a light chain variable region of SEQ ID NO:45 (or a light chain variable region with 75% or greater sequence identity to SEQ ID NO:45).

The present invention provides an antigen binding protein which binds to MAGE-A3 and comprises a CDRH3 having a sequence selected from SEQ ID NO: 52, 58 or 64, or a variant CDRH3 sequence thereof. Such an antigen binding protein may further comprise in addition to the CDRH3 sequences described above, one or more of a CDRH1, a CDRH2, a CDRL1, a CDRL2, or a CDRL3, in any combination, where the CDR(s) has a sequence selected from: SEQ ID NO:50, 56 or 62 (CDRH1), SEQ ID NO: 51, 57 or 63 (CDRH2), SEQ ID NO: 53, 59 or 65 (CDRL1), SEQ ID NO: 54, 60 or 66 (CDRL2), and SEQ ID NO:55, 61 or 67 (CDRL3); or a variant CDR sequence thereof.

The invention also provides an antigen binding protein which binds to MAGE-A3 and comprises a heavy chain variable region selected from SEQ ID NO: 39, 43 or 47. The antigen binding protein may comprise a light chain variable region selected from SEQ ID NO: 41, 45 or 49. Any of the heavy chain variable regions may be combined with any of the light chain variable regions.

The invention also provides an antigen binding protein which binds to MAGE-A3 and comprises any one of the following heavy chain variable region and light chain variable region combinations: (SEQ ID NO: 39 and SEQ ID NO:41) or (SEQ ID NO: 43 and SEQ ID NO:45), or (SEQ ID NO:47 and SEQ ID NO:49).

The invention also provides an antibody heavy chain variable region having 75% or greater, 80% or greater, 85% or greater, 90% or greater, 95% or greater, 98% or greater, 99% or greater or 100% identity to any one of SEQ ID NO: 39, 43, and 47. The invention also provides an antibody light chain variable region having 75% or greater, 80% or greater, 85% or greater, 90% or greater, 95% or greater, 98% or greater, 99% or greater, or 100% identity to any one of SEQ ID NO: 41, 45 and 49. The percentage identity of the variants of SEQ ID NO: 39, 43, 47, 41, 45 or 49 may be determined across the full length of the sequence. Canonical CDR or framework residue substitutions as described above may be present in such heavy or light chain variable regions having the above described sequence identities. Antigen binding proteins having the above described sequence identities may display a potency for binding to MAGE-A3, as demonstrated by EC50, of within 10 fold, or within 5 fold of the potency demonstrated by the reference sequence. Potency for binding to MAGE-A3, as demonstrated by EC50, may be carried out by an ELISA assay.

The antibody heavy chain variable region may be a variant of any one of SEQ ID NO: 39, 43, and 47 which contains 30, 25, 20, 15, 10, 9, 8, 7, 6, 5, 4, 3, 2 or 1 amino acid substitutions, insertions or deletions. The antibody light chain variable region may be a variant of any one of SEQ ID NO: 41, 45 and 49 which contains 30, 25, 20, 15, 10, 9, 8, 7, 6, 5, 4, 3, 2 or 1 amino acid substitutions, insertions or deletions.

For example, the antigen binding protein may comprise CDRH3 (SEQ ID NO:52) and CDRH1 (SEQ ID NO: 50) or variants thereof. The antigen binding protein may comprise CDRH3 (SEQ ID NO: 52) and CDRH2 (SEQ ID NO: 51) or variants thereof. The antigen binding protein may comprise CDRH1 (SEQ ID NO: 50) and CDRH2 (SEQ ID NO: 51), and CDRH3 (SEQ ID NO: 52), or variants thereof.

The antigen binding protein may comprise CDRL1 (SEQ ID NO: 53) and CDRL2 (SEQ ID NO: 54), or variants thereof. The antigen binding protein may comprise CDRL2 (SEQ ID NO: 54) and CDRL3 (SEQ ID NO:55), or variants thereof. The antigen binding protein may comprise CDRL1 (SEQ ID NO: 53), CDRL2 (SEQ ID NO:54) and CDRL3 (SEQ ID NO:55), or variants thereof.

The antigen binding protein may comprise CDRH3 (SEQ ID NO:52) and CDRL3 (SEQ ID NO:55), or variants thereof. The antigen binding protein may comprise CDRH3 (SEQ ID NO: 52), CDRH2 (SEQ ID NO:51) and CDRL3 (SEQ ID NO:55), or variants thereof. The antigen binding protein may comprise CDRH3 (SEQ ID NO:52), CDRH2 (SEQ ID NO:51) CDRL2 (SEQ ID NO: 54) and CDRL3 (SEQ ID NO:55), or variants thereof.

The antigen binding protein may comprise CDRH1 (SEQ ID NO:50), CDRH2 (SEQ ID NO:51), CDRH3 (SEQ ID NO:52), CDRL1 (SEQ ID NO:53), CDRL2 (SEQ ID NO:54) and CDRL3 (SEQ ID NO:55). Alternatively, variant CDRs may be present.

The present invention also provides an antigen binding protein as described above, which binds to MAGE-A3, and which comprises in place of the CDRH3 recited above, the corresponding CDRH3 of the variable domain sequence of SEQ ID NO:43 or SEQ ID NO:47, or a variant CDRH3 thereof. Thus the antigen binding protein may be as described above but having a CDRH3 of SEQ ID NO:58 or SEQ ID NO:64.

The present invention also provides an antigen binding protein as described above, which binds to MAGE-A3, and which comprises in place of the CDRH1, CDRH2, CDRL1, CDRL2 or CDRL3 recited above, the corresponding CDR of the variable domain sequence of SEQ ID NO:43, SEQ ID NO:45, SEQ ID NO:47, or SEQ ID NO:49, or a variant CDR thereof.

For example, the antigen binding protein may comprise a corresponding CDRH3 and a corresponding CDRH1, or variants thereof. The antigen binding protein may comprise a corresponding CDRH3 and a corresponding CDRH2, or variants thereof. The antigen binding protein may comprise a corresponding CDRH1, a corresponding CDRH2, and a corresponding CDRH3; or variants thereof. The antigen binding protein may comprise a corresponding CDRL1 and a corresponding CDRL2, or variants thereof. The antigen binding protein may comprise a corresponding CDRL2 and a corresponding CDRL3, or variants thereof. The antigen binding protein may comprise a corresponding CDRL1, a corresponding CDRL2 and a corresponding CDRL3, or variants thereof. The antigen binding protein may comprise a corresponding CDRH3 and a corresponding CDRL3, or variants thereof. The antigen binding protein may comprise a corresponding CDRH3, a corresponding CDRH2 and a corresponding CDRL3, or variants thereof. The antigen binding protein may comprise a corresponding CDRH3, a corresponding CDRH2, a corresponding CDRL2 and a corresponding CDRL3, or variants thereof. The antigen binding protein may comprise a corresponding CDRH1, a corresponding CDRH2, a corresponding CDRH3, a corresponding CDRL1, a corresponding CDRL2 and a corresponding CDRL3, or variants thereof.

The antigen binding proteins of the present invention may comprise CDRH3 (SEQ ID NO:58) and CDRH1 (SEQ ID NO: 56) or variants thereof. The antigen binding protein may comprise CDRH3 (SEQ ID NO: 58) and CDRH2 (SEQ ID NO: 57) or variants thereof. The antigen binding protein may comprise CDRH1 (SEQ ID NO: 56) and CDRH2 (SEQ ID NO: 57), and CDRH3 (SEQ ID NO: 58), or variants thereof.

The antigen binding protein may comprise CDRL1 (SEQ ID NO: 59) and CDRL2 (SEQ ID NO: 60), or variants thereof. The antigen binding protein may comprise CDRL2 (SEQ ID NO: 60) and CDRL3 (SEQ ID NO:61), or variants thereof. The antigen binding protein may comprise CDRL1 (SEQ ID NO: 59), CDRL2 (SEQ ID NO:60) and CDRL3 (SEQ ID NO:61), or variants thereof.

The antigen binding protein may comprise CDRH3 (SEQ ID NO:58) and CDRL3 (SEQ ID NO:61), or variants thereof. The antigen binding protein may comprise CDRH3 (SEQ ID NO: 58), CDRH2 (SEQ ID NO:57) and CDRL3 (SEQ ID NO:61), or variants thereof. The antigen binding protein may comprise CDRH3 (SEQ ID NO:58), CDRH2 (SEQ ID NO:57) CDRL2 (SEQ ID NO: 60) and CDRL3 (SEQ ID NO:61), or variants thereof.

The antigen binding protein may comprise CDRH1 (SEQ ID NO:56), CDRH2 (SEQ ID NO:57), CDRH3 (SEQ ID NO:58), CDRL1 (SEQ ID NO:59), CDRL2 (SEQ ID NO:60) and CDRL3 (SEQ ID NO:61). Alternatively, variant CDRs may be present.

The present invention also provides an antigen binding protein as described above, which binds to MAGE-A3, and which comprises in place of the CDRH3 recited above, the corresponding CDRH3 of the variable domain sequence of SEQ ID NO:39 or SEQ ID NO:47, or a variant CDRH3 thereof. Thus the antigen binding protein may be as described above but having a CDRH3 of SEQ ID NO:52 or SEQ ID NO:64.

The present invention also provides an antigen binding protein as described above, which binds to MAGE-A3, and which comprises in place of the CDRH1, CDRH2, CDRL1, CDRL2 or CDRL3 recited above, the corresponding CDR of the variable domain sequence of SEQ ID NO:39, SEQ ID NO:41 SEQ ID NO:47, or SEQ ID NO:49, or a variant CDR thereof.

For example, the antigen binding protein may comprise a corresponding CDRH3 and a corresponding CDRH1, or variants thereof. The antigen binding protein may comprise a corresponding CDRH3 and a corresponding CDRH2, or variants thereof. The antigen binding protein may comprise a corresponding CDRH1, a corresponding CDRH2, and a corresponding CDRH3; or variants thereof. The antigen binding protein may comprise a corresponding CDRL1 and a corresponding CDRL2, or variants thereof. The antigen binding protein may comprise a corresponding CDRL2 and a corresponding CDRL3, or variants thereof. The antigen binding protein may comprise a corresponding CDRL1, a corresponding CDRL2 and a corresponding CDRL3, or variants thereof. The antigen binding protein may comprise a corresponding CDRH3 and a corresponding CDRL3, or variants thereof. The antigen binding protein may comprise a corresponding CDRH3, a corresponding CDRH2 and a corresponding CDRL3, or variants thereof. The antigen binding protein may comprise a corresponding CDRH3, a corresponding CDRH2, a corresponding CDRL2 and a corresponding CDRL3, or variants thereof. The antigen binding protein may comprise a corresponding CDRH1, a corresponding CDRH2, a corresponding CDRH3, a corresponding CDRL1, a corresponding CDRL2 and a corresponding CDRL3, or variants thereof.

The antigen binding proteins of the present invention may comprise CDRH3 (SEQ ID NO:64) and CDRH1 (SEQ ID NO: 62) or variants thereof. The antigen binding protein may comprise CDRH3 (SEQ ID NO: 64) and CDRH2 (SEQ ID NO: 63) or variants thereof. The antigen binding protein may comprise CDRH1 (SEQ ID NO: 62) and CDRH2 (SEQ ID NO: 63), and CDRH3 (SEQ ID NO: 64), or variants thereof.

The antigen binding protein may comprise CDRL1 (SEQ ID NO: 65) and CDRL2 (SEQ ID NO: 66), or variants thereof. The antigen binding protein may comprise CDRL2 (SEQ ID NO: 66) and CDRL3 (SEQ ID NO:67), or variants thereof. The antigen binding protein may comprise CDRL1 (SEQ ID NO: 65), CDRL2 (SEQ ID NO:66) and CDRL3 (SEQ ID NO:67) or variants thereof.

The antigen binding protein may comprise CDRH3 (SEQ ID NO:64) and CDRL3 (SEQ ID NO:67), or variants thereof. The antigen binding protein may comprise CDRH3 (SEQ ID NO: 64), CDRH2 (SEQ ID NO:63) and CDRL3 (SEQ ID NO:67), or variants thereof. The antigen binding protein may comprise CDRH3 (SEQ ID NO:64), CDRH2 (SEQ ID NO:63) CDRL2 (SEQ ID NO: 66) and CDRL3 (SEQ ID NO:67), or variants thereof.

The antigen binding protein may comprise CDRH1 (SEQ ID NO:62), CDRH2 (SEQ ID NO:63), CDRH3 (SEQ ID NO:64), CDRL1 (SEQ ID NO:65), CDRL2 (SEQ ID NO:66) and CDRL3 (SEQ ID NO:67). Alternatively, variant CDRs may be present.

The present invention also provides an antigen binding protein as described above, which binds to MAGE-A3, and which comprises in place of the CDRH3 recited above, the corresponding CDRH3 of the variable domain sequence of SEQ ID NO:39 or SEQ ID NO:43, or a variant CDRH3 thereof. Thus the antigen binding protein may be as described above but having a CDRH3 of SEQ ID NO:52 or SEQ ID NO:58.

The present invention also provides an antigen binding protein as described above, which binds to MAGE-A3, and which comprises in place of the CDRH1, CDRH2, CDRL1, CDRL2 or CDRL3 recited above, the corresponding CDR of the variable domain sequence of SEQ ID NO:39, SEQ ID NO:41 SEQ ID NO:43, or SEQ ID NO:45, or a variant CDR thereof.

For example, the antigen binding protein may comprise a corresponding CDRH3 and a corresponding CDRH1, or variants thereof. The antigen binding protein may comprise a corresponding CDRH3 and a corresponding CDRH2, or variants thereof. The antigen binding protein may comprise a corresponding CDRH1, a corresponding CDRH2, and a corresponding CDRH3; or variants thereof. The antigen binding protein may comprise a corresponding CDRL1 and a corresponding CDRL2, or variants thereof. The antigen binding protein may comprise a corresponding CDRL2 and a corresponding CDRL3, or variants thereof. The antigen binding protein may comprise a corresponding CDRL1, a corresponding CDRL2 and a corresponding CDRL3, or variants thereof. The antigen binding protein may comprise a corresponding CDRH3 and a corresponding CDRL3, or variants thereof. The antigen binding protein may comprise a corresponding CDRH3, a corresponding CDRH2 and a corresponding CDRL3, or variants thereof. The antigen binding protein may comprise a corresponding CDRH3, a corresponding CDRH2, a corresponding CDRL2 and a corresponding CDRL3, or variants thereof. The antigen binding protein may comprise a corresponding CDRH1, a corresponding CDRH2, a corresponding CDRH3, a corresponding CDRL1, a corresponding CDRL2 and a corresponding CDRL3, or variants thereof.

Corresponding CDRs can be defined by reference to Kabat (1987), Chothia (1989), AbM or contact methods. One definition of each of the methods can be found at Table 2 and can be applied to the reference heavy chain variable region SEQ ID NO: 39, 43, or 47 and the reference light chain variable region SEQ ID NO: 41, 45, or 49 to determine corresponding CDRs.

A CDR variant or variant binding unit includes an amino acid sequence modified by at least one amino acid (for example by one, two, or no more than 6 amino acids), which modification permits the variant to retain the biological characteristics of the unmodified sequence. For example, the variant is a functional variant which binds to MAGE-A3. A partial alteration of the CDR amino acid sequence may be by deletion or substitution of one, two or several amino acids; or by addition or insertion of one, two or several amino acids; or by a combination thereof (for example by one, two or no more than 6 amino acids). The CDR variant or binding unit variant may contain 1, 2, 3, 4, 5 or 6 amino acid substitutions, additions or deletions, in any combination, in the amino acid sequence. The substitutions in amino acid residues may be conservative substitutions, for example, substituting one hydrophobic amino acid for an alternative hydrophobic amino acid. For example leucine may be substituted with valine, or isoleucine.

The CDRs L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Martin and Thornton (1996; *J Mol Biol* 263:800-815) have generated an automatic method to define the "key residue" canonical templates. Cluster analysis is used to define the canonical classes for sets of CDRs, and canonical templates are then identified by analysing buried hydrophobics, hydrogen-bonding residues, and conserved glycines and prolines. The CDRs of antibody sequences can be assigned to canonical classes by comparing the sequences to the key residue templates and scoring each template using identity or similarity matrices.

An antigen binding protein of the present invention that comprises a CDR corresponding to a reference CDR may display a potency for binding to MAGE-A3, as demonstrated by EC50, of within 10 fold, or within 5 fold of the potency demonstrated by an antigen binding protein comprising the reference CDR. An antigen binding protein of the present invention that comprises a variant of a reference CDR, may display a potency for binding to MAGE-A3, as demonstrated by EC50, of within 10 fold, or within 5 fold of the potency demonstrated by an antigen binding protein comprising the reference CDR. Reference CDRs include those having a sequence selected from the group consisting of SEQ ID NO:50, 51, 52, 53, 54, 55, 56, 57, 58, 59, 60, 61, 62, 63, 64 65, 66, and 67.

One or more of the CDRs, corresponding CDRs, variant CDRs or binding units described herein may be present in the context of a human framework, for example as a humanised or chimeric variable domain.

Any of the heavy chain variable regions may be combined with a suitable human constant region. Any of the light chain variable regions may be combined with a suitable constant region.

The MAGE-A3 polypeptide to which the antigen binding protein binds may be a recombinant polypeptide. MAGE-A3 may be in solution or may be attached to a solid surface. For example, MAGE-A3 may be attached to beads such as magnetic beads. MAGE-A3 may be biotinylated. The biotin molecule conjugated to MAGE-A3 may be used to immobilize MAGE-A3 on a solid surface by coupling biotin-streptavidin on the solid surface.

The present invention also provides an antigen binding protein as described above, which binds to MAGE-A3, and which comprises a heavy chain variable region acceptor antibody framework having 75% or greater sequence identity to a framework region selected from SEQ ID NO:39, SEQ ID NO:43, SEQ ID NO:47, SEQ ID NO:41, SEQ ID NO:45, and SEQ ID NO:49.

The antigen binding protein may be derived from rat, mouse, primate (e.g. cynomolgus, Old World monkey or Great Ape) or Human. The antigen binding protein may be a humanised or chimeric antibody.

The antigen binding protein may comprise a constant region, which may be of any isotype or subclass. The constant region may be of the IgG isotype, for example IgG1, IgG2, IgG3, IgG4 or variants thereof. The antigen binding protein constant region may be IgG1.

Mutational changes to the Fc effector portion of the antibody can be used to change the affinity of the interaction between the FcRn and antibody to modulate antibody turnover. The half life of the antibody can be extended in vivo. The antigen binding proteins of the invention may be Fc disabled. Alternatively, the antigen binding protein may be Fc enabled.

The present invention also provides a nucleic acid molecule which encodes an antigen binding protein as described herein. The nucleic acid molecule may comprise a sequence encoding (i) one or more CDRHs, or the heavy chain variable sequence; and (ii) one or more CDRLs, or the light chain variable sequence, with (i) and (ii) on the same nucleic acid molecule. Alternatively, the nucleic acid molecule which encodes an antigen binding protein described herein may comprise sequences encoding (a) one or more CDRHs, or the heavy chain variable sequence; or (b) one or more CDRLs, or the light chain variable sequence, with (a) and (b) on separate nucleic acid molecules.

The nucleic acid molecule which encodes the heavy chain variable sequence may comprise or consist of any one of SEQ ID NO:38, 42 or 46. The nucleic acid molecule which encodes the light chain variable sequence may comprise or consist of any one of SEQ ID NO:40, 44, or 48.

The present invention also provides an expression vector comprising a nucleic acid molecule as described herein. Also provided is a recombinant host cell comprising an expression vector as described herein.

The antigen binding proteins described herein may be produced in a suitable host cell. A method for the production of the antigen binding proteins as described herein comprises the step of culturing a host cell as described herein and recovering the antigen binding protein. A recombinant transformed, transfected, or transduced host cell may comprise an expression cassette comprising a polynucleotide encoding a heavy chain variable domain of the antigen binding protein described herein and further comprising a polynucleotide encoding a light chain variable region of the antigen binding protein described herein. Alternatively, a recombinant transformed, transfected or transduced host cell may comprise at least one expression cassette, whereby a first expression cassette comprises a polynucleotide encoding a heavy chain variable region of the antigen binding protein described herein and further comprise a second cassette comprising a polynucleotide encoding a light chain variable region of the antigen binding protein described herein. A stably transformed host cell may comprise a vector comprising one or more expression cassettes encoding a heavy chain and/or a light chain variable region of the antigen binding protein described herein. For example such host cells may comprise a first vector encoding the light chain variable region and a second vector encoding the heavy chain variable region.

The host cell may be eukaryotic, for example mammalian. Examples of such cell lines include CHO (Chinese Hamster Ovary) or NS0 (myeloma cell line). The host cell may be a non-human host cell. The host cell may be a non-embryonic host cell. The host cell may be cultured in a culture media, for example serum-free culture media. The antigen binding protein may be secreted by the host cell into the culture media. The antigen binding protein can be purified to at least 95% or greater (e.g. 98% or greater) with respect to said culture media containing the antigen binding protein.

The antigen binding proteins of the present invention may be provided as a composition comprising the antibody binding protein and a physiologically acceptable carrier, or as a pharmaceutical composition comprising the antigen binding protein and a pharmaceutically acceptable carrier. A kit-of-parts comprising such a composition together with instructions for use may be provided. For convenience, the kit may comprise the reagents in predetermined amounts with instructions for use.

Antibody Structures

The light chains of antibodies from most vertebrate species can be assigned to one of two types, called Kappa and Lambda, based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b.

The more conserved portions of the variable region are called Framework regions (FR). The variable domains of intact heavy and light chains each comprise four FR connected by three CDRs. The CDRs in each chain are held together in close proximity by the FR regions and, with the CDRs from the other chain, contribute to the formation of the antigen binding site of antibodies.

Production Methods

Antigen binding proteins may be produced in transgenic organisms such as goats (see e.g. Pollock et al. (1999) *J. Immunol. Methods* 231: 147-157), chickens (see e.g. Morrow (2000) *Genet. Eng. News* 20:1-55, mice (see e.g. Pollock et al. 1999) or plants (see e.g. Doran (2000) *Curr. Opinion Biotechnol.* 11: 199-204; Ma (1998) *Nat. Med.* 4: 601-606; Baez et al. (2000) *BioPharm* 13: 50-54; Stoger et al. (2000) *Plant Mol. Biol.* 42: 583-590).

Antigen binding proteins may also be produced by chemical synthesis. However, antigen binding proteins are typically produced using recombinant cell culturing technology well known to those skilled in the art. A polynucleotide encoding the antigen binding protein is isolated and inserted into a replicable vector such as a plasmid for further cloning (amplification) or expression. One expression system is a glutamate synthetase system (such as sold by Lonza Biologics, Basel, Switzerland), particularly where the host cell is CHO or NS0. Polynucleotide encoding the antigen binding protein is readily isolated and sequenced using conventional procedures (e.g. oligonucleotide probes). Vectors that may be used include plasmid, virus, phage, transposons, minichromosomes of which plasmids are typically used. Generally such vectors further include a signal sequence, origin of replication, one or more marker genes, an enhancer element, a promoter and transcription termination sequences operably linked to the antigen binding protein polynucleotide so as to facilitate expression. Polynucleotide encoding the light and heavy chains may be inserted into separate vectors and introduced (for example by transformation, transfection, electroporation or transduction) into the same host cell concurrently or sequentially or, if desired both the heavy chain and light chain can be inserted into the same vector prior to said introduction.

Codon optimisation of the polynucleotide sequences of the present invention may be used to increase the level of protein produced by a host cell. Several methods have been published (Nakamura et al. (1996) *Nucleic Acids Research* 24: 214-215; WO98/34640; WO97/11086). Due to the redundancy of the genetic code, alternative polynucleotides to those disclosed herein (particularly those codon optimised for expression in a given host cell) may also encode the antigen binding proteins described herein. The codon usage of polynucleotides encoding the antigen binding proteins of this invention can be modified to accommodate codon bias of the host cell to augment transcript and/or product yield (eg Hoekema et al., *Mol*

*Cell Biol* 1987 7(8): 2914-24). The choice of codons may be based upon suitable compatibility with the host cell used for expression.

Antigen binding proteins may be produced as a fusion protein with a heterologous signal sequence having a specific cleavage site at the N-terminus of the mature protein. The signal sequence should be recognised and processed by the host cell. For prokaryotic host cells, the signal sequence may be for example an alkaline phosphatase, penicillinase, or heat stable enterotoxin II leaders. For yeast secretion the signal sequences may be for example a yeast invertase leader, a factor leader or acid phosphatase leaders see e.g. WO90/13646. In mammalian cell systems, viral secretory leaders such as herpes simplex gD signal and a native immunoglobulin signal sequence may be suitable. Typically the signal sequence is ligated in reading frame to DNA encoding the antigen binding protein.

Origin of replications are well known in the art with pBR322 suitable for most gram-negative bacteria, 2μ plasmid for most yeast, and various viral origins such as SV40, polyoma, adenovirus, VSV or BPV for most mammalian cells. Generally the origin of replication component is not needed for mammalian expression vectors but the SV40 may be used since it contains the early promoter.

Typical selection genes encode proteins that (a) confer resistance to antibiotics or other toxins e.g. ampicillin, neomycin, methotrexate or tetracycline or (b) complement auxiotrophic deficiencies or supply nutrients not available in the complex media or (c) combinations of both. The selection scheme may involve arresting growth of the host cell. Cells, which have been successfully transformed with the genes encoding the antigen binding protein, survive due to e.g. drug resistance conferred by the co-delivered selection marker. One example is the dihydrofolate reductase (DHFR) selection marker wherein transformants are cultured in the presence of methotrexate. Cells can be cultured in the presence of increasing amounts of methotrexate to amplify the copy number of the exogenous gene of interest. CHO cells are a particularly useful cell line for the DHFR selection. A further example is the glutamate synthetase expression system (Lonza Biologics, Basel, Switzerland). An example of a selection gene for use in yeast is the trp1 gene, see Stinchcomb et al. (1979) *Nature* 282: 38.

Suitable promoters for expressing antigen binding proteins are operably linked to DNA/polynucleotide encoding the antigen binding protein. Promoters for prokaryotic hosts include phoA promoter, beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose-6-phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40. Of course the choice of promoter is based upon suitable compatibility with the host cell used for expression. A first plasmid may comprise a RSV and/or SV40 and/or CMV promoter, DNA encoding light chain variable region ($V_L$), κC region together with neomycin and ampicillin resistance selection markers and a second plasmid comprising a RSV or SV40 promoter, DNA encoding the heavy chain variable region ($V_H$), DNA encoding the γ1 constant region, DHFR and ampicillin resistance markers.

Where appropriate, e.g. for expression in higher eukaryotes, an enhancer element operably linked to the promoter element in a vector may be used. Mammalian enhancer sequences include enhancer elements from globin, elastase, albumin, fetoprotein and insulin. Alternatively, one may use an enhancer element from a eukaroytic cell virus such as SV40 enhancer (at bp100-270), cytomegalovirus early promoter enhancer, polyma enhancer, baculoviral enhancer or murine IgG2a locus (see WO04/009823). The enhancer may be located on the vector at a site upstream to the promoter. Alternatively, the enhancer may be located elsewhere, for example within the untranslated region or downstream of the polyadenylation signal. The choice and positioning of enhancer may be based upon suitable compatibility with the host cell used for expression.

In eukaryotic systems, polyadenylation signals are operably linked to DNA/polynucleotide encoding the antigen binding protein. Such signals are typically placed 3' of the open reading frame. In mammalian systems, non-limiting examples include signals derived from growth hormones, elongation factor-1 alpha and viral (eg SV40) genes or retroviral long terminal repeats. In yeast systems non-limiting examples of polydenylation/termination signals include those derived from the phosphoglycerate kinase (PGK) and the alcohol dehydrogenase 1 (ADH) genes. In prokaryotic system polyadenylation signals are typically not required and it is instead usual to employ shorter and more defined terminator sequences. The choice of polyadenylation/termination sequences may be based upon suitable compatibility with the host cell used for expression.

In addition to the above, other features that can be employed to enhance yields include chromatin remodelling elements, introns and host-cell specific codon modification.

Suitable host cells for cloning or expressing vectors encoding antigen binding proteins are prokaroytic, yeast or higher eukaryotic cells. Suitable prokaryotic cells include eubacteria e.g. enterobacteriaceae such as *Escherichia* e.g. *E. coli* (for example ATCC 31,446; 31,537; 27,325), *Enterobacter, Envinia, Klebsiella Proteus, Salmonella* e.g. *Salmonella typhimurium, Serratia* e.g. *Serratia marcescans* and *Shigella* as well as Bacilli such as *B. subtilis* and *B. licheniformis* (see DD 266 710), *Pseudomonas* such as *P. aeruginosa* and *Streptomyces*. Of the yeast host cells, *Saccharomyces cerevisiae, Schizosaccharomyces pombe, Kluyveromyces* (e.g. ATCC 16,045; 12,424; 24178; 56,500), *yarrowia* (EP402, 226), *Pichia pastoris* (EP 183 070, see also Peng et al. (2004) J. Biotechnol. 108: 185-192), *Candida, Trichoderma reesia* (EP 244 234), Penicillin, *Tolypocladium* and *Aspergillus* hosts such as *A. nidulans* and *A. niger* are also contemplated.

Higher eukaryotic host cells include mammalian cells such as COS-1 (ATCC No. CRL 1650), COS-7 (ATCC CRL 1651), human embryonic kidney line 293, baby hamster kidney cells (BHK) (ATCC CRL. 1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub et al. (1986) Somatic Cell Mol. Genet. 12: 555-556), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0.

Such host cells may also be further engineered or adapted to modify quality, function and/or yield of the antigen binding protein. Non-limiting examples include expression of specific modifying (e.g. glycosylation) enzymes and protein folding chaperones.

Host cells transformed with vectors encoding antigen binding proteins may be cultured by any method known to those skilled in the art. Host cells may be cultured in spinner flasks, roller bottles or hollow fibre systems but for large scale production stirred tank reactors are used particularly for suspension cultures. The stirred tankers may be adapted for aeration using e.g. spargers, baffles or low shear impellers. For bubble columns and airlift reactors direct aeration with air or oxygen bubbles maybe used. Where the host cells are cultured in a serum free culture media, the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly invertebrate host cells may utilise a variety of operational modes such as fed-batch, repeated batch processing (see Drapeau et al. (1994) Cytotechnology 15: 103-109), extended batch process or perfusion culture. Although recombinantly transformed mammalian host cells may be cultured in serum-containing media such as fetal calf serum (FCS), for example such host cells are cultured in synthetic serum-free media such as disclosed in Keen et al. (1995) Cytotechnology 17: 153-163, or commercially available media such as ProCHO-CDM or ULTRACHOT™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg et al. (1995) in *Animal Cell Technology: Developments towards the 21st century* (Beuvery et al. eds, 619-623, Kluwer Academic publishers).

Antigen binding proteins secreted into the media may be recovered and purified using a variety of techniques to provide a degree of purification suitable for the intended use. For example the use of antigen binding proteins for the treatment of human patients typically mandates at least 95% purity, more typically 98% or 99% or greater purity (compared to the crude culture medium). Cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. The antibodies, following various clarification steps, can be captured using Protein A or G affinity chromatography. Further chromatography steps can follow such as ion exchange and/or HA chromatography, anion or cation exchange, size exclusion chromatography and ammonium sulphate precipitation. Various virus removal steps may also be employed (e.g. nanofiltration using e.g. a DV-20 filter). Following these various steps, a purified (for example a monoclonal) preparation comprising at least 75 mg/ml or greater, or 100 mg/ml or greater, of the antigen binding protein is provided. Such preparations are substantially free of aggregated forms of antigen binding proteins.

Bacterial systems may be used for the expression of antigen binding fragments. Such fragments can be localised intracellularly, within the periplasm or secreted extracellularly. Insoluble proteins can be extracted and refolded to form active proteins according to methods known to those skilled in the art, see Sanchez et al. (1999) J. Biotechnol. 72: 13-20; and Cupit et al. (1999) *Lett Appl Microbiol* 29: 273-277.

Deamidation is a chemical reaction in which an amide functional group is removed. In biochemistry, the reaction is important in the degradation of proteins because it damages the amide-containing side chains of the amino acids asparagine and glutamine. Deamidation reactions are common post-translational modifications occurring during the manufacture of proteins for medical uses. For example, a reduction or loss of in vitro or in vivo biological activity has been reported for recombinant human DNAse and recombinant soluble CD4, whereas other recombinant proteins appear to be unaffected.

Methods of Producing mAbs Specifically Binding to MAGE-A3 and MAGE-A6

The present invention further provides a method for making, identifying, and producing monoclonal antibodies that specifically bind to MAGE-A3 and MAGE-A6, but do not bind (or do not specifically bind) to MAGE-A2 or MAGE-A12. The method comprises immunizing an animal (such as a mouse) with at least one immunizing peptide comprising a divergent epitope, i.e., an amino acid sequence that is 100% similar to sequences found in both MAGE-A3 and MAGE-A6, but which shows less sequence similarity to any part of MAGE-A2 or MAGE-A12. The amino acid sequence may show less than 90%, 80%, 77%, 75%, or 70% similarity to any part of MAGE-A2 or MAGE-A12. Immunizing peptides comprising the amino acid sequence are synthesized and optionally linked to a carrier protein (such as Keyhole limpet haemocyanin); one or two amino acids may be added to the amino acid sequence to facilitate linkage to, and distance from, the carrier protein. Examples of such peptides include SEQ ID NO:35, SEQ ID NO:36, and SEQ ID NO:37. The present invention further includes a method for making, identifying, and producing monoclonal antibodies that specifically bind to MAGE-A3 and MAGE-A6, but do not bind (or do not specifically bind) to any other MAGE-A sub-family member.

After immunization, the cells of the immunized animal are used to produce monoclonal antibodies by any suitable method, such as the hybridoma method first described by Kohler and Milstein, *Nature*, 256:495 (1975). Screening is performed to identify those monoclonal antibodies that specifically bind to MAGE-A3 and MAGE-A6, but not to MAGE-A2 or MAGE-A12. Such screening may be conducted using hybridoma culture supernatant or purified monoclonal antibodies. DNA encoding the monoclonal antibodies can be isolated from the hybridoma cells and sequenced, using methods known in the art, to obtain the amino acid sequence of the heavy and light chains of the monoclonal antibody. DNA encoding the desired monoclonal antibody (or portion of monoclonal antibody) can then be placed into expression vectors, which are transfected into suitable host cells, for expression of the encoded polypeptide. The DNA may also be modified, e.g., by substituting the coding sequence for human heavy and/or light chain framework regions in place of the corresponding sequence.

Methods of Use

The antigen binding proteins described herein may be used to detect MAGE-A3 and/or MAGE-A6 in a biological sample in vitro or in vivo. Detection may be for research, therapeutic or diagnostic purposes. For example, the anti-MAGE-A3 antigen binding proteins can be used to detect MAGE-A3 in cultured cells, in a tissue, in bodily fluids or in serum. The tissue may have been first removed from a human or animal body for any reason (e.g., a biopsy, or tissue resected during surgery), and may be tumor tissue (including but not limited to melanoma and non-small cell lung cancer) obtained from a human patient. Conventional immunoassays may be employed, including ELISA, Western blot, immunohistochemistry, or immunoprecipitation.

By correlating the presence or level of MAGE-A3 with a disease, one of skill in the art may diagnose a disease associated with MAGE-A3 expression. Detection of MAGE-A3 in tumor tissue from a subject, such as a human subject, may be used to determine whether a subject is suitable for, or likely to be responsive to, treatments designed to treat MAGE-A3 expressing tumors. Antigen binding proteins of the present invention are useful in detecting MAGE-A3 and/or MAGE-A6 protein, and can be used in screening formalin-fixed and paraffin-embedded (FFPE) tissues for MAGE-A3 and/or MAGE-A6.

Figure 7:
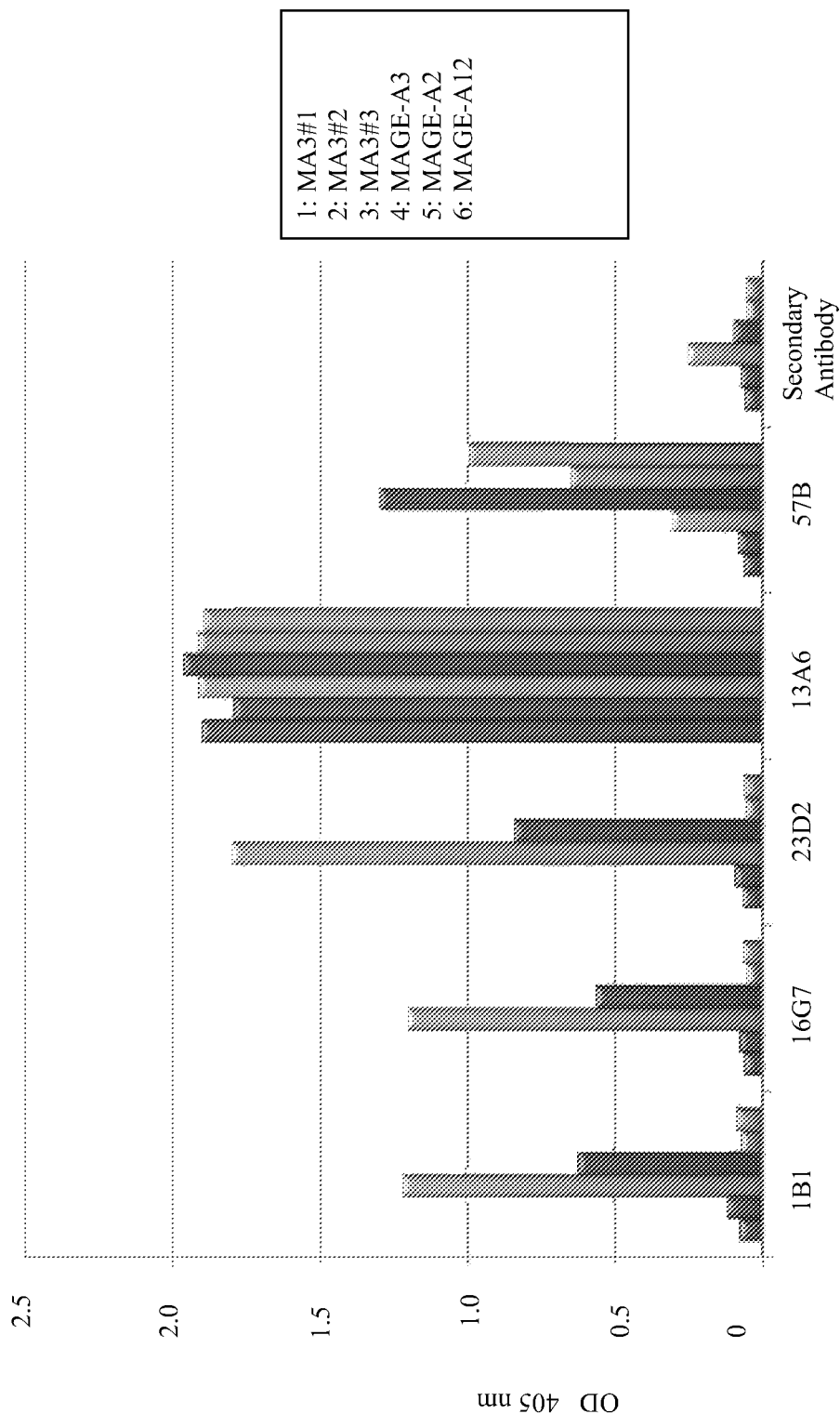
FIG. 7: Graphs the results of ELISA analysis of the reactivity of four hybridoma supernatants obtained after subcloning and adaptation of the hybridomas to growth in standard medium. Each hybridoma supernatant was tested on recombinant MAGE-A3, MAGE-A2 and MAGE-A12 proteins and on each of the three MAGE-A3 peptides conjugated to KLH. Supernatant 57B was used as positive control and goat anti-mouse-HRP alone (secondary antibody) as negative control. For each supernatant sample tested, results are given left to right for: peptide MA3#1, peptide MA3#2, peptide MA3#3, MAGE-A3, MAGE-A2, and MAGE-A12.

The predicted amino acid sequence of MAGE-N (SEQ ID NO:68) (Genebank, Locus No. AF443295; Zhang et al. *Oncology Report*, 20: 245, 2008) has an N-terminal region (amino acids 1-129) that has 97% sequence similarity to the N-terminal region of MAGE-3A, with one amino acid difference. The sequence corresponding to amino acids 73-90 in the N-terminal region of MAGE-N is identical to the amino acid sequence of the MAGE-A3 fragment in peptide MA3#3 (SEQ ID NO 37), which corresponds to amino acids 73-90 in MAGE-A3. The antigen binding proteins described here specifically bind to MA3#3 peptide (FIG. 7). Thus, the antigen binding proteins described herein may be used to detect MAGE-N in a biological sample in vitro or in vivo. Detection may be for research, therapeutic or diagnostic purposes. For example, the anti-MAGE-A3 antigen binding proteins can be used to detect MAGE-N in cultured cells, in a tissue, in bodily fluids or in serum. The tissue may have been first removed from a human or animal body for any reason (e.g., a biopsy, or tissue resected during surgery), and may be tumor tissue (including but not limited to hepatocellular carcinoma) obtained from a human patient. Conventional immunoassays may be employed, including ELISA, Western blot, immunohistochemistry, or immunoprecipitation.

By correlating the presence or level of MAGE-N with a disease such as hepatocellular carcinoma, one of skill in the art may diagnose a disease associated with MAGE-N expression. Detection of MAGE-N in tumor tissue from a subject, such as a human subject, may be used to determine whether a subject is suitable for, or likely to be responsive to, treatments designed to treat MAGE-N expressing tumors. Antigen binding proteins of the present invention are useful in detecting MAGE-N protein, and can be used in screening formalin-fixed and paraffin-embedded (FFPE) tissues for MAGE-N.

The antigen binding proteins of the present invention may be provided in a diagnostic kit comprising one or more antigen binding proteins, a detectable label, and instructions for use of the kit. For convenience, the kit may comprise the reagents in predetermined amounts with instructions for use.

Sequences

SEQ ID NO:1-11: human MAGE A1, A2, A3, A4, A5, A6, A8, A9, A10, A11, and A12, respectively.

SEQ ID NO:12-22: fragments of MAGE A1, A12, A2, A3, A6, A4, A5, A8, A10, A11, and A9 corresponding to MAGE-A3 aa66-91.

SEQ ID NO:23: consensus sequence of fragments corresponding to MAGE-A3 aa 66-91.

SEQ ID NO:24-33: fragments of MAGE A1, A12, A2, A3, A6, A4, A8, A10, A11, and A9 corresponding to MAGE-A3 aa137-180.

SEQ ID NO:34: consensus sequence of fragments corresponding to MAGE-A3 aa137-180.

SEQ ID NO:35: peptide MA3#1 for immunization.
SEQ ID NO:36: peptide MA3#2 for immunization.
SEQ ID NO:37: peptide MA3#3 for immunization.
SEQ ID NO:38-49: heavy and light chain nucleotide and amino acid sequences for mAb 1B1, mAb 16G7 and mAb 23D2.
SEQ ID NO:50-52: CDRH1-CDRH3 of mAb 1B1.
SEQ ID NO:53-55: CDRL1-CDRL3 of mAb 1B1.
SEQ ID NO:56-58: CDRH1-CDRH3 of mAb 16G7.
SEQ ID NO:59-61: CDRL1-CDRL3 of mAb 16G7.
SEQ ID NO:62-64: CDRH1-CDRH3 of mAb 23D2.
SEQ ID NO:65-67: CDRL1-CDRL3 of mAb 23D2.
SEQ ID NO:68: MAGE-N

EXAMPLES

Example 1

Synthesis of Full-length MAGE-A3 and MAGE-A3 Peptides

To reduce the chance of obtaining antibodies cross reacting with other MAGE-A proteins, divergent epitopes from MAGE-A3 protein were identified and peptides containing the epitopes were used to immunize mice. A second strategy was also used consisting of immunizing mice with the full-length recombinant MAGE-A3 protein (SEQ ID NO:3).

Divergent epitopes were identified. These epitopes originated from two regions of the MAGE-A3 sequence (SEQ ID NO:3) which showed less sequence similarity to other MAGE-A protein sequences (except MAGE-A6 sequence to which they are highly similar). The first region spans amino acids (AA) 66 to 91 (SEQ ID NO:15) of MAGE A3, and shows 73% and 76% identity with MAGE-A2 and MAGE-A12 respectively (FIG. 2). The second region comprises AA 137 to 180 of MAGE-A3 (SEQ ID NO:27) and shows 72% identity with both MAGE-A2 and MAGE-A12 (FIG. 3).

A total of three peptides containing divergent epitopes were synthesized (Table 3):

TABLE 3

| Peptide name | Corresponding amino acids in MAGE-A3 (SEQ ID NO: 3) | Peptide Sequence | SEQ ID NO |
|---|---|---|---|
| MA3#1 | AA 137-147 | CGSVVGNWQYFF | SEQ ID NO: 35 |
| MA3#2 | AA 163 to 180* | CGIELMEVDPIGHLYFAT | SEQ ID NO: 36 |
| MA3#3 | AA 73 to 90 | CGTTMNYPLWSQSYEDSSNQ | SEQ ID NO: 37 |

*The sequence of amino acids 163 to 180 in MAGE-A3 is GIELMEVDPIGHLYIFAT (see FIG. 1). Through an inadvertent error, the MA3#2 peptide was synthesized as CGIELMEVDPIGHLYFAT, and does not contain the Isoleucine residue corresponding to residue #177 of the MAGE-A3 sequence.

One or two amino acids (underlined in Table 3, above) were added to the NH₂ terminus of the MA3 peptides to facilitate their linkage to, and to distance from, the carrier protein. As the three MAGE-A3 fragments used have high sequence similarity to MAGE-A6, it was predicted that resulting antibodies would cross-react with this protein The MA3#1, MA3#2, and MA3#3 peptides were synthesized (New England Peptide, Inc.) and were directly conjugated to keyhole limpet haemocyanin (KLH). Peptide-KLH conjugates were at a concentration of 1 mg/ml. Un-conjugated lyophilised MA3#1, MA3#2, and MA3#3 peptides were also synthesised (NEP Inc).

A total of 3 mg of MAGE-A3 recombinant protein produced in baculovirus at a concentration of 0.426 mg/ml, and 3 mg of MAGE-A3 recombinant protein produced in E. coli at a concentration of 1.487 mg/ml, were obtained (GSK Biologicals, Rixensart, Belgium). MAGE-A2 recombinant protein (LVL313) at a concentration of 0.486 mg/ml, and MAGE-A12 recombinant protein (LVL314) at a concentration of 0.458 mg/ml, were also obtained (GSK Biologicals, Laval, Canada). All this material was conserved aliquoted at −20° C.

Example 2

Immunization Strategies

Two protocols, having different immunization strategies, were performed simultaneously. These experiments were approved by the institutional Animal Ethics Committee.

Each protocol consisted of immunizing a group of four 6-8 week-old female Balb/c mice purchased from Charles River Inc. Before immunizations, for each mouse a blood sample was withdrawn to obtain pre-immune sera.

The first protocol (IMM-134) consisted of immunizing the mice with a mixture of the three peptide-KLH conjugates (as described in Example 1) in the presence of the adjuvant Quil-A (Cedarlane Laboratories Ltd., Hornby, ON, Canada; Superfos Biosector, Vedbaek, Denmark). Each mouse was injected sub-cutaneously (s.c.) at days 0, 14 and 35 with 10 µg of each peptide-KLH conjugate and 10 µg of Quil-A in a volume of 100 µl. At day 45 a blood sample was withdrawn for analysis. Example 11 sets forth the detailed protocol that was followed.

The second protocol (IMM-135) consisted of immunizing the mice with the MAGE-A3 recombinant protein. Each mouse was injected sub-cutaneously (s.c.) at days 0, 14 and 35 with 20 µg of MAGE-A3 recombinant protein produced in baculovirus and 10 µg of Quil-A in a volume of 100 µl. At day 45 a blood sample was withdrawn for analysis. Example 11 sets forth the detailed protocol that was followed in conducting the present Example.

Example 3

Titer Determination, Mouse Selection and Final Boost—Results

Figure 4B:
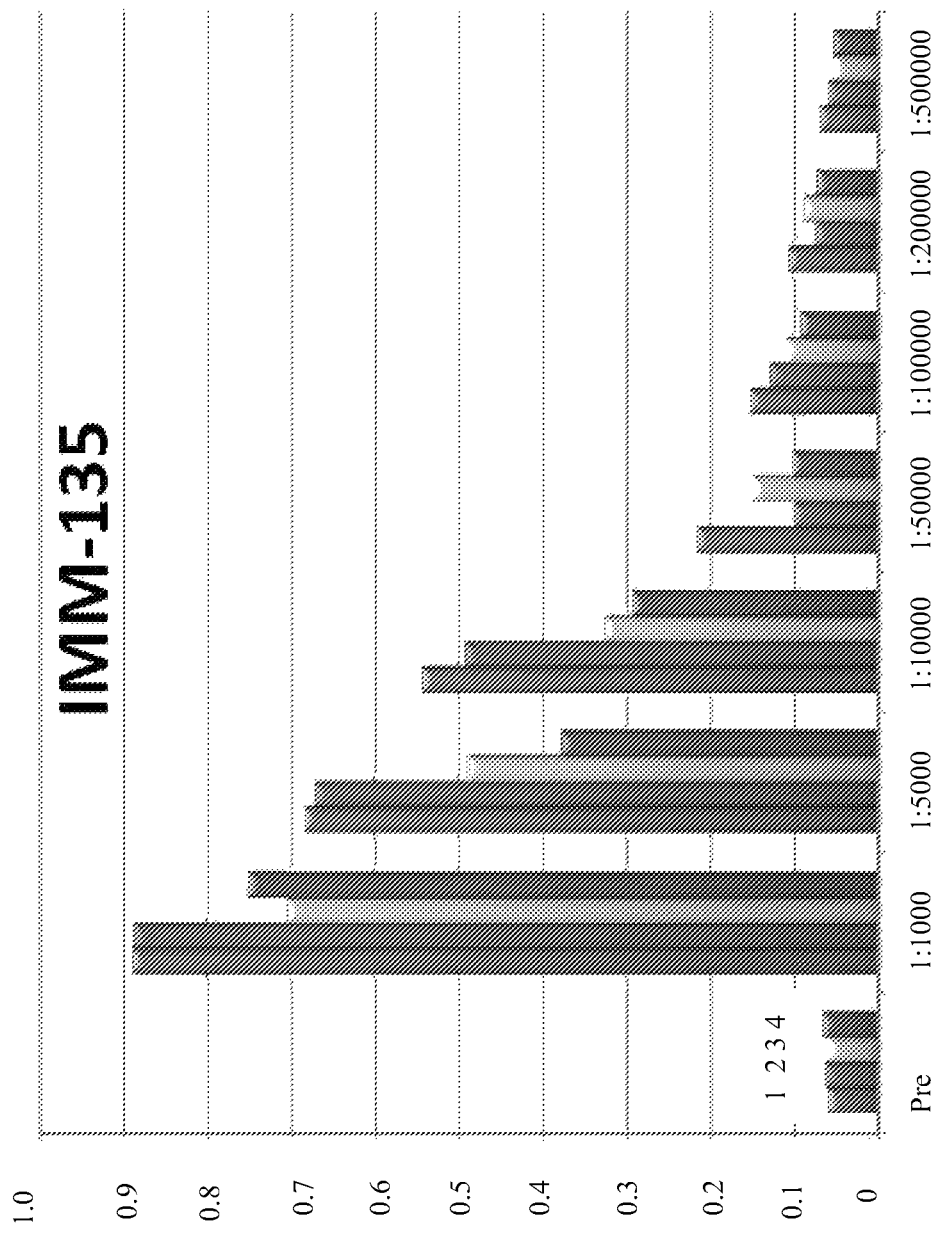
FIG. 4B: Graphs the relative anti-MAGE-A3 antibody titer in the serum of mice immunized with full-length recombinant MAGE-A3 protein (Protocol IMM-135). Pre-Immune sera (Pre), and serum dilutions from each of the four mice included in the protocol were tested in ELISA on the full-length recombinant MAGE-A3 protein (serum dilutions at 1:1000, 1:5000, 1:10,000, 1:50,000, 1:100,000, 1:200,000 and 1:500,000). The results for each dilution are given for mouse 1, 2, 3 and 4 in the order as indicated above the pre-immune (Pre) sera.
Figure 5:
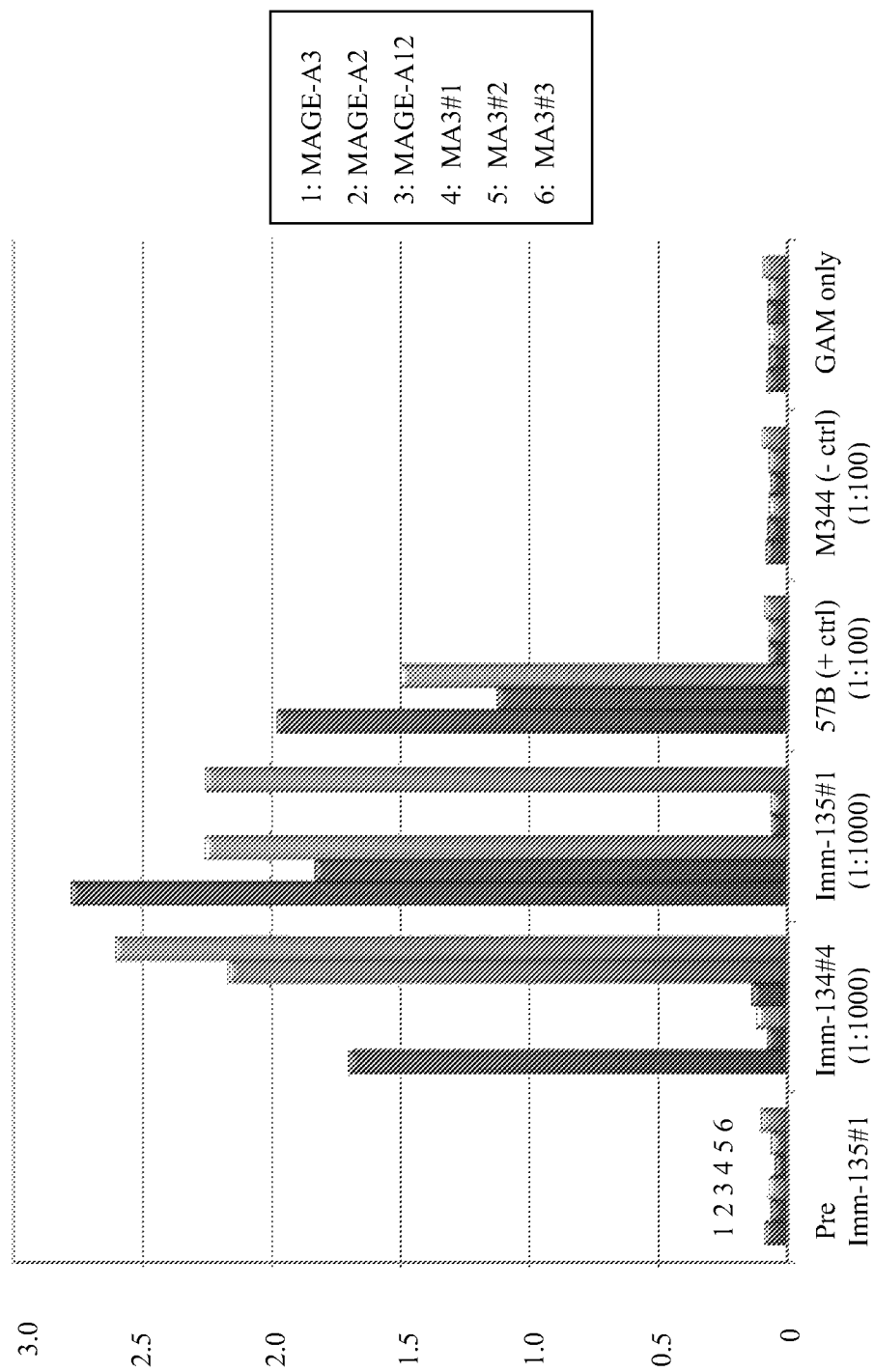
FIG. 5: Indicates the reactivity and specificity of the serum of immunized mice. Serum of mouse #4 of IMM-134 and mouse #1 of IMM-135 (diluted 1:1000) was tested in ELISA on full-length recombinant MAGE-A3, A2 and A12 as well as on three MAGE-A3 peptides conjugated to KLH. For each test sample, results are given left to right for: MAGE-A3, MAGE-A2, MAGE-A12, peptide MA3#1, peptide MA3#2 and peptide MA3#3.

Pre-immune (day 0) sera and different concentrations of sera obtained at day 45, from each immunized mouse from Example 2, were tested by ELISA on recombinant MAGE-A3 protein produced in baculovirus (FIGS. 4A and 4B). A second ELISA analysis was then performed in which the serum of one mouse from each protocol was tested with recombinant MAGE-A3, MAGE-A2 and MAGE-A12 proteins as well as with each of the three MAGE-A3 peptides (MA3#1, MA3#2 and MA3#3) conjugated to KLH. The reactivity of these sera was compared with that of pre-immune sera (mouse #1, IMM-135), mAb 57B (as positive control), the irrelevant mAb M344 (negative control), and the secondary antibody (Goat anti-mouse (GAM) IgG-HRP, Jackson ImmunoResearch) alone (negative control) (FIG. 5).

Wells of a Nunc MAXISORP™ 96-well were coated with antigen. The antigen was diluted in Tris-buffered saline (TBS) at 0.1 µg/50 µl for purified recombinant MAGE proteins, or at 0.5 µg/50 µl for peptides conjugated to KLH, and distributed at 50 µl per well and dried overnight at 37° C. The wells were washed several times in TBS and 50 µl of TBS-1% casein was added to each well. Wells were incubated for 1 hour at 37° C. and washed again several times in TBS.

50 µl of mouse serum was added, diluted in TBS-0.02% casein, then incubated for 1 hour at 37° C. in a humid chamber and washed six times with TBS.

Secondary antibody was then added: 50 µl of Horse Radish Peroxidase (HRP)-conjugated secondary antibody (GAM IgG-HRP, Jackson ImmunoResearch) was added per well, diluted 1:5000 in TBS-0.02% casein and incubated for 1 hour at 37° C. in a humid chamber. The wells were then washed six times with TBS.

Revelation: 50 µl per well of 2,2'-azino-bis(3-ethylbenzthiazoline-6-sulfonic acid) (ABTS, Chemicon International, Cat: ES004-500 ml) was added and incubated for 30 minutes at 37° C. in a humid chamber. The reaction was stopped by addition of 50 of ABTS blocking solution. Optical density at 405 nm was read on a Molecular Devices plate reader.

Sera from all eight mice were tested against MAGE-A3 protein at dilutions ranging from 1:1000 to 1:500,000. FIG. 4A shows that among the mice immunized with the mixture of the three peptides conjugated to KLH (protocol IMM-134), mouse #3 had the highest titer. The mouse with the second highest titer was mouse #4. As shown in FIG. 4B, in the group of mice immunized with the recombinant MAGE-A3 protein (protocol IMM-135), mouse #1 had the highest titer.

To determine the specificity of the antisera and to determine with which peptides antisera of the mice from protocol IMM-134 were reactive, a second ELISA analysis was performed in which the serum of a mouse from each protocol (1:1000 dilution) was tested with recombinant MAGE-A3, MAGE-A2 and MAGE-A12 proteins as well as with each of the three MAGE-A3 peptides conjugated to KLH.

FIG. 5 shows that sera of IMM-134 mouse #4 reacted with the recombinant MAGE-A3, but not the MAGE-A2 or MAGE-A12, peptides. This indicates that the immunization strategy (IMM-134) using divergent peptides was effective in producing antibodies specific to MAGE-A3/A6. The serum of this mouse was also reactive with the MAGE-A3 peptides #2 and #3, but not with peptide #1, indicating that peptide #1 was less immunogenic and that peptide #2 and #3 contained epitopes specific to MAGE-A3.

The serum of IMM-135 mouse #1, on the other hand, was not specific to MAGE-A3 as it also cross-reacted with MAGE-A2 and MAGE-A12. The strong reactivity of this serum with the MAGE-A3 peptide #3 suggests that this peptide contains an immunodominant epitope (FIG. 5).

Example 4

Cell Fusion—Results

Because of the antibody titer in serum from the mice immunized with the mixture of peptides conjugated to KLH, and because this resulted in the production of antibodies specific to MAGE-A3/A6 (see Example 3, above), splenocytes from mouse #3 (IMM-134; Example 2) were used to perform cell fusion.

The final boost was performed by injecting the same amount (10 µg of each peptide-KLH conjugate) of antigen used for previous immunizations in mouse #3 (IMM-134). However, the final boost was intended to be given intravenously (i.v.) and without adjuvant. A technical error was made in the final boost of mouse #3 (IMM-134), as the antigen was injected in presence of Quil-A which killed the mouse a few minutes after injection. The final boost was therefore repeated (without Quil-A) using mouse #4 (IMM-134). Mouse #4 was sacrificed three days after final boost, by cardiac puncture. The blood withdrawn was used to prepare serum. The spleen of mouse #4 was removed under sterile conditions, and the splenocytes were isolated and prepared for fusion.

Example 12 sets forth the protocol that was followed in conducting the present example. In brief, splenocytes were washed several times in culture medium (Iscove's Medium containing β-mercaptoethanol, 100 U of penicillin, and 100 U of streptomycin) and counted. A total number of 187.5 million living cells and 80 million dead cells (70% viability) was obtained.

Splenocytes were cultivated, diluted, washed and counted (see Example 12). A total of 66.3 million living cells and 15 million dead cells (77% viability) was obtained. The 187.5 million splenocytes were then fused with the 66.3 million SP2 cells (splenocytes/SP2 ratio of approximately 3:1). The hybridomas were seeded in twenty-three 96-well plates using 200 µl of cell suspension per well.

Example 5

Antibody Screening—Results

Thirteen days after the fusion described in Example 4, clones were ready to be tested. Observation of the 23 plates showed that between one and five clones were found in each well. The identification of anti-MAGE-A3 reactive clones was performed by ELISA.

Wells of a Nunc MAXISORP™ 96-well plate were coated with recombinant MAGE-A3 protein. The MAGE-A3 was diluted in Tris-buffered saline (TBS) at 0.1 µg/50 µl, and distributed at 50 µl per well and dried overnight at 37° C. The wells were washed several times in TBS and 50 µl of TBS-1% casein was added to each well. Wells were incubated for 1 hour at 37° C. and washed again several times in TBS.

From each well of the twenty-three 96-well plates obtained in Example 4, 50 µl of culture medium supernatant diluted in TBS-0.02% casein was obtained and transferred into a well coated with MAGE-A3 protein, then incubated for 1 hour at 37° C. in a humid chamber and washed six times with TBS.

The supernatant from well H12 of each plate was replaced with 50 µl of 57B hybridoma supernatant as a positive control.

Reactive antibodies were revealed as indicated in the ELISA protocol for MAGE-A3 set forth in Example 3.

Positive clones were those with higher absorption at 405 nm compared to the majority of other clones. At least 135 MAGE-A3 reactive clones were identified. (Results not shown). Each of these potential clones was transferred into a well of a 24-well plate containing 1 ml of complete culture medium, to expand the cells.

Example 6

Hybridoma Selection and Sub-Cloning—Results

In total, 75 clones from Example 5 that grew easily after transfer into 24-well plates were tested two days later in ELISA for reactivity with the following antigens: recombinant MAGE-A3, recombinant MAGE-A2; recombinant MAGE-A12; peptide MA3 #1 conjugated to KLH; peptide MA3 #2 conjugated to KLH; and peptide MA3#3 conjugated to KLH.

For each clone, 50 µl of culture medium supernatant was transferred into a well of a 96-well plate containing 0.1 µg/well of one of the recombinant MAGE proteins or 0.5 µg/well of one of the peptides conjugated to KLH. As positive control, 50 µl of 57B hybridoma supernatant was tested on each of the antigens. Reactive antibodies were revealed using the protocol as described in Example 3.

Figure 6A:
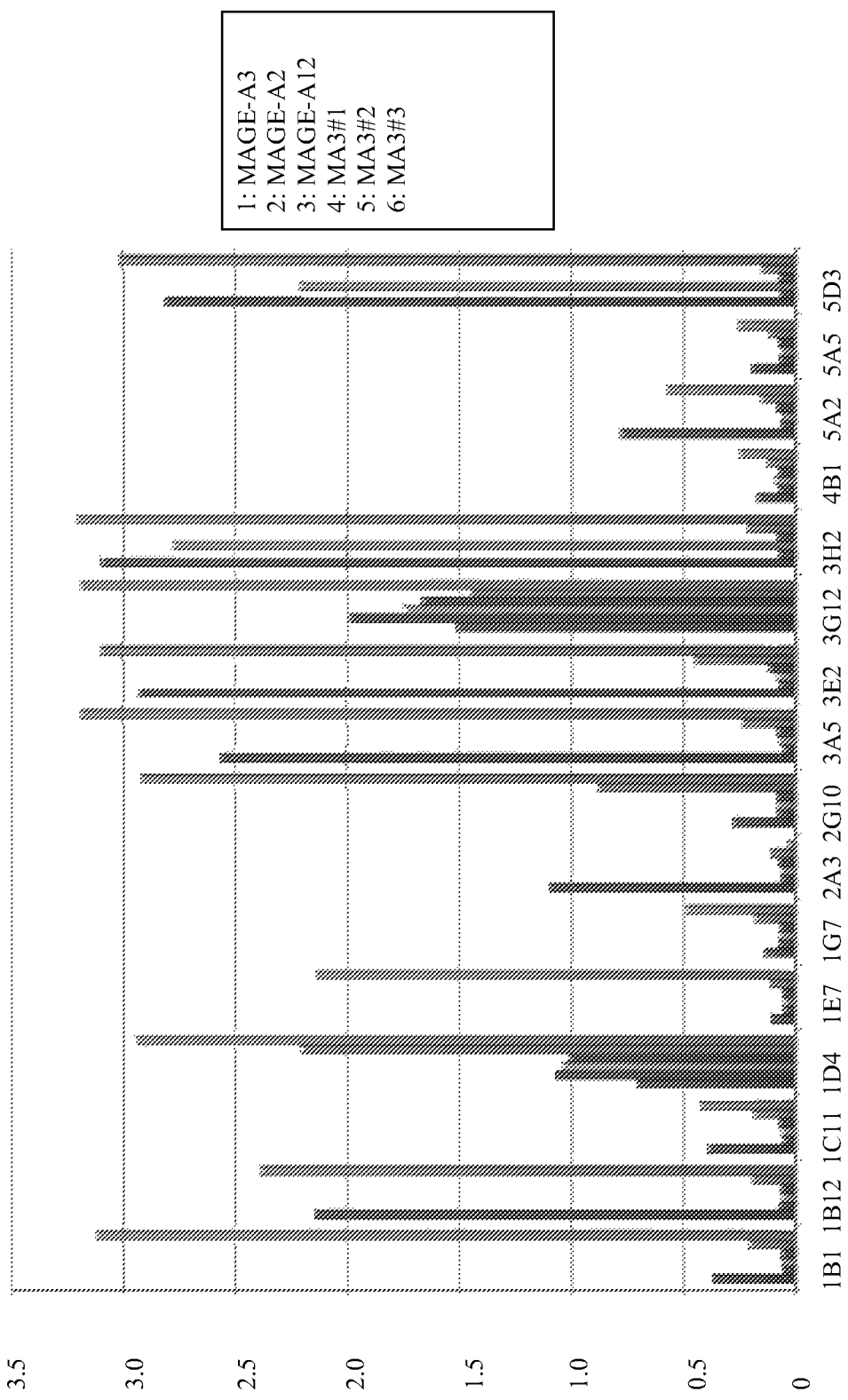
FIG. 6: Shows analysis of specificity of clone supernatants that were reactive with recombinant MAGE-A3. MAb 1B1 is shown in 6A, 16G7 and 23D2 in 6B. Clones were tested on recombinant MAGE-A3, MAGE-A2 and MAGE-A12 proteins and on each of the three MAGE-A3 peptides conjugated to KLH. For each supernatant sample tested, results are given left to right for: MAGE-A3, MAGE-A2, MAGE-A12, peptide MA3#1, peptide MA3#2 and peptide MA3#3. "Neg" indicates a negative control with no antigen in the well. Vertical axis is optical density as measured by ELISA, representing the secretory potential of the clones.
Figure 6B:
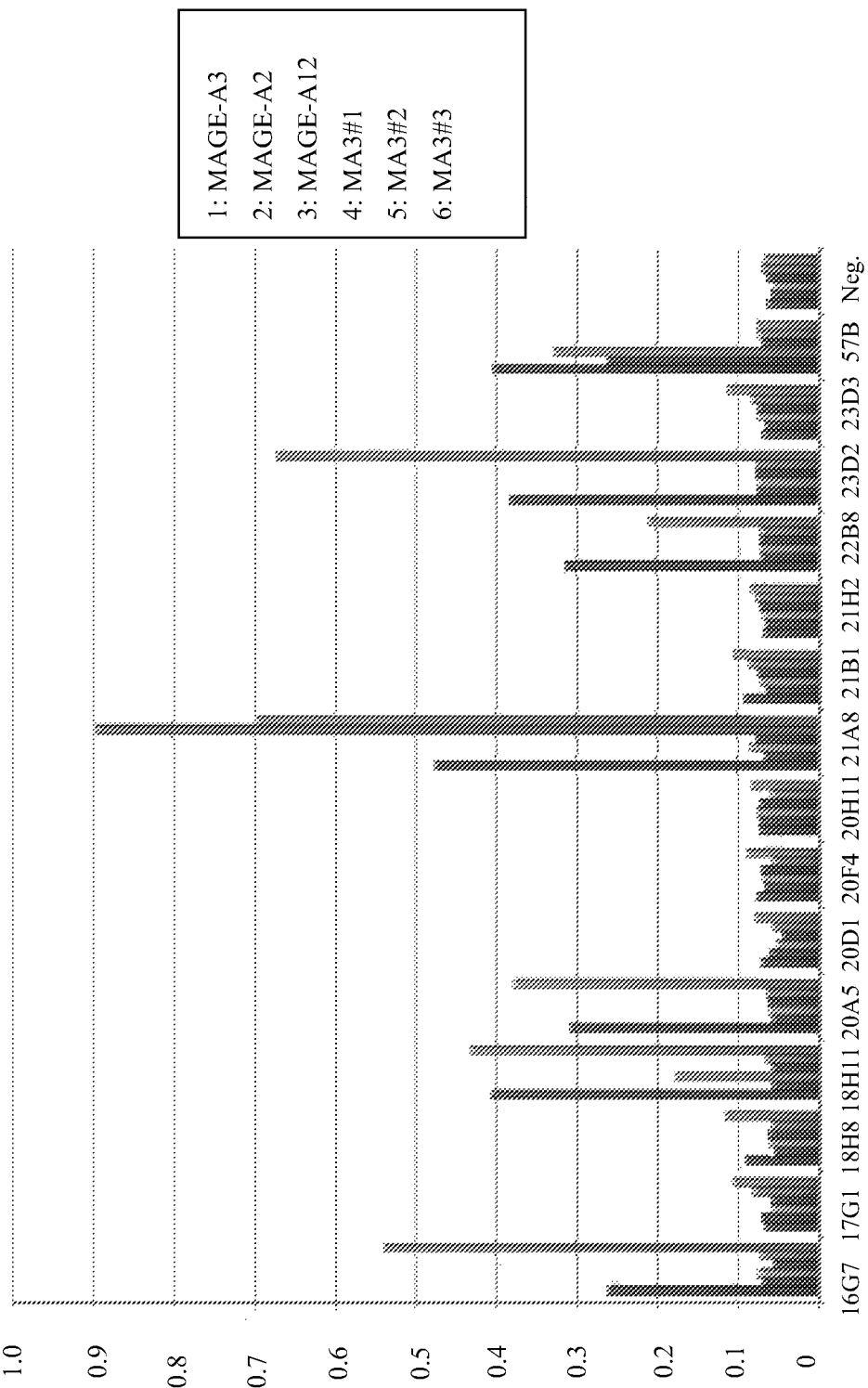

From the 75 clones, 58 conserved reactivity with MAGE-A3 but only 50 were specific to MAGE-A3 (eight clones showed cross-reactivity with MAGE-A12 and one also cross-reacted with MAGE-A2 (clones 3H2, 4B5, 5D3, 9H8, 12F3, 13A6, 18H11, 19H3)). A few clones were non-specific as they reacted with all the antigens. Regarding reactivity to the peptide-KLH conjugates, the majority of the clones specific to MAGE-A3 were reactive only with peptide MA3#3, however, a few showed also a lower reactivity with peptide MA3#2. Only two clones showed a stronger reactivity with peptide MA3#2 than with peptide MA3#3 (clones 9A5 and 21A8). FIGS. 6A and 6B shows the reactivity of some of these 75 clones, including 1B1, 16G7 and 23D2. Results for all clones not shown.

To evaluate the ability of a mAb to detect MAGE-A3 in formalin-fixed and paraffin-embedded tissues, the reactivity of a series of 22 MAGE-A3 specific clone supernatants (diluted 1:10) were tested by Immunohistochemistry (IHC) on (a) mouse xenografts of TC1 cells (TC1); (b) mouse xenografts of TC1 cells expressing MAGE-A3 (TC1-MAGE-A3 cells), and (c) a human testis sample. As controls, the same tissues were tested with mAb 57B supernatant diluted 1:200. Mouse xenografts of TC1 cells provided by GSK; see Example 13 for the IHC protocol that was followed. The 22 clones were picked randomly from among the clones with the best secretory potential and specificity, to provide an initial assessment of the capacity of the clones to detect MAGE-A3 in FFPE tissues.

TC-1 tumor cells were kindly provided by T. C. Wu (Johns Hopkins University, Baltimore, Md.). They were generated from primary lung cells of C57BL/6 mice by the successive transfer of HPV16 E6 and E7 genes and an activated ras oncogene as described previously (Lin K et al, Cancer Res. 56:21-6 (1996)). Then, TC1-cells were stably transfected with a MAGE-A3 coding plasmid.

Table 4 shows the results of the IHC analysis. None of the 22 clones showed reactivity with the TC1 xenograft. However, seven clones showed reactivity with the TC1-MAGE-A3 cells (clones 1B1, 1B12, 3A5, 5A2, 16C1, 16G7 and 23D2). Of these seven, only the 23D2 supernatant showed a weak reactivity with the human testis sample (reactivity associated with spermatogonia and occasionally with primary spermatocytes). MAb 57B was negative on xenograft of TC1 cells, but was strongly reactive with xenograft of TC1-MAGE-A3 cells and with the human testis where a strong staining of spermatocytes and spermatogonia was observed.

TABLE 4

| Clone | TC1 | TC1-MA3 | Testis |
|---|---|---|---|
| 57B (control) | -- | +++ | +++ |
| 1B1 | -- | + | -- |
| 1B12 | -- | + | -- |
| 1C11 | -- | -- | -- |

TABLE 4-continued

| Clone | TC1 | TC1-MA3 | Testis |
|---|---|---|---|
| 1E7 | -- | -- | -- |
| 3A5 | -- | + | -- |
| 5A2 | -- | + | -- |
| 5D3 | -- | -- | -- |
| 6H10 | -- | -- | -- |
| 7A2 | -- | -- | -- |
| 9H8 | -- | -- | -- |
| 11H3 | -- | -- | -- |
| 13A6 | -- | -- | -- |
| 13C8 | -- | -- | -- |
| 14A7 | -- | -- | -- |
| 14E3 | -- | -- | -- |
| 16C1 | -- | + | -- |
| 16G7 | -- | +++ | -- |
| 18H1 | -- | -- | -- |
| 21A8 | -- | -- | -- |
| 22B8 | -- | -- | -- |
| 23D2 | -- | +++ | + |
| 23D7 | -- | -- | -- |

The seven clones reactive in IHC (1B1, 1B12, 3A5, 5A2, 16C1, 16G7 and 23D2) were then sub-cloned, as was clone 13A6 (which showed cross-reactivity with MAGE-A2 and -A12 (see Example 14 for the protocol that was followed). After the first sub-cloning, clones 1B1, 3A5, 16G7 and 23D2 were still reacting to recombinant MAGE-A3.

At a second sub-cloning of 1B1, 16G7 and 23D2, 100% of the clones tested (20/20) were reacting to recombinant MAGE-A3, and these hybridomas were considered as pure clones secreting monoclonal antibodies. A second subcloning was also done for clone 13A6. Clone 3A5 could not be considered pure after a second sub-cloning since one sub-clone out of 20 sub-clones tested did not react to MAGE-A3. A third-subcloning was therefore performed for clone 3A5, and 15 sub-clones were reactive out of 24 clones tested, indicating that this clone was unstable. Therefore sub-cloning of clone 3A5 was stopped.

After the second sub-cloning of clones 1B1, 16G7, 23D2, and 13A6 these clones were gradually adapted to grow in a standard culture medium (Iscove's Medium containing 100 U of Penicillin and 100 U of Streptomycin, 50 µM β-mercaptoethanol and 10% fetal calf serum). Cells were first grown in complete medium without HAT and P288D1 conditioned medium. Then cells were grown in medium containing only 10% fetal calf serum instead of 20%. When cells were completely adapted to grow in standard complete medium, an ELISA was performed to confirm that the clones were still secreting anti-MAGE-A3 antibody (see FIG. 7). Clone 1B1, 16G7 and 23D2 reacted strongly with MAGE-A3 peptide #3 conjugated to KLH and with the recombinant MAGE-A3 protein but not with the other antigens, indicating that after sub-cloning the clones retained their original reactivity. As a safety measure, cells from all clones were frozen at various steps of the sub-cloning process.

Example 7

Preparation of a Master Stock of Frozen Cells

Hybridomas from Example 6, adapted to grow in standard culture medium, were amplified to prepare a large stock of frozen cells. For each hybridoma, at least 20 cryotubes containing $10 \times 10^6$ living cells (in 1 ml) were frozen in 90% FCS-10% DMSO (dimethyl sulfoxide). Cryotubes were frozen in a Mr. Frosty (Nalgene Cat: 5100-001) box at −80° C. overnight and then stored at −80° C.

A mechanical problem with the −80° C. biofreezer in which the master stocks were conserved occurred and the temperature rose to −40° C. Cells were immediately thawed and cultured in standard medium. A high percentage of mortality (>90%) led to the performance of two additional sub-clonings as described in Example 6 to ensure that hybridomas were pure clones of secreting hybridomas. After the second sub-cloning a new master stock was prepared comprising at least 20 cryotubes containing $10 \times 10^6$ living cells (in 1 ml) in 90% FCS-10% DMSO with a viability of over 90%. Cryotubes were frozen in a Mr. Frosty (Nalgene Cat: 5100-001) box at −80° C. overnight and transferred in liquid nitrogen.

Example 8

Antibody Characterization

To characterize the nature, activity and specificity of mAbs produced by hybridomas 1B1, 16G7 and 23D2, hybridomas obtained from Example 7 were grown in large amounts to produce 500-ml lots of hybridoma supernatant.

Antibody concentration: The antibody concentration in each of these lots of hybridoma supernatant was determined by sandwich ELISA using a mouse IgG standard curve. A 96-well plate coated with 0.5 µg/50 µl/well of goat polyclonal antibody against mouse IgG and IgM (Jackson Immunoresearch Cat: 115-005-044) was used. After coating, the plate was dried overnight at 37° C., then the wells were washed three times in TBS and 50 µl of TBS-1% casein added per well. Plates were incubated for 1 hour at 37° C., and washed again three times in TBS.

A standard curve of IgG (Sigma Cat: I5381) ranging from 0.5 to 3 ng/50 µl was prepared and added in triplicates to wells (50 µl/well). Dilutions of supernatants from hybridomas 1B1, 16G7 and 23D2, from 1:1000 to 1:8000, were prepared in PBS (phosphate buffered saline) and distributed in triplicate (50 µl/well). Plates were incubated for one hour at 37° C. in a humid chamber, then washed six times with TBS.

To each well was added 50 µl of HRP-conjugated secondary antibody (Goat anti-mouse IgG-HRP, Jackson Immuno Research Cat: 115-035-062) diluted 1:5000 in TBS-0.02% casein, and plates were incubated for 1 hour at 37° C. in a humid chamber, then wells were washed six times with TBS. ABTS (Chemicon International Cat: ES004-500 ml) was added, 100 µl per well, and incubatee for 30 minutes at 37° C. in a humid chamber. Reaction was stopped by addition of 100 µl/well of ABTS blocking solution. Optical density was read at 405 nm on a Molecular Devices plate reader.

The antibody concentration in mAb 23D2, 16G7 and 1B1 hybridoma supernatants was 103, 29 and 60 µg/ml respectively.

Antibody isotyping: The isotype of each of mAb 23D2, 16G7 and 1B1 was determined by ELISA using the Mouse Monoclonal Antibody Isotyping Kit from Sigma (Cat. No: ISO-2). Antibodies from hybridoma supernatants were captured on anti-mouse heavy chain specific antibodies and bound antibodies were revealed using a secondary antibody labelled with HRP followed by incubation in the presence of ABTS. The reagents listed in Table 5 were used.

TABLE 5

| | Catalog | Lot # |
|---|---|---|
| Anti-mouse heavy chain specific to: | | |
| IgG1 | Cat: M-5532 | 068K4753 |
| IgG2a | Cat: M-5657 | 068K4754 |

TABLE 5-continued

|  | Catalog | Lot # |
|---|---|---|
| IgG2b | Cat: M-5782 | 068K4755 |
| IgG3 | Cat: M-6157 | 068K4756 |
| IgM | Cat: M-5907 | 068K4757 |
| IgA | Cat: M-6032 | 068K4748 |
| Secondary Antibody | | |
| Anti-mouse IgG-HRP (Fab specific) | Cat: A-9917 | 50K4892 |

Antibodies were diluted 1:1000 in PBS, distributed 100 µl/well in duplicate in 96-well plate, incubated for one hour at 37° C. in a humid chamber, and washed three times in TBS-0.05% Tween 20. Then 100 µl of sample supernatant was added, incubated for one hour at room temperature, and washed three times in TBS-0.05% Tween 20. Secondary antibody was diluted 1:600 in TBS-0.05% Tween 20, distributed 100 µl/well, incubated for one hour at 37° C., and washed three times in TBS-0.05% Tween 20. ABTS (Chemicon International Cat: ES004-500 ml) was added 100 µl per well and incubated for 30 minutes at 37° C. in a humid chamber. The reaction was stopped by addition of 100 µl/well of ABTS blocking solution, and optical density was read at 405 nm on a Molecular Devices plate reader.

MAb 23D2 was determined to be an IgG2a antibody while mAbs 16G7 and 1B1 were both IgG1 antibodies (results not shown).

Purification of Antibody

The preliminary IHC analysis (Example 6) suggested that mAb 23D2 was working well in IHC. A 50-ml sample of hybridoma supernatant 23D2 (lot 090309) was used to purify mAb 23D2 using the MABTRAP™ kit (GE Healthcare Inc, United Kingdom). See Example 15 for the protocol followed. Bradford assay for IgG showed that a total of 4.32 mg of mAb 23D2 could be purified from 50 ml of supernatant.

Purity of the mAb 23D2 obtained was then analyzed by SDS-PAGE analysis (see Example 15 for the protocol followed). Results indicated that the mAb 23D2 samples were highly pure, as only two bands were shown (the heavy and light chains; 55 kDa and 23 kDa) under reducing conditions without the presence of contaminating proteins.

Antibody Biotinylation

MAb 23D2 was biotinylated in order to be used in competition assays. Purified mAb 23D2 (100 µl at 4.32 µg/µl) was first dialyzed overnight at 4° C. against 0.1M borate buffer (pH 8.8). The resulting antibody concentration was determined to be 1.74 µg/µl after dialysis (Bradford assay as described in Example 15 was used).

To 29 µl of purified mAb 23D2 at 1.74 µg/µl (50 µg in total), 2.5 µl of biotin at 0.5 µg/µl (1.25 µg in total) was added. Then 2.5 µl of DMSO (Fisher cat: D4540) was added, and incubated for four hours at room temperature. The reaction was stopped by adding 1 µl of 0.1M NH4Cl followed by incubation for 10 minutes at room temperature. The antibody was dialysed overnight against PBS at 4° C., and the concentration of biotinylated mAb after dialysis was determined to be 1.33 µg/µl (the Bradford assay as described in Example 15 was used).

Figure 8:
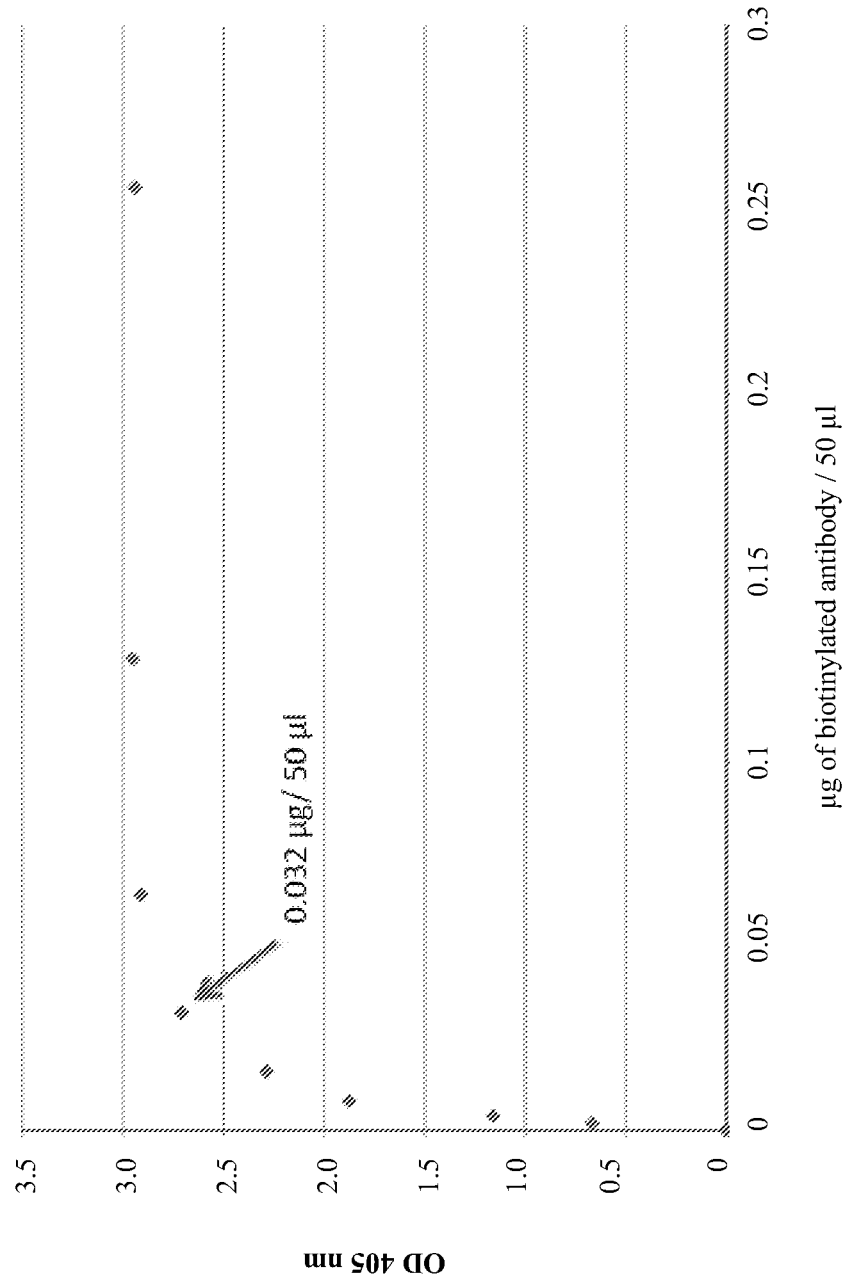
FIG. 8: Graph of the results of an ELISA analysis, showing the reactivity of biotinylated mAb 23D2 with 0.1 μg/well of recombinant MAGE-A3 protein. The dilution curve of the biotinylated mAb indicates that an antibody dilution of 0.032 μg/50 μl provides a strong signal without saturation.

An ELISA against MAGE-A3 was then performed using dilutions of biotinylated mAb 23D2 (0, 0.5, 0.1, 0.15, 0.2, 0.25 and 0.3 µg/50 µl) to determine useful conditions of use of the biotinylated mAb 23D2. The dilution curve of the biotinylated mAb indicates that an antibody dilution of 0.032 µg/50 µl provides a strong signal without saturation (FIG. 8).

Antibody Competition

To determine whether all three of mAbs 23D2, 1B1 and 16G7 are directed against the same epitope, or against different epitopes, a competition assay was performed between biotinylated mAb 23D2 and increasing amounts of mAbs 1B1 and 16G7. Unlabelled mAb 23D2 was used as a positive control of competition and mAb M75 (an irrelevant IgG1 antibody) was used as a negative control of competition.

Figure 9:
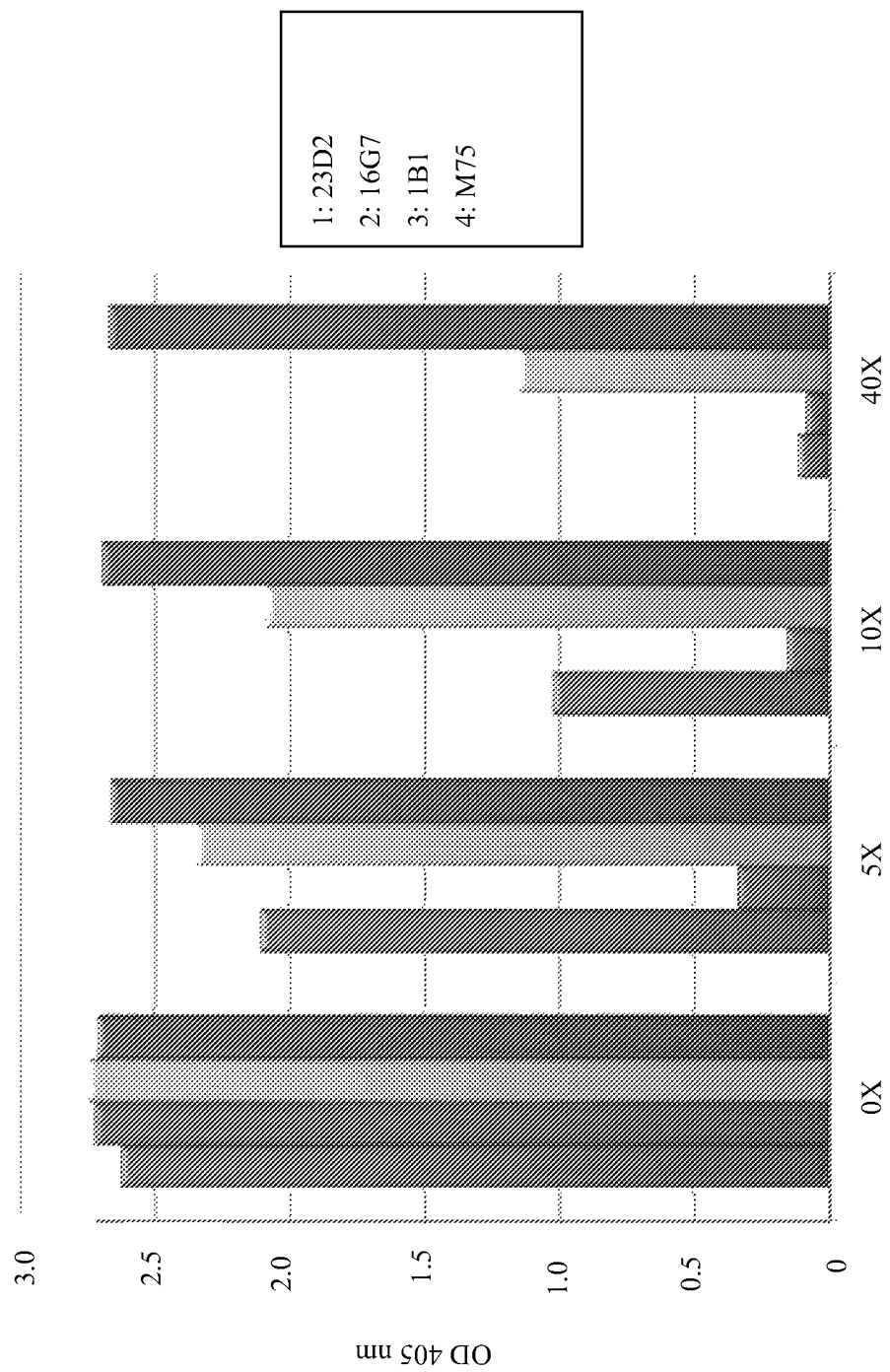
FIG. 9: Shows results of a competition assay performed between biotinylated mAb 23D2 and increasing amounts of unlabelled mAbs 1B1, 16G7, mAb23D2 (positive control), and M75 (negative control). For each concentration of unlabelled mAb (horizontal axis), results are given left to right for: 23D2, 16G7, 1B1 and M75.

FIG. 9 shows the results of the competition. At least 40 times more unlabelled mAb 23D2 was required to compete at 95% the biotinylated mAb 23D2. However, only ten times more mAb 16G7 was needed to compete at 95% the biotinylated mAb 23D2. Moreover, five times more mAb 16G7 were able to compete at 85% the biotinylated mAb 23D2. At the opposite, five times more mAb 1B1 offered little competition to the biotinylated mAb 23D2, and even at 40 times more mAb 1B1 could only compete by 55%. No competition was observed with the irrelevant mAb M75 even at 40×.

These results indicate that mAbs 23D2 and 16G7 are directed against the same epitope, but mAb 16G7 has a higher affinity/avidity than mAb 23D2. MAb 1B1 is either directed against a distinct but close epitope, as it competes partially with mAb 23D2; or is directed against the same epitope as mAb 23D2 but has a lower affinity/avidity as a greater amount (over 40×) of 1B1 antibody would be needed to compete more completely mAb 23D2.

Antibody Specificity

The specificity of mAbs 1B1, 16G7 and 23D2 were tested in Western blot analyses on HEK 293 cells transiently transfected with plasmids encoding MAGE-A1, A2, A3, A4, A6, A8, A9, A10, A11 and A12. Non-transfected cells were used as a control. Between 25 and 85 µg of lysates of transfected or non-transfected cells were electrophoresed on SDS-PAGE and transferred onto nitrocellulose. Immunodetection was performed by incubation of the blots with each of mAbs 1B1, 16G7 and 23D2. Immunodetection was additionally performed using a mixture of mAbs that together recognized all of the MAGE-A antigens expressed by the transfectants (see Table 6 for mAbs in this mixture).

Method: mini-gels were prepared with 10% acrylamide in the running gel and 4.5% acrylamide in the stacking gel. Samples were prepared in 40 µl of loading buffer (reducing conditions), the gel was loaded and migrated at 100V in the stacking gel and 200 V in the running gel. Proteins were transferred onto nitrocellulose at 100 mA during one hour at 4° C., and the membrane incubated in TBS-5% skimmed milk, and incubated with antibody diluted in TBS-1% skim milk for one hour at room temperature. Membranes were washed three times in TBS and incubated with goat anti-mouse conjugated to HRP (Jackson Immunoresearch Cat: 115-035-062) for one hour at room temperature, then washed three times in TBS. Bound antibodies were revealed by chemiluminescence (Perkin Elmer Western lightning Cat: NEL102); films were exposed between one minute and 30 minutes (Amersham Cat: 28906836).

TABLE 6

| mAb | Recognizes |
|---|---|
| 57B | MAGE-A1, A2, A3, A4, A6, A12 (gift of Dr. G. Spagnoli) |
| 14A11 | MAGE-A9 (GSK BioSA) |
| 6C1 | MAGE-A1 A2, A3, A4, A6, A10, A12 (Novocastra) |
| MA454 | MAGE-A1 (Santa Cruz Biotechnolgy) |
| 3F7 | MAGE-A8 (Abnova) |
| YN-2 | MAGE-A11 (Abnova) |

All three mAbs (1B1, 16G7 and 23D2) reacted specifically with MAGE-A3 and A6 as they showed no reactivity with other MAGE-A antigens. However, mAb 16G7 after a long exposure revealed non-specific bands of higher molecular weight found in non transfected and transfected HEK 293 cells. mAb 23D2 revealed a pattern restricted to MAGE-A3 and A6, with some bands of lower molecular weight that are likely to be degradation products. mAb 1B1, like mAb 23D2, was highly specific to MAGE-A3 and A6 and presented a clean pattern with no reactivity with degradation products. (Western Blot not shown)

Another Western blot analysis was performed using mAb 23D2 on purified full-length MAGE-A2, -A3, -A9 and -A12 recombinant proteins. For each recombinant protein, one microgram of purified protein was electrophoresed by SDS PAGE and transferred onto nitrocellulose. The blot was then tested with mAb 23D2, and with a mixture of mAbs (mAbs 14A11 and 57B) that together are able to recognize the four MAGE-A proteins. MAb 23D2 reacted specifically with MAGE-A3 and did not cross-react with purified MAGE-A2, -A9 or -A12 proteins. (results not shown)

The reactivity and specificity of mAbs 1B1, 16G7, and 23D2 was also tested by Western Blot on lysates of cancer cells expressing MAGE-A antigens at levels lower than transfectants (which may express the transgenes at high levels). Four types of cancer cells were tested (GERL, K562, STAQ and CRL-1555). Lysate of transiently MAGE-A3 transfected HEK293 cells was used as a positive control. Proteins were electrophoresed on SDS-PAGE, transferred to nitrocellulose and tested with the three mAbs.

All three mAbs reacted strongly with the HEK293-MAGE-A3 transfectant. MAbs 23D2 and 16G7 reacted positively with lysates of K562 and GERL cells, revealing bands at around 45 kDa, corresponding to MAGE-A3 and/or MAGE-A6. No reactivity was found with lysates of STAQ and CRL-1555 cells. MAb 16G7 also revealed some non-specific bands at about 60 kDa, appearing in all cell lysates.

For mAb 1B1, no reactivity with any of the four cell lysates was observed, but after very long exposure, some faint bands around 45 kDa could be observed. The lack of reactivity of mAb 1B1 with K562 and GERL cell lysates may be due to a lower affinity/avidity of this mAb, which prevented it from detecting lower amounts of antigens compared to transfected HEK293 cells in which MAGE-A3 is found in higher amounts.

A difference in the migration pattern was seen between MAGE-A3 expressed in HEK293 cells and that expressed by K562 and GERL cells; the MAGE-A3 plasmid used to transfect HEK293 cells encoded a His-tagged MAGE-A3 protein which resulted in the difference.

RT-PCR analysis of the expression of MAGE-A mRNAs showed that K562 cells expressed MAGE-A6 and GERL cells expressed MAGE-A3 and A6 (Table 7). Neither STAQ nor CRL1555 expressed MAGE-A3 or MAGE-A6. Therefore the results obtained with mAbs 23D2 and 16G7 are in accordance with the RT-PCR results.

TABLE 7

|  | MAGE-A3 | MAGE-A1, A4 | MAGE-A2, A3, A5, A6, A11, A12 | MAGE-A8, A9, A10 |
| --- | --- | --- | --- | --- |
| GERL | +++ | +++ | +++ | +++ |
| STAQ | negative | +++ | negative | + |
| CRL1555 | negative | +++ | negative | negative |
| K562 | negative | ++ | +++ | + |

Example 9

Analysis of MAGE-A3 Expression in Tissue Samples

Using supernatant from hybridomas 1B1, 16G7 and 23D2, appropriate mAb dilutions for IHC analysis of MAGE-A3/A6 expression in formalin-fixed and paraffin embedded tissues was determined. Dilutions of supernatant ranging from 1:100 to 1:1000 were tested on sections of human testis and on mouse xenografts of either TC1 cells, or TC1-MAGE-A3 transfected cells (all formalin-fixed and paraffin embedded). Mab 57B was used as a positive control of reactivity with spermatogonia and spermatocytes. IHC was performed on tissue sections that were submitted to heat-induced antigen retrieval (the protocol set forth in Example 13 was used). For mAb 23D2 (hybridoma supernatant; lot 090309), the dilution providing best results was 1:750, while for mAb 16G7 (hybridoma supernatant; lot 090309) the dilution providing best results was 1:200. In contrast, mAb 1B1 did not stain the tissues properly even at low dilution, therefore this mAb was considered unsuitable for IHC analysis in formalin-fixed and paraffin embedded tissues. (Results of IHC not shown).

Human testis, mouse TC1 and TC1-MAGE-A3 cells: On human testis samples, mAbs 23D2 and 16G7 (at the dilutions of 1:750 and 1:200, respectively) strongly stained spermatogonia and some, but not all, primary spermatocytes, suggesting that MAGE-A3 and/or A6 are expressed in the early steps of spermatogenesis. When testing mouse xenografts of TC1 and TC1-MAGE-A3 cells, both 23D2 and 16G7 gave a strong signal on TC1-MAGE-A3 xenografts (similar to that obtained with mAb 57B), but gave no signal on TC1 xenograft. However, mAb 16G7 gave a more intense background on TC1 xenografts than mAb 23D2; mAb 23D2 was more specific and gave almost no background. These results indicate that 16G7 and 23D2 stained similarly these control tissues but, as mAb 23D2 gave a more specific signal in IHC and Western blot analysis, mAb 23D2 was selected for the analysis of MAGE-A3/A6 expression in bladder tumours.

Human bladder tumors: Expression of MAGE-A3/A6 in a cohort of bladder tumour samples fixed in formalin and embedded in paraffin (FFPE) was analysed using mAb 23D2. MAb 23D2 was used to stain 33 tumour samples that remained from the 46 that had previously been analysed as reported by Picard et al., *Int. J. Cancer*, 120:2170-2177 (2007) (expression of MAGE-A3, -A4, -A8 and -A9 mRNA determined by RT-PCR analysis, IHC conducted using mAb-14A11 (MAGE-A4) and mAb57b (MAGE-A9)). FIG. 10 shows the results of IHC on this panel of tumours using mAb 23D2(MAGE-A3/A6), and compared to the results previously obtained by Picard et al.

Picard et al. reported MAGE-A4 expression in 36% (13/36) of tumors tested using mAb 57b, and MAGE-A9 expression in 42% (15/36) of tumors tested with mAb 14A11. Picard et al., *Int. J. Cancer*, 120:2170-2177 (2007). Only eight tumours out of 33 (24%) showed reactivity when tested with mAb 23D2. In most cases the reactivity was focal and restricted to less than 2% of tumour cells. In one tumour (TUM-660), 40% of cells were stained. This tumour expressed MAGE-A3 mRNA moderately but in general there was no good correlation between MAGE-A3 mRNA expression and staining with mAb 23D2, as most tumours expressing MAGE-A3 mRNA were not stained by mAb 23D2. However, expression of MAGE-A3 mRNA in most of these tumours was low suggesting that the expression was restricted to a limited number of cells, which might be missed when analyzing only one tumour section in IHC with mAb 23D2. In contrast, two tumours found positive in IHC with mAb 23D2 were negative for MAGE-A3 mRNA. In these cases, the reactivity of mAb 23D2 might be due to expression in these cells of MAGE-A6 mRNA (data on expression of MAGE-A6 in the tumors tested was not available). In addition, because of the heterogeneity of MAGE antigen expression and because the tumour portions used for IHC analysis and for RNA isolation were not necessarily juxtaposed, a lack of correlation between the present IHC and previous RT-PCR results is not interpreted as indicating a lack of specificity of mAb 23D2. Moreover, some tumour samples were old and some were fixed in Bouin's solution. Many mAbs have been shown to be highly sensitive to age and type of fixation.

Non-muscle invasive tumors: IHC analysis of MAGE-A3/A6 expression in a cohort of 46 more recent tumours all fixed in formalin and paraffine embedded (FFPE) was conducted using mAb 23D2; additionally, expression of MAGE-A4 and MAGE-A9 were assessed using mAbs 57B and 14A11, respectively. These non-muscle invasive tumours (Stage Ta, T1 and Tis) were resected between December 2005 and April 2007. Table 8 shows the results of expression of MAGE-A3/A6 in these tumours in comparison with that of MAGE-A4 and MAGE-A9. Staining by 23D2 was generally cytoplasmic although rare positive nuclei can be observed in a few cases (<10% of cases). In most cases (24/46), staining is weak, observed in 10% or less of cells, generally at a low intensity, although intermediate intensity is sometimes observed. Only nine of the 46 tumors were totally negative. Careful screening of slides most often detected a few islets of faintly positive cells. Some tumours showed an intermediate level of staining, with 20-50% of positive cells. In these, the intensity of staining was very variable, with some areas weakly stained and others stained at a medium or even strong intensity. In papillary tumours, strong staining was usually observed at the surface of the papillae. Flat tumours generally tended to be positive. A few tumours (3/46) showed a majority of positive cells (≥90%) and staining was generally at an intermediate intensity, though variable and reaching a strong intensity in patches.

TABLE 8

| Sample | MAGE-A3/A6 Staining | MAGE-A3/A6 Intensity | MAGE-A4 Staining | MAGE-A4 Intensity | MAGE-A9 Staining | MAGE-A9 Intensity |
|---|---|---|---|---|---|---|
| P1001 | + | + | + | | + | + |
| P1002 | + | +/++ | − | | +++ | +/++ |
| P1003 | +++ | + | ++++ | ++ | ++++ | +/++ |
| P1006 | ++ | +/++ | − | | ++ | +/++ |
| P1007 | + | + | ++ | ++ | ++++ | ++ |
| P1008 | ++ | +/++ | ++++ | ++ | ++++ | ++ |
| P1010 | − | | − | | − | |
| P1011 | + | + | ++ | + | + | + |
| P1012 | + | + | + | +/++ | ++ | + |
| P1013 | − | | − | | + | + |
| P1014 | − | | +++ | ++ | ++++ | ++ |
| P1015 | + | + | − | | + | ++ |
| P1018 | − | | ++++ | +/++ | ++++ | ++ |
| P1019 | − | | − | | ++++ | ++ |
| P1020 | + | + | − | | + | + |
| P1021 | + | +/++ | − | | ++++ | ++ |
| P1022 | ++++ | +/++ | +++ | +/++ | ++++ | +/++ |
| P1023 | ++++ | +/++ | ++++ | ++ | ++++ | +/++ |
| P1027 | + | +/++ | + | ++ | ++++ | ++ |
| P1029 | + | +/++ | − | | − | |
| P1031 | + | + | − | | − | |
| P1032 | − | | ++++ | ++/+++ | +++ | + |
| P1033 | ++ | +/++ | − | | + | ++ |
| P1034 | +++ | +/++ | +++ | +/++ | ++++ | +/++ |
| P1036 | + | + | − | | + | ++ |
| P1037 | + | +/++ | − | | − | |
| P1038 | + | ++ | − | | ++++ | ++ |
| P1039 | + | + | + | + | + | ++ |
| P1040 | + | +/++ | − | | − | |
| P1041 | − | | − | | − | |
| P1042 | + | + | − | | − | |
| P1043 | ++++ | ++ | ++++ | ++ | ++++ | ++ |
| P1044 | + | +/++ | ++ | | ++ | ++ |
| P1045 | + | + | + | | ++ | ++ |
| P1047 | + | +/++ | − | | + | ++ |
| P1048 | ++ | + | − | | + | ++ |
| P1050 | + | + | + | ++ | + | ++ |
| P1051 | ++ | + | − | | + | ++ |
| P1052 | + | + | − | | + | + |
| P1055 | + | + | − | | − | |
| P1056 | + | + | − | | − | |
| P1057 | − | | + | ++ | ++ | ++ |
| P1059 | ++ | + | − | | − | |
| P1060 | + | + | − | | + | +/++ |
| P1062 | − | | − | | − | |
| P1063 | +++ | +/++ | + | + | + | ++ |
| Positive | 37/46 (80%) | | 20/46 (43%) | | 35/46 (76%) | |

When compared with the expression of the two other MAGE-A antigens, it was observed that mAb 23D2 stained seven tumours that were found negative for either MAGE-A4 or MAGE-A9, suggesting that MAGE-A3/A6 could be complementary to MAGE-A9. Indeed, tumours expressing MAGE-A3/A6 and/or MAGE-A9 account for 93% of the tumours as only three tumours out of the 46 did not express any of the antigens. Contrary to MAGE-A3/A6, MAGE-A4 was not complementary to MAGE-A9 since all tumours expressing MAGE-A4 also expressed MAGE-A9. Of all these antigens, MAGE-A9 was the most homogeneously expressed as it was found in more than 50% of the tumour cells in 15 out of 46 tumours, while only 9 and 6 tumours expressed MAGE-A4 and MAGE-A3/A6 respectively in a similar proportion of tumour cells. All but one (P1063) of the tumours that expressed MAGE-A3/A6 or MAGE-A4 in more than 50% of the cells also expressed MAGE-A9 in more than 50% of the cells.

Human Testis FFPE: MAbs 1B1, 16G7 and 23D2 were tested in IHC staining on 5 μm FFPE human testis tissue using two different buffers for the antigen retrieval step. As a negative control, Universal Negative Control antibody (DakoCytomation Inc., Denmark (Code N1698)) was used.

A LabVision PT Module (Thermo Fisher Scientific, Fremont, Calif.) was used to prepare the sample slides prior to immunostaining.

1. Slide Deparaffinization and Rehydration:
   Xylene 3× (3 minutes)
   Ethanol 95% 2× (2 minutes)
   Ethanol 70% 1× (3 minutes)
   Deionised water 1× (3 minutes)

2. Antigen Retrieval Step:
   After rehydration, slides were placed at room temperature in the PT Module containing as buffer either ethylene diamine tetra-acetic acid (EDTA) at pH 8.0, or citrate at pH 6.0, and heat induced epitope retrieval was begun.
   From 25° C. to 97° C.: approximately 45 minutes
   At 97° C.: 20 minutes
   From 97° C. to 65° C.: approximately 30 minutes
   At 65° C., the slides were removed from the bath and rinsed two minutes in deionised water followed by two minutes in PBS buffer. The immunohistochemical staining was then performed, carrying out all incubations in a humidified chamber.

3. Immunohistochemical Staining

Day 1: Endogenous peroxidases were blocked by incubation in H202 1.5% in PBS for 15 minutes (coplin jar). Slides were rinsed in PBS for 2× (3 minutes) and saturated with normal goat serum 5% in PBS/BR 0.5% (Blocking Reagent, Roche, 11096176001) for 30 minutes. Slides were drained and wiped around the sections with tissue paper. Primary antibody was applied, diluted in PBS/BR 0.5%, for one night at 4° C. (dilutions 1:50; 1:100; 1:200; 1:400).

Day 2: Slides were rinsed in PBS for 2× (5 minutes) and enzyme-conjugated secondary antibody was applied to the slides (Envision, DakoCytomation Ready-to-Use for Mouse (K4004)) for 45 minutes. Slides were then rinsed in PBS 2× (3 minutes) and developed with chromogen (DAB kit, Invitrogen) for five minutes. Slides were then rinsed in deionised water for 3× (3 minutes) and counterstained with Mayer's hemalun (Klinipath) for 1-3 minutes, rinsed in tap water for five minutes, and then rinsed in deionised water for 2 minutes. Slides were then dehydrated and mounted with DePex medium (BDH Chemicals, 361254D).

Results are shown in Table A.

TABLE A

| Buffer | mAb | Result |
|---|---|---|
| Citrate pH 6.0 | 23D2 (2617 µg/mg) | Slightly positive (dilution 1:100) |
| | 16G7 (1447 µg/mg) | Negative |
| | 1B1 (1132 µg/mg) | Negative |
| EDTA pH 8.0 | 23D2 (2617 µg/mg) | Positive (nuclear - slight background; dilution 1:100) |
| | 16G7 (1447 µg/mg) | Positive (nuclear - slight background; dilution 1:100) |
| | 1B1 (1132 µg/mg) | Negative (background) |

Discussion: Thus, in immunization strategy IMM-134 reported herein, mice were immunized with MAGE-A3 peptides containing putative divergent epitopes. MAGE-A3 peptide MA3#3 was highly immunogenic as most of the positive hybridomas obtained secreted antibodies reacting with an epitope found in this sequence. MAGE-A3 peptide MA3#2 was also immunogenic but induced fewer antibodies, whereas MAGE-A3 peptide MA3 #1 was apparently less immunogenic. Three mAbs specifically reacting with MAGE-A3/A6 were produced. MAb 1B1, an IgG1 antibody, did not detect MAGE-A3/A6 well in formalin-fixed and paraffin-embedded tissues, but worked well in Western blotting. MAb 16G7 worked both in Western blot and IHC on formalin-fixed and paraffin-embedded tissues, but may not be specific as it gives a higher background. MAb 23D2, an IgG2a antibody, performed well in IHC and Western blotting. MAbs 23D2 and 16G7 react with the same epitope but 16G7 seems to have a higher affinity/avidity than mAb 23D2. MAb 1B1 apparently reacts with an epitope that is close to that recognized by mAb 23D2 or recognizes the same epitope but at a much lower affinity/avidity than the other two mAbs. These results suggest that the antibodies produced that were reactive with peptide MA3 #3 may have been directed against a single dominant epitope, and that the differences in the resulting antibodies may be due to affinity/avidity.

Example 10

Monoclonal Antibody V-gene Sequencing

The nucleotide sequence of the V-genes (coding the variable regions) of each of the mAbs 1B1, 16G7 and 23D2 were determined. Frozen cells of each hybridoma were revived and grown and antibody present in the supernatant was isotyped. Once the cells had recovered they were lysed. RNA was isolated from the cell lysates using the Promega SV Total RNA System. Reverse transcription of the RNA was performed to synthesize the first strand cDNA. V-gene amplification was carried out by PCR using the total cDNA as the template along with a pool of forward primers and a relevant isotype specific reverse primer for each reaction (1B12=IgG1 kappa; 16G7=IgG1 lambda; and 23D2=IgG2a lambda). Reverse transcription and PCR were carried out using the Promega Access Quick kit according to the manufacturer's instructions. The PCR products were purified and DNA sequenced.

The nucleotide sequences of the variable light and variable heavy chains of mAbs 1B1, 16G7 and 23D2 are shown in FIG. 11. FIG. 12 provides the amino acid sequences encoded by these nucleotide sequences, with complementarity determining regions (CDRs) underlined (framework regions not underlined). See also Table 9.

TABLE 9

| mAb 1B1 | | |
|---|---|---|
| Variable Heavy Chain (SEQ ID NO: 39) | | |
| Variable Light Chain (SEQ ID NO: 41) | | |
| CDRH1 | SDYVWN | SEQ ID NO: 50 |
| CDRH2 | YIGHSGRTSY NPSLKS | SEQ ID NO: 51 |
| CDRH3 | GGNNGFAY | SEQ ID NO: 52 |
| CDRL1 | KSSQSLLNSG NQKNYLT | SEQ ID NO: 53 |
| CDRL2 | WTSTRDS | SEQ ID NO: 54 |
| CDRL3 | QNDYSYPPT | SEQ ID NO: 55 |
| mAb 16G7 | | |
| Variable Heavy Chain (SEQ ID NO: 43) | | |
| Variable Light Chain (SEQ ID NO: 45) | | |
| CDRH1 | TNAMS | SEQ ID NO: 56 |
| CDRH2 | TITSGGGSTY YPVSVKG | SEQ ID NO: 57 |
| CDRH3 | QDYFDY | SEQ ID NO: 58 |
| CDRL1 | RSSTGAVTST NYAN | SEQ ID NO: 59 |
| CDRL2 | GTNNRAP | SEQ ID NO: 60 |
| CDRL3 | ALWYSNHWV | SEQ ID NO: 61 |
| mAb 23D2 | | |
| Variable Heavy Chain (SEQ ID NO: 47) | | |
| Variable Light Chain (SEQ ID NO: 49) | | |
| CDRH1 | SYTMS | SEQ ID NO: 62 |
| CDRH2 | TITSGGGSSY YPDSVKG | SEQ ID NO: 63 |
| CDRH3 | GGGVLLRLPL FAY | SEQ ID NO: 64 |
| CDRL1 | RSSTGAVTAS NYAN | SEQ ID NO: 65 |
| CDRL2 | GINNRAP | SEQ ID NO: 66 |
| CDRL3 | ALWYNNHWV | SEQ ID NO: 67 |

Example 11

The following two protocols were followed in conducting Example 2. The two immunization schedules (IMM-134 and IMM-135) are also outlined in Tables 10 and Table 11.

IMM-134 protocol: Immunization of Balb/c mice with a mixture of 3 MAGE-A3 peptides conjugated to KLH Immunogen: Prepare a mixture of three MAGE-A3 peptides (MA3#1, MA3#2, and MA3#3, see Example 1 herein), each peptide conjugated to keyhole limpet haemocyanin (KLH; NEP Inc, received lyophilized and reconstituted in PBS at 1 mg/ml), with a final concentration of 0.1 µg/µl for each peptide.

Adjuvant: Quil-A 10 mg/ml (Cedarlane—Superfros Biosector; Cat: 7401)

Immunization: In four Balb/c mice (Charles River Inc.), withdraw a 100-µl blood sample from each mouse (pre-immune serum). Add 5 µl of Quil-A at 10 mg/ml to 500 µl of the mixture of the three MAGE-A3 peptides (conjugated to KLH) at 0.1 µg/µl and mix well. Inject subcutaneously 100 µl/mouse. Each mouse therefore received 10 ng of each of the MAGE-A3 peptide-KLH conjugates, and 10 µg of Quil-A.

Boosts: Add 5 µl of Quil-A (10 mg/ml) to 500 µl of the mixture of the three MAGE-A3 peptides (conjugated to KLH) at 0.1 µg/µl and mix well. Inject subcutaneously 100 µl/mouse. (Each mouse therefore received 10 µg of each MAGE-A3 peptide-KLH conjugate and 10 µg of Quil-A.)

Final boost: Inject intravenously 100 µl/mouse of the mixture of the three MAGE-A3 peptides (conjugated to KLH) at 0.1 µg/µl. (The selected mouse therefore received 10 µg of each peptide-KLH conjugate but no adjuvant.)

TABLE 10

IMM-134 Schedule:

| Day | Manipulation | Mice |
|---|---|---|
| 0 | Blood withdrawal and 1st immunization TUBE I | All four |
| 14 | 1st boost TUBE II | All four |
| 35 | 2nd boost TUBE III | All four |
| 45 | Blood withdrawal | All four |
| 60 | Last boost TUBE IV | Mouse #4 |
| 63 | Mouse sacrifice and fusion | Mouse #4 |

Mouse #3 had the highest titer but did not survive the final boost because of an experimental error. The fusion was performed with mouse #4.

IMM-135 Protocol: Immunization of Balb/c Mice with Recombinant MAGE-A3

Immunogen: Prepare a solution of recombinant full-length MAGE-A3 (produced in baculovirus provided by GlaxoSmithKline). The stock solution was at 0.426 mg/ml of MAGE-A3 and a dilution in PBS was prepared at a final concentration of 0.2 µg/µl of MAGE-A3.

Adjuvant: Quil-A 10 mg/ml (N.F. 31.05.2002) (Cedarlane—Superfros Biosector; Cat: 7401).

Immunization: In four Balb/c mice (Charles River Inc.), withdraw a 100-µl blood sample from each mouse (pre-immune serum). Add 5 µl of Quil-A at 10 mg/ml to 500 µl of recombinant MAGE-A3 protein at 0.2 µg/µl and mix well. Inject subcutaneously 100 µl/mouse. (Each mouse therefore received 20 µg of recombinant MAGE-A3 and 10 µg of Quil-A.)

Boosts: Add 5 µl of Quil-A (10 mg/ml) to 500 µl of recombinant MAGE-A3 protein at 0.2 µg/µl and mix well. Inject subcutaneously 100 µl/mouse. (Each mouse therefore received 20 of recombinant MAGE-A3 and 10 µg of Quil-A.)

Final boost: Inject intravenously 100 µl/mouse of the MAGE-A3 antigen. (The selected mouse therefore received 20 µg of Recombinant MAGE-A3 but no adjuvant.)

TABLE 11

IMM-135 Schedule

| Day | Manipulation | Mice |
|---|---|---|
| 0 | Blood withdrawal and 1st immunization TUBE I | All four |
| 14 | 1st boost TUBE II | All four |
| 35 | 2nd boost TUBE III | All four |
| 45 | Blood withdrawal | All four |
| 60 | Last boost TUBE IV | All four |

Example 12

Fusion Protocol

Preparation of Iscove's-Pen/Strep-βME solution: contains Iscove's modified Dulbecco's Medium (GIBCO Cat: 12200-028) containing 100 U/ml of Penicillin, 100 U/ml of Streptomycin (Gibco Cat: 15140-122) and 50 µM β-mercaptoethanol.

Preparation of Iscove's-Pen/Strep-βME-5% FCS solution: contains Iscove's modified Dulbecco's Medium (GIBCO Cat: 12200-028) containing 100 U/ml of Penicillin, 100 U/ml of Streptomycin (Gibco Cat: 15140-122), 50 µM β-mercaptoethanol and 5% of foetal calf serum (Gibco Cat: 12483-020)

Preparation of Iscove's-Pen/Strep-βME-20% FCS Hyclone-HAT-1% CM solution: Contains Iscove's modified Dulbecco's Medium (GIBCO Cat: 12200-028) containing 100 U/ml of Penicillin, 100 U/ml of Streptomycin (Gibco Cat: 15140-122), 50 µM β-mercaptoethanol and 20% of foetal calf serum (Hyclone Cat: SH30071-03), 1×HAT (Gibco Cat: 21060-017) and 1% of conditioned medium from P388D1 cells (VP 21042005).

All solutions and media are pre-warmed at 37° C.

Preparation of splenocytes: Perform sacrifice of mouse by cardiac puncture. Remove the spleen under sterile conditions. Empty the spleen of its cell content and wash the cells three times in Iscove's-Pen/Strep-βME (Sorvall RT-6000D, 1500 rpm, 10 minutes). Count cells by Trypan blue exclusion. Results: $187.5 \times 10^6$ cells alive and $80 \times 10^6$ cells dead=70% viable cells.

Preparation of SP2 cells: Start to cultivate SP2 cells one week before the fusion. Grow cells in Iscove's-Pen/Strep-βME-10% FCS. The day before the fusion, dilute cells at $3 \times 10^5$ cells/ml. On the day of the fusion, wash cells once in Iscove's-Pen/Strep-βME (Sorvall RT-6000D, 1500 rpm, 10 minutes) and count the cells by Trypan blue exclusion. Results: $66.3 \times 10^6$ cells alive and $15 \times 10^6$ cells dead=77% viable cells.

Fusion: In a 50 ml tube, combine splenocytes and SP2 cells in a ratio of 3:1 ($187.5 \times 10^6$ splenocytes and $66.3 \times 10^6$ SP2 cells) and complete volume to 50 ml with Iscove's-Pen/Strep-βME, and centrifuge (Sorvall RT-6000D, 1500 rpm, 10 minutes). Slowly add 1 ml of 50% PEG4000 (Sigma Cat: P7306) during 1 minute to the cell pellet that was loosened after decantation. Slowly agitate the tube at 37° C. during 90 seconds. Stop the reaction by slowly adding 20 ml of Iscove's-Pen/Strep-βME (first ml in 30 seconds, two following ml in 30 seconds and the last 17 ml in 60 seconds). Complete the volume to 50 ml and incubate for 5 minutes before centrifuging the cells (Sorvall RT-6000D, 1500 rpm, 10 minutes). Wash the cells once with 50 ml of Iscove's-Pen/Strep-βME-5% FCS (Sorvall RT-6000D, 1500 rpm, 10 minutes). Resuspend cells in complete medium Iscove's-Pen/Strep-βME- 20% FCS Hyclone-HAT-1% CM and distribute 200 µl/well in twenty-three 96-well plates. Incubate at 37° C., 5% CO2 for 10-15 days.

Example 13

Immunohistochemistry (IHC)

Section of tissues: Cut the required number of 5-µm sections of the tissue to be analyzed. Sections must be prepared as fresh as possible. Older sections may decrease the intensity of the signal.

Removal of paraffin and hydration of tissues: follow the steps in Table 12 under the fume hood:

TABLE 12

| Substance | | Time |
|---|---|---|
| Bath 1 | Toluene | 5 minutes |
| Bath 2 | Toluene | 10 minutes |
| Bath 3 | Ethanol 100% | 2 minutes |
| Bath 4 | Ethanol 100% | 5 minutes |
| Bath 5 | Ethanol 95% | 5 minutes |
| Bath 6 | Ethanol 95% | 5 minutes |
| Low stream | Tap Water | 5 minutes under a low stream |

Pre-heating of the buffer: Fill the pressure cooker (Dako Diagnostique Canada Inc.) with 1200 ml of 0.01M citrate buffer pH 6.0. Close tightly the lid of the pressure cooker and place it in the microwave oven (SAMSUNG 900 W). Heat at maximal intensity until pressure indicator goes up (about 12 minutes).

Heating for antigen retrieval: When pressure indicator is down, open the pressure cooker and put the slides inside, with buffer covering the slides. Close the lid and replace in the microwave oven. Heat at maximal intensity for about 12 minutes or until the steam jet is at its maximum, then heat for an additional 6 minutes. Open the microwave oven and let the pressure indicator go down before opening the lid of the pressure cooker.

Immunohistochemistry: The immunodetection is performed using the DETECT Super stain System (HRP) (ID Labs Inc Cat #IDST1007). Put the slides in PBS 1× for at least five minutes. Block endogenous peroxydases by incubating the slides in a bath of H2O2 3% (Laboratoire Mat #HR-0133) for five minutes. Rinse in a bath of PBS 1×. Remove excess buffer using absorbing paper and place the slide in a humid chamber. Proceed with one slide at a time to avoid drying of the tissue. Add 2 to 3 drops of blocking serum buffer and incubate for 20 minutes at room temperature. Remove excess buffer and add the primary antibody at the desired dilution (150 to 200 µl according to the size of the tissue). Incubate overnight at room temperature. Wash in two baths of PBS. Remove excess buffer as described above. Add 200-250 µl of biotinylated anti-Immunoglobulin (Linking Reagent) and incubate for 20 minutes at room temperature. Wash 2 times in PBS. Remove excess buffer using absorbing paper and place the slide in a humid chamber. Proceed with one slide at a time to avoid drying of the tissue. Add 200-250 µl of ultra-streptavidine/peroxidase complexes (Labeling Reagent) and incubate for 20 minutes at room temperature. Wash 2 times in PBS. Remove excess buffer using absorbing paper and place the slide in a humid chamber. Proceed with one slide at a time to avoid drying of the tissue. Add 250 µl per slide of DAB solution (Zymed Cat: 00-2014) and incubate (the incubation time must be optimized for each mAb in order to avoid saturation of the signal). Rinse three times in a distilled H2O bath.

Counter staining: Incubate the slides in Harris's hematoxylin solution (Fischer Cat: SH26-500D) from 30 seconds to one 1 minute. Check the counter staining under the microscope. Remove the excess of dye under tap water.

Slide mounting: follow the steps in Table 13 under the fume hood:

TABLE 13

| | Substance | Time |
|---|---|---|
| Bath 7 | Ethanol 50% | 1 minute |
| Bath 8 | Ethanol 70% + 10 drops of ammoniac 30% | 2 minutes |
| Bath 9 | 95% Ethanol | 1 minute |
| Bath 10 | 100% Ethanol | 2 minutes |
| Bath 11 | 100% Ethanol | 2 minutes |
| Bath 12 | isopropanol | 1 minute |
| Bath 13 | xylene | 2 minutes |
| Bath 14 | xylene | Keep in xylene until mounting |

Proceed with 1 slide at a time. Put a drop of Entellan (BDH, Cat: UN 1866) on the tissue. Put a cover slip onto the Entellan. Let dry, carefully identify the slides and read under microscope.

Example 14

Hybridoma Sub-cloning and Culture

Transfer each candidate clone into a well of a 6-well plate containing 2.5 ml of complete medium (Iscove's-Pen/Strep-βME-20% FCS Hyclone-HAT-1% CM). Incubate plates at 37° C. in 5% CO2 until cells have reached the needed density.

Count cells by Trypan blue exclusion. Transfer 3,750 cells into a 13-ml tube. Complete the volume to 7.5 ml (100 cells/200 µl) with complete medium. Prepare serial 1:10 dilutions from this tube to obtain suspensions containing 10 cells/200 µl and 1 cell/200 µl. Distribute each of these three cell suspensions (100, 10 and one cells per 200 µl) into 32 wells (200 µl/well) of a 96-well plate and incubate the plate at 37° C., 5% CO2 between 10-15 days.

Clones growing in the wells containing the one cell/200 µl suspension are tested in ELISA for reactivity with the recombinant MAGE-A3 protein (reactive clones are deemed positive). The clones tested are visually controlled to ensure that only one colony is present in the well. If no clone is obtained from wells containing 1 cell/200 µl suspension, clones growing in the wells containing the 10 cells/200 µl suspension, or the 100 cells/200 µl suspension, are tested in ELISA for reactivity with the recombinant MAGE-A3 protein, with the clones visually controlled to ensure that only one colony is present in the well.

A positive clone is transferred into a well of a 6-well plate and cells are sub-cloned another time as described above to ensure clonality. Clonality is obtained when all sub-clones tested by ELISA are positive.

Final sub-clones are adapted gradually to grow in standard medium (Iscove's-Pen/Strep-βME-10% FCS).

Hybridomas adapted in standard medium are frozen in 90% FCS-10% DMSO ($10 \times 10^6$ cells/cryotube) in a Mr Frosty freezing container (Nalgene Cat: 5100-0001) overnight at −80° C. and then transferred in a liquid nitrogen tank after at least 24 hours at −80° C.

Example 15

Purification of Antibody

The purification of antibody from hybridoma supernatant is performed using the MABTRAP™ kit (GE Healthcare Cat: 17-1128-01).

Preparation: Allow the column and buffers to warm at room temperature. Prepare buffer as indicated in the instructions. Prepare collection tubes by adding 60-200 μl of neutralizing buffer per ml of fractions to be collected. Centrifuge and filter the hybridoma supernatant to remove any particles.

Purification: Fill a syringe with water, connect it to the column and wash out the ethanol preservative with 5 ml of water. Equilibrate the column with 15 ml of binding buffer. Apply 50 ml of hybridoma 23D2 supernatant (Lot: 090309) to the column by slowly passing the supernatant using a syringe. Wash with 25 ml of binding buffer and elute with 5 ml of elution buffer in 5 fractions of 1 ml each. Determine the O.D. 280 of each fraction (sample diluted 1:100). Result: For 23D2 hybridoma supernatant, the peak was found in fraction #2 (O.D. 280 nm=0.055).

Determining the antibody concentration by Bradford Assay: Prepare a standard curve using, 0, 2.5, 5, 10, 15, 20, 25 and 30 μg of IgG (Sigma Cat: I5381). Complete to 100 μl with PBS and add 1 ml of Bradford reagent (VP270908). Mix well. Determine the concentration of 2, 5 and 10 μl of Mab 23D2 fraction #2. Complete to 100 μl with PBS and add 1 ml of Bradford reagent (VP270908). Mix well. Read Optical Density (OD) at 595 nm. Determine the concentration using the equation of the curve. Result: the concentration of 23D2 fraction #2 was 4.32 μg/μl.

Analysis of the purity of mAb 23D2: Prepare a mini-gel with 10% acrylamide in the running gel and 4.5% acrylamide in the stacking gel. Load the gel with two samples (2 and 10 μg) of purified 23D2 (4.32 μg/μl) in 40 μl of reducing loading buffer (in presence of β-mercaptoethanol). After electrophoresis on a 10% polyacrylamide gel at 150V for 90 minutes (also including molecular weight markers), stain the gel using Coomassie blue solution during 30 minutes. Wash the gel in destaining solution overnight and the next day photograph the gel under white light.

Example 16

Canonicals

In mammalian species, antibody polypeptides contain constant (i.e., highly conserved) and variable regions. Within the variable regions are the CDRs and the so-called "framework regions" (amino acids within the variable region of the heavy or light chain but outside the CDRs). The CDRs are non-contiguous stretches of amino acids within the variable regions but, regardless of species, the positional locations of these critical amino acid sequences within the variable heavy and light chain regions are similar. The variable heavy and light chains of all canonical antibodies each have 3 CDR regions (termed L1, L2, L3, H1, H2, H3) for the respective light (L) and heavy (H) chains. The accepted CDR regions have been described by Kabat et al, *J. Biol. Chem.* 252:6609-6616 (1977).

Canonical subtypes for mAbs 1B1, 16G7 and 23D2 were predicted based on the Martin & Thornton canonical definitions (Martin & Thornton, *J. Mol. Biol.* 263:800-815 (1996)).

Canonical residues found in the CDR or framework regions of monoclonal antibodies 1B1, 16G7 and 23D2 are shown in Tables 14-28 below as underlined and bolded. If the residue present in the mAb sequence is not present in the canonical set, it is shown in brackets. Alternative residues (from the canonical set) are shown in regular type. Numbering of amino acids in Tables 15-29 follow the Kabat numbering scheme:

| Kabat Light chain | | | | | | | | | |
|---|---|---|---|---|---|---|---|---|---|
| 0 | 1 | 2 | 3 | 4 | 5 | 6 | 7 | 8 | 9 |
| 10 | 11 | 12 | 13 | 14 | 15 | 16 | 17 | 18 | 19 |
| 20 | 21 | 22 | 23 | 24 | 25 | 26 | 27 | | |
| 27A | 27B | 27C | 27D | 27E | 27F | | | 28 | 29 |
| 30 | 31 | 32 | 33 | 34 | 35 | 36 | 37 | 38 | 39 |
| 40 | 41 | 42 | 43 | 44 | 45 | 46 | 47 | 48 | 49 |
| 50 | 51 | 52 | 53 | 54 | 55 | 56 | 57 | 58 | 59 |
| 60 | 61 | 62 | 63 | 64 | 65 | 66 | 67 | 68 | 69 |
| 70 | 71 | 72 | 73 | 74 | 75 | 76 | 77 | 78 | 79 |
| 80 | 81 | 82 | 83 | 84 | 85 | 86 | 87 | 88 | 89 |
| 90 | 91 | 92 | 93 | 94 | 95 | | | | |
| 95A | 95B | 95C | 95D | 95E | 95F | 96 | 97 | 98 | 99 |
| 100 | 101 | 102 | 103 | 104 | 105 | 106 | | | |
| 106A | | | | | | | 107 | 108 | 109 |
| Kabat Heavy chain | | | | | | | | | |
| 0 | 1 | 2 | 3 | 4 | 5 | 6 | 7 | 8 | 9 |
| 10 | 11 | 12 | 13 | 14 | 15 | 16 | 17 | 18 | 19 |
| 20 | 21 | 22 | 23 | 24 | 25 | 26 | 27 | 28 | 29 |
| 30 | 31 | 32 | 33 | 34 | 35 | | | | |
| 35A | 35B | | | | | 36 | 37 | 38 | 39 |
| 40 | 41 | 42 | 43 | 44 | 45 | 46 | 47 | 48 | 49 |
| 50 | 51 | 52 | | | | | | | |
| 52A | 52B | 52C | 53 | 54 | 55 | 56 | 57 | 58 | 59 |
| 60 | 61 | 62 | 63 | 64 | 65 | 66 | 67 | 68 | 69 |
| 70 | 71 | 72 | 73 | 74 | 75 | 76 | 77 | 78 | 79 |
| 80 | 81 | 82 | | | | | | | |
| 82A | 82B | 82C | 83 | 84 | 85 | 86 | 87 | 88 | 89 |
| 90 | 91 | 92 | 93 | 94 | 95 | 96 | 97 | 98 | 99 |
| 100 | | | | | | | | | |
| 100A | 100B | 100C | 100D | 100E | 100F | 100G | 100H | 100I | 100J |
| 100K | 101 | 102 | 103 | 104 | 105 | 106 | 107 | 108 | 109 |
| 110 | 111 | 112 | 113 | | | | | | |

1B1 H1—CANONICAL 2

LOOP H1 2/11A 11

SOURCE [1baf]

TABLE 14

| FR1 | CDRH1 | FR2 | CDRH2 | FR3 | CDRH3 |
|---|---|---|---|---|---|
| H2 V | H32 D | H36 W | H50 Y | H69 I | H96 W (G) |
| H20 L | H34 A (V) | H48 M | H53 Y (H) | H76 N | |
| H22 C | H35 W | | | H78 F | |
| H24 V | | | | H80 L | |
| H26 G | | | | H92 C | |
| H29 I | | | | | |

1B1 H2—CANONICAL 1

LOOP H2 1/9A 9

SOURCE [1gig]

TABLE 15

| FR2 | CDRH2 | FR3 |
|---|---|---|
| H47 WY | H51 IMV | H69 IM |
| | H55 G | H71 RKV |
| | H59 YL | |

1B1 L1—CANONICAL 3

LOOP L13/17A 17

SOURCE [1hil]

TABLE 16

| FR1 | CDRL1 | FR2 | FR3 | CDRL3 |
|---|---|---|---|---|
| L2 I | L27B L | L35 W | L71 YF | L90 N |
| L4 M | L33 L | | | L93 NS |
| L23 C | | | | |

1B1 L2—CANONICAL 1
LOOP L2 1/7A 7
SOURCE [1lmk]

TABLE 17

| FR1 |
|---|
| L23C |

1B1 L3—CANONICAL 1
LOOP L3 1/9A 9
SOURCE [1tet]

TABLE 18

| FR1 | CDRL1 | FR3 | CDRL3 | FR4 |
|---|---|---|---|---|
| L2 ILV | L27A SNDTE | L88 C | L89 QSGFL | L98 F |
| L3 VQLE | L27C | | L90 QNH | |
| L4 ML | DLYVISNFHGT | | L91 NFGSRDHTYV | |
| | L31 SNTKG | | L92 NYWTSRQHAD | |
| | L32 FYNAHSR | | L93 ENGHTSRA | |
| | L33 MLVIF | | L94 DYTVLHNIWPS | |
| | | | L95 P | |
| | | | L96 PLYRIWF | |
| | | | L97 T | |

16G7 H1—CANONICAL 1
LOOP H1 1/10A 10
SOURCE [2fbj]

TABLE 19

| FR1 | CDRH1 | FR2 | CDRH2 | FR3 | CDRH3 |
|---|---|---|---|---|---|
| H2 VIG | H32 IHYFTNCED | H36 W | H51 LIVTSN | H69 ILFMV | H102 YHVISDG |
| H4 LV | H33 YAWGTLV | H48 IMVL | | H78 ALVYF | |
| H20 LIMV | H34 IVMW | | | H80 LM | |
| H22 C | H35 HENQSYT | | | H90 YF | |
| H24 TAVGS | | | | H92 C | |
| H26 G | | | | H94 RKGSHN | |
| H29 IFLS | | | | | |

16G7 H2—CANONICAL 3
LOOP H2 3/10B 10
SOURCE [1igc]

TABLE 20

| CDRH1 | FR2 | CDRH2 | FR3 |
|---|---|---|---|
| H33 AGVYW | H47 W | H50 GTYFIEV | H69 I |
| | | H51 IV | H71 R |
| | | H52 SFWH (T) | H78 L |
| | | H53 DGSN | |
| | | H54 SG | |
| | | H56 SYTNDR | |
| | | H58 GYHFDN | |
| | | H59 Y | |

16G7 L1—CANONICAL 7
LOOP L1 7/14B 14
SOURCE [1gig]

TABLE 21

| FR1 | CDRL1 | FR2 | CDRL2 | FR3 | CDRL3 |
|---|---|---|---|---|---|
| L2 AQ | L26 S | L35 W | L51 T | L66 L | L90 L |
| L4 V | L27A G | L48 I | | L71 A | |
| L23 C | L27B AT | | | L88 C | L93 SN |
| | L27C V | | | | |
| | L31 N | | | | |
| | L32 YH | | | | |
| | L33 A | | | | |

16G7 L2—CANONICAL 1
LOOP L2 1/7A 7
SOURCE [1lmk]

TABLE 22

| FR1 |
|---|
| L23C |

16G7 L3—CANONICAL 8
LOOP L3 8/?/9D 9
SOURCE [1gig]

TABLE 23

| FR1 | CDRL1 | FR3 | CDRL3 | FR4 |
|---|---|---|---|---|
| L2 A | L27A G | L88 C | L89 A | L98 F |
| L3 V | L27C V | | L90 L | |
| L4 V | L31 N | | L91 W | |
| | L32 Y | | L92 Y | |

TABLE 23-continued

| FR1 | CDRL1 | FR3 | CDRL3 | FR4 |
|---|---|---|---|---|
| | L33 A | | L93 S | |
| | | | L94 N | |
| | | | L95 H L | |
| | | | L96 W | |
| | | | L97 V | |

23D2 H1—CANONICAL 1
LOOP H1 1/10A 10
SOURCE [2fbj]

TABLE 24

| FR1 | CDRH1 | FR2 | CDRH2 | FR3 | CDRH3 |
|---|---|---|---|---|---|
| H2 VIG | H32 IHYFTNCED | H36 W | H51 LIVTSN | H69 ILFMV | H102 YHVISDG |
| H4 LV | H33 YAWGTLV | H48 IMVL | | H78 ALVYF | |
| H20 LIMV | H34 IVMW | | | H80 LM | |
| H22 C | H35 HENQSYT | | | H90 YF | |
| H24 TAVGS | | | | H92 C | |
| H26 G | | | | H94 RKGSHN | |
| H29 IFLS | | | | | |

23D2 H2—CANONICAL 3
LOOP H2 3/10B 10
SOURCE [1igc]

TABLE 25

| CDRH1 | FR2 | CDRH2 | FR3 |
|---|---|---|---|
| H33 AGVYW (T) | H47 W | H50 GTYFIEV | H69 I |
| | | H51 IV | H71 R |
| | | H52 SFWH (T) | H78 L |
| | | H53 DGSN | |
| | | H54 SG | |
| | | H56 SYTNDR | |
| | | H58 GYHFDN | |
| | | H59 Y | |

23D2 L1—CANONICAL 7
LOOP L1 7/14B 14
SOURCE [1gig]

TABLE 26

| FR1 | CDRL1 | FR2 | CDRL2 | FR3 | CDRL3 |
|---|---|---|---|---|---|
| L2 AQ | L26 S | L35 W | L51 T (I) | L66 L | L90 L |
| L4 V | L27A G | L48 I | | L71 A | L93 SN |
| L23 C | L27B AT | | | L88 C | |
| | L27C V | | | | |
| | L31 N | | | | |
| | L32 YH | | | | |
| | L33 A | | | | |

23D2 L2—CANONICAL 1
LOOP L2 1/7A 7
SOURCE [1lmk]

TABLE 27

| FR1 |
|---|
| L23 C |

23D2 L3—CANONICAL 8
LOOP L3 8?/9D 9
SOURCE [1gig]

TABLE 28

| FR1 | CDRL1 | FR3 | CDRL3 | FR4 |
|---|---|---|---|---|
| L2 A | L27A G | L88 C | L89 A | L98 F |
| L3 V | L27C V | | L90 L | |
| L4 V | L31 N | | L91 W | |
| | L32 Y | | L92 Y | |
| | L33 A | | L93 S (N) | |
| | | | L94 N | |
| | | | L95 HL | |
| | | | L96 W | |
| | | | L97 V | |

---

The invention claimed is:

1. An antigen binding protein that specifically binds to MAGE-A3 and MAGE-A6, but which does not specifically bind to MAGE-A2 or MAGE-A12, comprising (1) a heavy chain variable domain comprising a CDRH1 region, a CDRH2 region, and a CDRH3 region, where said CDRH1 region is N-terminal to said CDRH2 and CDRH3 regions, and said CDRH2 region is between said CDRH1 and CDRH3 regions, and (2) a light chain variable domain comprising a CDRL1 region, a CDRL2 region, and a CDRL3 region, where said CDRL1 region is N-terminal to said CDRL2 and CDRL3 regions, and said CDRL2 region is between said CDRL1 and CDRL3 regions, said antigen binding protein selected from the group consisting of:
(a) an antigen binding protein comprising a CDRH1 region of SEQ ID NO: 50, a CDRH2 region of SEQ ID NO: 51, a CDRH3 region of SEQ ID NO:52, a CDRL1 region of SEQ ID NO:53, a CDRL2 region of SEQ ID NO:54, and a CDRL3 region of SEQ ID NO:55;
(b) an antigen binding protein comprising a CDRH1 region of SEQ ID NO: 56, a CDRH2 region of SEQ ID NO: 57, a CDRH3 region of SEQ ID NO:58, a CDRL1 region of SEQ ID NO:59, a CDRL2 region of SEQ ID NO:60, and a CDRL3 region of SEQ ID NO:61; and
(c) an antigen binding protein comprising a CDRH1 region of SEQ ID NO: 62, a CDRH2 region of SEQ ID NO: 63, a CDRH3 region of SEQ ID NO:64, a CDRL1 region of SEQ ID NO:65, a CDRL2 region of SEQ ID NO:66, and a CDRL3 region of SEQ ID NO:67.

2. An antigen binding protein according to claim 1 comprising :
(i) a heavy chain variable region of SEQ ID NO:47 and a light chain variable region of SEQ ID NO:49;
(ii) a heavy chain variable region of SEQ ID NO:39 and a light chain variable region of SEQ ID NO:41; or
(iii) a heavy chain variable region of SEQ ID NO:43 and a light chain variable region of SEQ ID NO:45.

3. A nucleic acid molecule which encodes an antigen binding protein according to claim 1.

4. An expression vector comprising the nucleic acid molecule of claim 3.

5. A recombinant host cell comprising the expression vector of claim 4.

6. A method for the production of an antigen binding protein comprising the step of culturing the host cell of claim 5 and recovering the antigen binding protein produced by said cell.

7. A method of detecting MAGE-A3 and/or MAGE-A6 in human formalin-fixed paraffin embedded tissue, comprising performing an enzyme-linked immunosorbant assay on said tissue using an antigen binding protein according to claim 1.

8. The method of claim 7 where said tissue is tumor tissue.

9. The method of claim 8 where said tumor tissue is melanoma or non-small cell lung cancer.

* * * * *